(12) United States Patent
Maguire et al.

(10) Patent No.: US 9,737,503 B2
(45) Date of Patent: Aug. 22, 2017

(54) SHORT ACTING PHENYLALKYLAMINE CALCIUM CHANNEL BLOCKERS AND USES THEREOF

(71) Applicant: Milestone Pharmaceuticals Inc., Saint-Laurent (CA)

(72) Inventors: Martin P. Maguire, Westmount (CA); Elise Rioux, Montreal (CA); Harry J. Leighton, Rockport, ME (US)

(73) Assignee: Milestone Pharmaceuticals Inc., Saint-Laurent, Quebec (CA)

( * ) Notice: Subject to any disclaimer, the term of this patent is extended or adjusted under 35 U.S.C. 154(b) by 0 days.

(21) Appl. No.: 15/262,567

(22) Filed: Sep. 12, 2016

(65) Prior Publication Data

US 2016/0374982 A1    Dec. 29, 2016

Related U.S. Application Data

(60) Division of application No. 14/949,107, filed on Nov. 23, 2015, now Pat. No. 9,463,179, which is a division of application No. 14/305,626, filed on Jun. 16, 2014, now Pat. No. 9,227,918, which is a continuation of application No. 12/664,026, filed as application No. PCT/US2008/007665 on Jun. 19, 2008, now abandoned.

(60) Provisional application No. 60/936,440, filed on Jun. 20, 2007.

(51) Int. Cl.

| | |
|---|---|
| *A61K 31/275* | (2006.01) |
| *C07C 229/00* | (2006.01) |
| *C07C 255/43* | (2006.01) |
| *A61K 31/277* | (2006.01) |
| *C07C 229/34* | (2006.01) |
| *C07C 255/42* | (2006.01) |
| *C07C 229/38* | (2006.01) |
| *A61K 31/216* | (2006.01) |
| *A61K 31/26* | (2006.01) |

(52) U.S. Cl.

CPC .......... *A61K 31/277* (2013.01); *A61K 31/216* (2013.01); *A61K 31/26* (2013.01); *A61K 31/275* (2013.01); *C07C 229/34* (2013.01); *C07C 229/38* (2013.01); *C07C 255/42* (2013.01); *C07C 255/43* (2013.01)

(58) Field of Classification Search

CPC .. A61K 31/275; A61K 31/277; A61K 31/216; A61K 31/26; C07C 229/34; C07C 255/42; C07C 229/38

See application file for complete search history.

(56) References Cited

U.S. PATENT DOCUMENTS

| | | | |
|---|---|---|---|
| 3,261,859 A | 7/1966 | Dengel et al. | |
| 3,957,845 A | 5/1976 | Treiber et al. | |
| 4,115,432 A | 9/1978 | Dengel | |
| 4,438,131 A | 3/1984 | Ehrmann et al. | |
| 4,612,313 A | 9/1986 | Leinert et al. | |
| 4,833,162 A | 5/1989 | Newman | |
| 4,968,717 A | 11/1990 | Unger et al. | |
| 5,162,569 A | 11/1992 | Liang et al. | |
| 5,247,119 A | 9/1993 | Fowler et al. | |
| 5,451,604 A | 9/1995 | Mueller et al. | |
| 5,486,539 A | 1/1996 | Liang et al. | |
| 5,859,279 A | 1/1999 | Bannister et al. | |
| 5,910,601 A | 6/1999 | McCague et al. | |
| 6,057,344 A | 5/2000 | Young | |
| 6,265,439 B1 | 7/2001 | Mueller et al. | |
| 6,451,852 B2 | 9/2002 | Liang et al. | |
| 6,750,238 B1 | 6/2004 | Erhardt | |
| 7,164,027 B2 | 1/2007 | Erhardt | |
| 7,511,077 B2 | 3/2009 | Pajouhesh et al. | |
| 2001/0016602 A1 | 8/2001 | Liang et al. | |
| 2006/0235050 A1 | 10/2006 | Pajouhesh et al. | |
| 2014/0296335 A1 | 10/2014 | Maguire et al. | |
| 2016/0074354 A1 | 3/2016 | Maguire et al. | |

FOREIGN PATENT DOCUMENTS

| | | |
|---|---|---|
| CA | 986946 A1 | 4/1976 |
| DE | 2263527 A1 | 7/1973 |
| EP | 0434094 B1 | 6/1991 |
| EP | 0434095 B1 | 6/1991 |
| GB | 1090609 A | 11/1967 |
| GB | 1367677 A | 9/1974 |
| GB | 2435824 A | 9/2007 |

OTHER PUBLICATIONS

Biswas et al., "Synthesis and biological activity of carboxy verapamil, a new derivative of verapamil," *Eur J Pharmacol* 104(3-4):267-75 (1984).

Butora et al., "Some New Analogues of Verapamil and Mepamil. Synthesis and Basic Pharmacological Properties," *Coll. Czech. Chem. Commun.* 57:1967-1981 (1992).

Curtis et al., "Actions of the Verapamil Analogues, Anipamil and Ronipamil, Against Ischaemia-Induced Arrhythmias in Conscious Rats," *Br. J. Pharmac.* 88: 355-361 (1986).

Frishman et al, "Sustained-Release Verapamil Formulations for Treating Hypertension," *J. Clin. Pharmacol.* 32(5): 455-462 (1992). (Abstract Only).

Hitce et al., "Palladium-Catalyzed Intramolecular C(sp3)-H Functionalization: Catalyst Development and Synthetic Applications," *Chem. Eur. J.* 13:792-799 (2007).

Mannhold et al., "The Influence of Aromatic Substitution on the Negative Inotropic Action of Verapamil in the Isolated Cat Papillary Muscle," *Arzneim.-Forsch./Drug Res.* 31:773-780 (1981).

(Continued)

*Primary Examiner* — Shobha Kantamneni
(74) *Attorney, Agent, or Firm* — Clark & Elbing LLP

(57) ABSTRACT

The present invention relates to the use of a pharmaceutically effective amount of an short-acting calcium channel blocking compound to treat ischemic heart conditions, cardiac arrhythmias, hypertensive crisis in an emergency room setting, hypertension before, during, or after surgery, no-reflow phenomenon following reperfusion, and diseases associated with decreased skeletal muscle blood flow. The invention also relates to pharmaceutical compositions formulated for use in such methods and to kits for such methods.

4 Claims, No Drawings

(56) References Cited

OTHER PUBLICATIONS

Müller et al., "Once a Day Verapamil in Essential Hypertension," Br. J. Clin. Pharmac. 21: 143S-147S (1986).
Mulligan et al., "Dose Proportionality of Pharmacokinetics with a Cr-Verapamil Formulation," *Eur. J. Drug Metab. Pharmacokinet.* Spec. No. 3: 304-311 (1991). (Abstract Only).
Prisant, "Verapamil Revisited: A Transition in Novel Drug Delivery Systems and Outcomes," *Heart Dis.* 3(1): 55-62 (2001). (Abstract Only).
Retzinger et al., "Ionization and surface properties of verapamil and several verapamil analogues," J Pharm Sci. 75(10):976-82 (1986).
Romanelli et al., "A Search for Calcium-Channel Activators in the Verapamil Series," *Il Farmaco* 44:449-464 (1989).
English Translation of the Second Office Action for Chinese Patent Application No. 200880020979.1, mailed Mar. 25, 2013 (5 pages).
English translation of Notice of Reasons for Rejection for Japanese Patent Application No. 2010-513245, mailed Jun. 11, 2013 (3 pages).
English Translation of Office Action for Chinese Patent Application No. 200880020979.1, mailed Jul. 4, 2012 (9 pages).
International Search Report for International Application No. PCT/US2008/007665, mailed Sep. 16, 2008.
Office Action for Canadian Patent Application No. 2,693,627, dated Dec. 19, 2013 (3 pages).
Office Action for Chinese Patent Application No. 200880020979.1, mailed Jul. 4, 2012 (8 pages).
Office Action for European Patent Application No. 08786636.6-1211, dated Mar. 5, 2012 (4 pages).
Office Action for European Patent Application No. 08786636.6-1211, dated Aug. 20, 2012 (6 pages).
Patent Examination Report for Australian Patent Application No. 2008266798, Issued Nov. 7, 2012 (4 pages).
Supplementary European Search Report for European Patent Application No. EP 08 76 8636, completed Oct. 13, 2010; mailed Oct. 26, 2010.
Written Opinion for International Application No. PCT/US2008/007665, mailed Sep. 16, 2008.
Non-Final Office Action for U.S. Appl. No. 12/664,026, dated Jun. 18, 2012 (12 pages).
Final Office Action for U.S. Appl. No. 12/664,026, Dec. 19, 2012 (18 pages).
Examiner's Answer to the Appeal Brief for U.S. Appl. No. 12/664,026, dated Mar. 20, 2014 (11 pages).
Non-Final Office Action for U.S. Appl. No. 14/949,107, dated Jan. 22, 2016 (7 pages).
First Examination Report for Indian Patent Application No. 227/CHENP/2010, mailed Aug. 31, 2016 (8 pages).

SHORT ACTING PHENYLALKYLAMINE CALCIUM CHANNEL BLOCKERS AND USES THEREOF

BACKGROUND OF THE INVENTION

The invention relates to the use of phenylalkylamine compounds which block L-type calcium channels to treat cardiovascular disorders.

Calcium Channel Blockers

Calcium channel blockers (CCBs) are a chemically diverse class of compounds having important therapeutic value in the control of a variety of diseases including several cardiovascular disorders, such as hypertension, angina, and cardiac arrhythmias and include a heterogeneous group of drugs that prevent or slow the entry of calcium into cells by regulating cellular calcium channels. Calcium influx through these channels initiates a process of electromechanical coupling that ultimately leads to muscle contraction. The ability to regulate the entry of calcium into cardiac and vascular smooth muscle cells is a powerful therapeutic approach to the treatment of angina and hypertension, respectively. Likewise, blocking calcium influx into cardiac tissues and conduction systems provides a useful approach to control certain types of arrhythmia.

Serum Esterases

Serum esterases play an important role in the hydrolytic biotransformation of a vast number of structurally diverse drugs. These enzymes are major determinants of the pharmacokinetic behavior of most therapeutic agents containing ester bonds. Serum esterases are classified into three groups, A-, B-, and C-esterases, based on their interaction with organophosphates (De Vriese et al., Endocrinology (2004) 145, No. 11, 4997-5005). A-esterases, including arylesterase/paraoxonase, rapidly hydrolyze organophosphates. B-esterases, including acetylcholinesterase, butyrylcholinesterase, and nonspecific carboxylesterase, are inhibited by organophosphates. C-esterases, such as acetylesterase, do not interact with organophosphates.

Angina

Angina is a symptom of insufficient blood oxygen supply to an area of the heart due to an imbalance of the oxygen supply-demand ratio. Angina is usually precipitated following exertion or emotional stress in susceptible patients due to an inability of the coronary vasculature to provide sufficient cardiac oxygen perfusion. A narrowing of the coronary arteries is often an underlying cause as a result of arteriosclerosis or vasospastic narrowing of blood vessels. Angina usually lasts less than 15 minutes and is typically treated by sublingual administration of nitroglycerin to relieve symptoms. Nitroglycerin and other nitrates induce vasodilation through release of nitric oxide (NO) thereby causing a lowering of blood pressure.

Angina can be classified as stable angina whose principal underlying cause is arteriosclerosis, vasospastic angina (also called variant angina or Prinzmetal angina) whose underlying cause is due to transient vasospasm of the coronary arteries, or unstable angina cause by platelet clotting at sites of ruptured arteriosclerotic plaques. Stable angina usually occurs as a result of exertion or stress whereas vasospastic angina can also be felt during periods of rest or in the early morning hours. Unstable angina is felt even during periods of rest and can signal imminent myocardial infarction. Sustained reduced blood flow (ischemia) to the heart can cause permanent damage to the heart due to the death of cardiac muscle. When coronary arteries are severely narrowed by more than 50-70%, the blood vessels can no longer supply the oxygen demands of the heart and angina is felt symptomatically as chest pain.

Cardiac Arrhythmia and Atrial Fibrillation

Arrhythmia, or abnormal heart rhythms, is caused by abnormal excitation and conduction to the heart. The mechanism of the onset of arrhythmia is categorized into three groups: (1) abnormal excitation, (2) abnormal conduction of excitation, and (3) a combination of abnormal excitation and abnormal conduction of excitation.

Atrial fibrillation is arrhythmia arising from abnormalities in the intrinsic pacemaker conductive potential of the heart. In atrial fibrillation, the electrical discharges are rapid and irregular, resulting in an irregular rhythm of heart contraction. In a normal heart, electrical discharges are generated in the sino-atrial node. In atrial fibrillation, electrical discharges are not generated exclusively in the sino-atrial node and come from other parts of the atria. These rapid and irregular discharges result in rapid and ineffectual atrial contractions that reduce the ability of the atria to supply blood to the ventricles.

A recurrent arrhythmia with an abrupt onset and termination is designated as paroxysmal. Paroxysmal supraventricular tachycardia (PSVT) presents as episodes of regular and paroxysmal palpitations with sudden onset and termination (Blomstrom-Lundqvist et al., 2003, *J Am Coll Cardiol*, 42:1493-531).

Atrial flutter is characterized by acute symptoms of palpitations, dyspnea, fatigue, or chest pain. In most instances, patients with atrial flutter have a two-to-one atrio-ventricular node (AV) conduction pattern. For example, the flutter rate of the atria can be 300 per minute with a ventricular rate of 150 beats per minute (Blomstrom-Lundqvist et al., 2003, *J Am Coll Cardiol*, 42:1493-531).

Blood Flow and Pressure Regulation

Hypertension is defined as high blood pressure, usually above 140 (systolic)/90 (diastolic). Hypertensive conditions can occur in relation to the conduction of surgical procedures. For example, blood pressure control is critical before, during, and after surgery. Hypertensive crisis arising from high blood pressure is subdivided into two categories: urgent and emergency. The symptoms of an emergency hypertensive crisis are more severe and may include brain swelling, stroke, pulmonary edema, heart attack or other symptoms. Both urgent and emergency categories hypertensive crisis involve a severe increase in blood pressure and require immediate treatment to prevent potential complications (i.e., stroke or damage to organs and tissues).

Raynaud's phenomenon is a disorder associated with restricted blood flow to body extremities such as the fingers, toes, ears and nose, and reflects an aberration of the normal response to cold involving peripheral vasoconstriction and restriction of blood flow to the extremities in order to protect the core body temperature. Attacks may be brought on by exposure to cold or emotional stress. Up to 5 to 10% of the population of the United States is affected, to some degree, by Raynaud's phenomenon.

Intermittent claudication is a condition that involves discomfort in the legs and occasionally the arms. It is due to a narrowing of the arteries and a resulting decrease in blood flow, particularly to muscles during physical exertion. The condition most commonly occurs in the calf muscle but may also affect the foot, hip or buttocks.

No-reflow phenomenon is a condition following reperfusion in which excessive or abnormal vasoconstriction occurs. The no-reflow phenomenon that occurs in about 2-5% of patients undergoing percutaneous transluminal coronary angioplasty (PTCA) is believed to be due to aggregation of platelets and neutrophils, which causes a blockage of blood flow within the vessels and vasoconstriction from substances released from the platelets. The condition is characterized by abnormal tissue perfusion. Persistent no-reflow is associated with higher clinical complication rates (Eeckhout, E. and Kern, M. J., *European Heart Journal* (2001) 22, 729-739).

Given the prevalence of cardiovascular disorders in patients, there is a need for new and improved compound and methods for treating cardiovascular disorders including ischemic heart conditions and cardiac arrhythmias.

SUMMARY OF THE INVENTION

The invention relates to the use of a pharmaceutically effective amount of a short-acting calcium channel blocking compounds for use in treating ischemic heart conditions such as angina pectoris and cardiac arrythmias such as paroxysmal supraventricular tachycardia, atrial flutter and atrial fibrillation in humans. The compounds may also be used to treat other cardiovascular disorders and conditions involving hypertension and blood flow.

Accordingly, the first aspect of the invention features a method of treating an ischemic heart condition or cardiac arrhythmia, where the method includes administering to a patient in need thereof a therapeutically effective amount of a compound having the formula

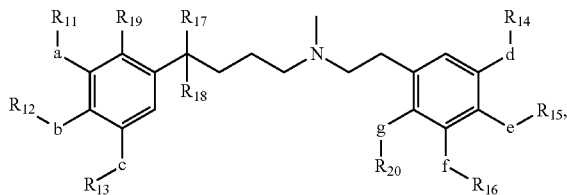

or a pharmaceutically acceptable addition salt thereof, or any enantiomer or diastereomer thereof, where
  each a, b, c, d, e, f, and g is, independently, —CH$_2$—, —O—, —S—, or a single bond;
  each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or CO$_2$R$_{10}$;
  each $R_{10}$ is, independently, H, optionally substituted lower alkyl, or optionally substituted lower alkoxyalkyl;
  $R_{18}$ is H, CN, or CO$_2$R$_{10}$; and
  $R_{19}$ is CH$_3$, H, or halogen.
In a preferred embodiment of the invention,
  each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —CO$_2$(lower alkyl), lower alkyl substituted with —CO$_2$(lower alkoxyalkyl), lower alkyl substituted with fluorine or chlorine, lower alkoxyalkyl, lower alkoxyalkyl substituted with —CO$_2$(lower alkyl), lower alkoxyalkyl substituted with —CO$_2$(lower alkoxyalkyl), lower alkoxyalkyl substituted with fluorine or chlorine, or CO$_2$R$_{10}$; and
  each $R_{10}$ is, independently, lower alkyl or lower alkoxyalkyl.
In some embodiments of the invention, the ischemic heart condition is stable or unstable angina or vasospastic angina. In other embodiments of the invention, the cardiac arrhythmia is atrial fibrillation, atrial flutter, paroxysmal supraventricular tachycardia (PSVT), premature atrial, nodal, or ventricular depolarizations, atrial tachycardia, ventricular tachycardia, ventricular fibrillation, or Torsades de Pointes.

In certain embodiments, administering includes sublingual, buccal, transdermal, intranasal or inhalation administration and the patient desirably is a human patient.

In a second aspect, the invention features a method of treating a hypertensive crisis in an emergency room setting, where the method includes administering to a patient in need thereof a therapeutically effective amount of a compound having the formula

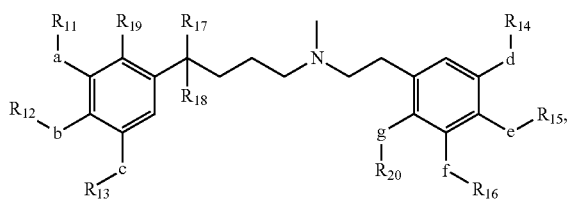

or a pharmaceutically acceptable addition salt thereof, or any enantiomer or diastereomer thereof, where
  each a, b, c, d, e, f, and g is, independently, —CH$_2$—, —O—, —S—, or a single bond;
  each $R_{10}$ is, independently, H, optionally substituted lower alkyl, or optionally substituted lower alkoxyalkyl;
  each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or CO$_2$R$_{10}$;
  $R_{18}$ is H, CN, or CO$_2$R$_{10}$; and
  $R_{19}$ is CH$_3$, H, or halogen.
In a preferred embodiment of the invention,
  each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —CO$_2$(lower alkyl), lower alkyl substituted with —CO$_2$(lower alkoxyalkyl), lower alkyl substituted with fluorine or chlorine, lower alkoxyalkyl, lower alkoxyalkyl substituted with —CO$_2$(lower alkyl), lower alkoxyalkyl substituted with —CO$_2$(lower alkoxyalkyl), lower alkoxyalkyl substituted with fluorine or chlorine, or CO$_2$R$_{10}$; and
  each $R_{10}$ is, independently, lower alkyl or lower alkoxyalkyl.
In some embodiments of the invention, administering includes sublingual, buccal, intranasal, inhalation, or parenteral administration. In certain embodiments of the invention, parenteral administration is intravenous administration. In still other embodiments, the patient is a human patient.

In a third aspect, the invention features a method of treating hypertension before, during, or after surgery, or no-reflow phenomenon following reperfusion, where the method includes administering to a patient in need thereof a therapeutically effective amount of a compound having the formula

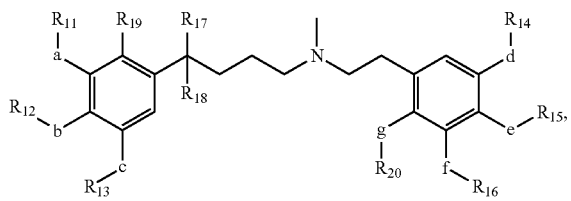

or a pharmaceutically acceptable addition salt thereof, or any enantiomer or diastereomer thereof, where each a, b, c, d, e, f, and g is, independently, —$CH_2$—, —O—, —S—, or a single bond;

each $R_{10}$ is, independently, H, optionally substituted lower alkyl, or optionally substituted lower alkoxyalkyl;

each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or $CO_2R_{10}$;

$R_{18}$ is H, CN, or $CO_2R_{10}$; and $R_{19}$ is $CH_3$, H, or halogen.

In a preferred embodiment of the invention, each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —$CO_2$(lower alkyl), lower alkyl substituted with —$CO_2$(lower alkoxyalkyl), lower alkyl substituted with fluorine or chlorine, lower alkoxyalkyl, lower alkoxyalkyl substituted with —$CO_2$(lower alkyl), lower alkoxyalkyl substituted with —$CO_2$(lower alkoxyalkyl), lower alkoxyalkyl substituted with fluorine or chlorine, or $CO_2R_{10}$; and each $R_{10}$ is, independently, lower alkyl or lower alkoxyalkyl.

In some embodiments of the invention, administering involves parenteral administration. In select embodiments, the parenteral administration is intravenous administration. In other embodiments of the invention, the patient is a human patient.

The fourth aspect of the invention features another method of treating a disease associated with decreased skeletal muscle blood flow where the method includes administering to a patient in need thereof a therapeutically effective amount of a compound having the formula

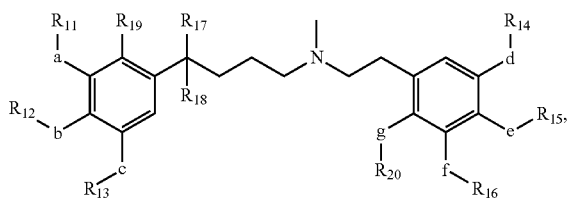

or a pharmaceutically acceptable addition salt thereof, or any enantiomer or diastereomer thereof, where each a, b, c, d, e, f, and g is, independently, —$CH_2$—, —O—, —S—, or a single bond;

each $R_{10}$ is, independently, H, optionally substituted lower alkyl, or optionally substituted lower alkoxyalkyl;

each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or $CO_2R_{10}$;

$R_{18}$ is H, CN, or $CO_2R_{10}$; and $R_{19}$ is $CH_3$, H, or halogen.

In a preferred embodiment of the invention, each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —$CO_2$(lower alkyl), lower alkyl substituted with —$CO_2$(lower alkoxyalkyl), lower alkyl substituted with fluorine or chlorine, lower alkoxyalkyl, lower alkoxyalkyl substituted with —$CO_2$(lower alkyl), lower alkoxyalkyl substituted with —$CO_2$(lower alkoxyalkyl), lower alkoxyalkyl substituted with fluorine or chlorine, or $CO_2R_{10}$; and each $R_{10}$ is, independently, lower alkyl or lower alkoxyalkyl.

In some embodiments, the disease associated with decreased skeletal muscle blood flow is Raynaud's phenomenon or intermittent claudication. In other embodiments, administering includes sublingual, buccal, transdermal, intranasal, inhalation or topical administration.

In a fifth aspect, the invention features a pharmaceutical composition including a compound having the following structure:

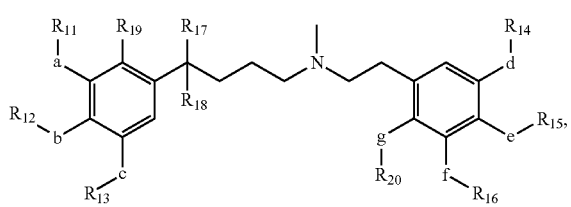

or a pharmaceutically acceptable addition salt thereof, or any enantiomer or diastereomer thereof, where each a, b, c, d, e, f, and g is, independently, —$CH_2$—, —O—, —S—, or a single bond;

each $R_{10}$ is, independently, H, optionally substituted lower alkyl, or optionally substituted lower alkoxyalkyl;

each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or $CO_2R_{10}$;

$R_{18}$ is H, CN, or $CO_2R_{10}$; and $R_{19}$ is $CH_3$, H, or halogen.

In a preferred embodiment of the invention, each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —$CO_2$(lower alkyl), lower alkyl substituted with —$CO_2$(lower alkoxyalkyl), lower alkyl substituted with fluorine or chlorine, lower alkoxyalkyl, lower alkoxyalkyl substituted with —$CO_2$(lower alkyl), lower alkoxyalkyl substituted with —$CO_2$(lower alkoxyalkyl), lower alkoxyalkyl substituted with fluorine or chlorine, or $CO_2R_{10}$; and each $R_{10}$ is, independently, lower alkyl or lower alkoxyalkyl.

In some embodiments, the pharmaceutical composition is formulated for treating a condition selected from the group consisting of:

ischemic heart conditions;

cardiac arrhythmia;

hypertensive crisis in an emergency room setting;

hypertension before, during, or after surgery;

no-reflow phenomenon following reperfusion; and a disease associated with decreased skeletal muscle flow.

In a sixth aspect, the invention features a kit including (a) a pharmaceutical composition that includes a compound having the following structure:

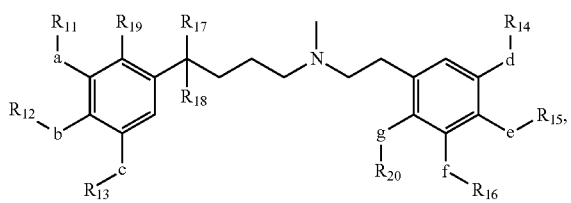

or a pharmaceutically acceptable addition salt thereof, or any enantiomer or diastereomer thereof, where each a, b, c, d, e, f, and g is, independently, —$CH_2$—, —O—, —S—, or a single bond;

each $R_{10}$ is, independently, H, optionally substituted lower alkyl, or optionally substituted lower alkoxyalkyl;

each $R_{11}$, $R_{12}$, $R_{13}$, $R_{14}$, $R_{15}$, $R_{16}$, $R_{17}$, and $R_{20}$ is, independently, H, halogen, optionally substituted lower alkyl, optionally substituted lower alkoxyalkyl, or $CO_2R_{10}$;

$R_{18}$ is H, CN, or $CO_2R_{10}$; and $R_{19}$ is $CH_3$, H, or halogen; and (b) instructions for using the pharmaceutical composition of (a) for the treatment of a condition selected from the group consisting of:

ischemic heart conditions;
cardiac arrhythmia;
hypertensive crisis in an emergency room setting;
hypertension before, during, or after surgery;
no-reflow phenomenon following reperfusion; and
a disease associated with decreased skeletal muscle flow.

In a preferred embodiment of the invention, each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —$CO_2$(lower alkyl), lower alkyl substituted with —$CO_2$(lower alkoxyalkyl), lower alkyl substituted with fluorine or chlorine, lower alkoxyalkyl, lower alkoxyalkyl substituted with —$CO_2$(lower alkyl), lower alkoxyalkyl substituted with —$CO_2$(lower alkoxyalkyl), lower alkoxyalkyl substituted with fluorine or chlorine, or $CO_2R_{10}$; and each $R_{10}$ is, independently, lower alkyl or lower alkoxyalkyl.

In any of the methods, compositions, or kits of the invention, the compound used in the invention can exclude any of the following compounds:

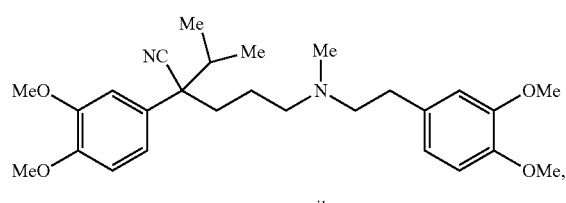
verapamil

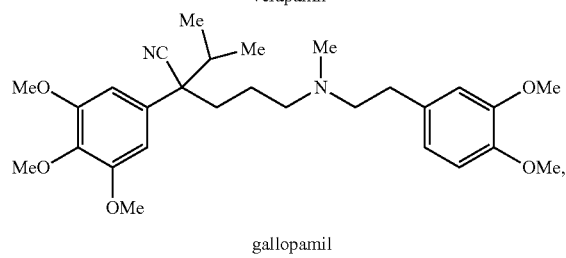
gallopamil

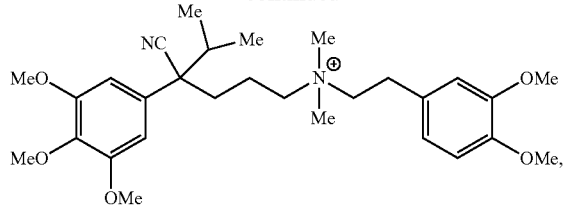
D-890

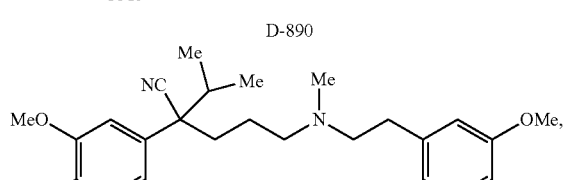
devapamil (D888)

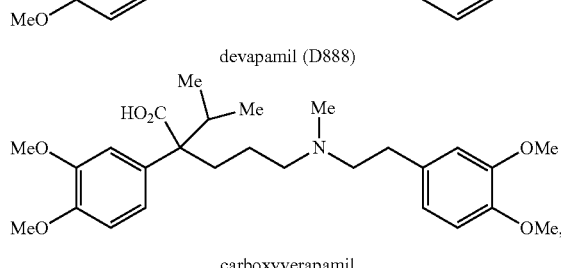
carboxyverapamil

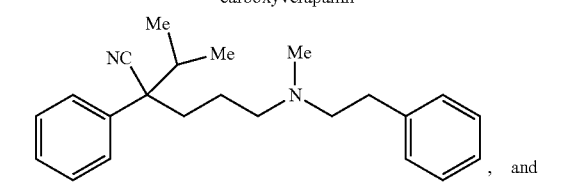
emopamil, and

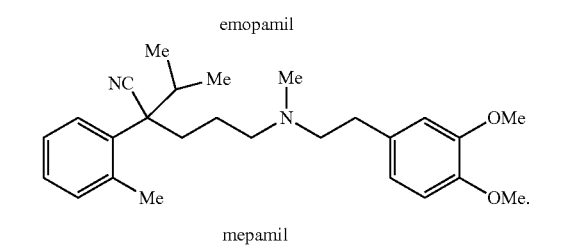
mepamil.

In any of the methods, compositions, or kits of the invention, the compound used in the invention may be stereochemically pure or may be used as a mixture of stereochemical isomers. In some embodiments, the compound is racemic. In other embodiments, the compound is a single enantiomer or a single diastereomer. In still other embodiments, the compound is a mixture of diastereomers or a mixture of enantiomers.

In any of the methods, compositions, or kits of the invention, preferred embodiments include a compound where:

each a, b, c, d, e, f, and g is, independently, —$CH_2$—, —O—, —S—, or a single bond;

each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —$CO_2$(lower alkyl), lower alkyl substituted with —$CO_2$(lower alkoxyalkyl), lower alkyl substituted with fluorine or chlorine, lower alkoxyalkyl, lower alkoxyalkyl substituted with —$CO_2$(lower alkyl), lower alkoxyalkyl substituted with —$CO_2$(lower alkoxyalkyl), lower alkoxyalkyl substituted with fluorine or chlorine, or $CO_2R_{10}$;

each $R_{10}$ is, independently, lower alkyl or lower alkoxyalkyl;

$R_{18}$ is H, CN, or $CO_2R_{10}$; and
$R_{19}$ is $CH_3$ or H;
where the compound is not verapamil, gallopamil, emopamil, mepamil, or devapamil.

In any of the methods, compositions, or kits of the invention, some embodiments include a compound where at least one of $R_{11}$, $R_{12}$, $R_{13}$, $R_{14}$, $R_{15}$, $R_{16}$, $R_{17}$, $R_{18}$, and $R_{20}$ is $CO_2R_{10}$, lower alkyl substituted by —$CO_2$(lower alkyl), lower alkyl substituted with —$CO_2$(lower alkoxyalkyl), a lower alkoxyalkyl substituted with —$CO_2$(lower alkyl), or lower alkoxyalkyl substituted with —$CO_2$(lower alkoxyalkyl). In further embodiments, $R_{19}$ is H, g is a single bond, and $R_{20}$ is H. In still other embodiments, $R_{19}$ is H, g is a single bond, $R_{20}$ is $CO_2R_{10}$, and -d-$R_{14}$ and -e-$R_{15}$ are not both —O-(lower alkyl) or —O-(lower alkoxyalkyl).

In any of the methods, compositions, or kits of the invention, some embodiments include a compound where
(a) $R_{17}$ is lower alkyl;
(b) $R_{18}$ is CN or $CO_2R_{10}$;
(c) at least one of -a-$R_{11}$, -b-$R_{12}$, or -c-$R_{13}$ is, independently
  (i) —O-(lower alkyl);
  (ii) —O-(lower alkyl substituted with —$CO_2$(lower alkyl));
  (iii) —O-(lower alkyl substituted with —$CO_2$(lower alkoxyalkyl));
  (iv) —O-(lower alkyl substituted with fluorine or chlorine);
  (v) —O-(lower alkoxyalkyl);
  (vi) —O-(lower alkoxyalkyl substituted with —$CO_2$(lower alkyl));
  (vii) —O-(lower alkoxyalkyl substituted with —$CO_2$(lower alkoxyalkyl));
  (viii) —O-(lower alkyl substituted with fluorine or chlorine); or
  (ix) -(single bond)-$CO_2R_{10}$; and
(d) at least one of -d-$R_{14}$, -e-$R_{15}$, -f-$R_{16}$, or -g-$R_{20}$ is, independently,
  (i) —O-(lower alkyl);
  (ii) —O-(lower alkyl substituted with —$CO_2$(lower alkyl));
  (iii) —O-(lower alkyl substituted with —$CO_2$(lower alkoxyalkyl));
  (iv) —O-(lower alkyl substituted with fluorine or chlorine);
  (v) —O-(lower alkoxyalkyl);
  (vi) —O-(lower alkoxyalkyl substituted with —$CO_2$(lower alkyl));
  (vii) —O-(lower alkoxyalkyl substituted with —$CO_2$(lower alkoxyalkyl));
  (viii) —O-(lower alkyl substituted with fluorine or chlorine); or
  (ix) -(single bond)-$CO_2R_{10}$.

In further embodiments, at least one of $R_{11}$, $R_{12}$, $R_{13}$, $R_{14}$, $R_{15}$, $R_{16}$, $R_{17}$, $R_{18}$, or $R_{20}$ is $CO_2R_{10}$, lower alkyl substituted by —$CO_2$(lower alkyl), lower alkyl substituted with —$CO_2$(lower alkoxyalkyl), lower alkoxyalkyl substituted with —$CO_2$(lower alkyl), or lower alkoxyalkyl substituted with —$CO_2$(lower alkoxyalkyl). In further embodiments, $R_{19}$ is H, g is a single bond, and $R_{20}$ is H. In still other embodiments, g is a single bond, $R_{20}$ is $CO_2R_{10}$, and -d-$R_{14}$ and -e-$R_{15}$ are not both —O-(lower alkyl) or —O-(lower alkoxyalkyl).

In any of the methods, compositions, or kits of the invention, a lower alkyl may be: methyl, ethyl, propyl, isopropyl, n-butyl, s-butyl, i-butyl, t-butyl, pentyl, isoamyl, hexyl, heptyl, cyclopropyl, cyclobutyl, cyclopentyl, cyclohexyl, cyclobutylmethyl, or cycloheptyl. In some embodiments, a lower alkyl is methyl, ethyl, propyl, isopropyl, n-butyl, t-butyl, or cyclopropyl.

In any of the methods, compositions, or kits of the invention, a lower alkyl substituted with —$CO_2$(lower alkyl) may be: —$CH_2CO_2R_{21}$, —$CH_2CH_2CO_2R_{21}$, —$CH(CO_2R_{21})CH_3$, —$CH_2CH_2CH_2CO_2R_{21}$, —$CH(CO_2R_{21})CH_2CH_3$, —$CH_2CH(CO_2R_{21})CH_3$, —$CH(CH_3)CH_2CO_2R_{21}$, —$C(CH_3)_2CO_2R_{21}$, —$CH_2CH_2CH_2CH_2CO_2R_{21}$, —$CH_2CH_2CH_2CH_2CH_2CO_2R_{21}$, —$CH_2CH_2CH_2CH_2CH_2CH_2CO_2R_{21}$, or —$CH_2CH_2CH_2CH_2CH_2CH_2CH_2CO_2R_{21}$, where $R_{21}$ is a lower alkyl. In some embodiments, $R_{21}$ is methyl, ethyl, propyl, isopropyl, t-butyl, or cyclopropyl. In other embodiments, a lower alkyl substituted with —$CO_2$(lower alkyl) is: —$CH_2CO_2CH_3$, —$CH_2CO_2CH_2CH_3$, —$CH_2CH_2CO_2CH_3$, or —$CH_2CH_2CO_2CH_2CH_3$.

In any of the methods, compositions, or kits of the invention, a lower alkoxyalkyl may be: —$CH_2OR_{22}$, —$CH_2CH_2OR_{22}$, —$CH(OR_{22})CH_3$, —$CH_2CH_2CH_2OR_{22}$, —$CH(OR_{22})CH_2CH_3$, —$CH_2CH(OR_{22})CH_3$, —$CH(CH_3)CH_2OR_{22}$, —$C(CH_3)_2OR_{22}$, —$CH_2CH_2CH_2CH_2COR_{22}$, —$CH_2CH_2CH_2CH_2OR_{22}$, —$CH_2CH_2CH_2CH_2CH_2OR_{22}$, or —$CH_2CH_2CH_2CH_2CH_2CH_2CH(OR_{22})$, where $R_{22}$ is a lower alkyl. In some embodiments, $R_{22}$ is methyl, ethyl, propyl, isopropyl, n-butyl, t-butyl, or cyclopropyl. In other embodiments, a lower alkoxyalkyl is —$CH_2OCH_3$, —$CH_2OCH_2CH_3$, —$CH_2CH_2OCH_3$, or —$CH_2CH_2OCH_2CH_3$.

In any of the methods, compositions, or kits of the invention, a lower alkyl substituted with —$CO_2$(lower alkoxyalkyl) may be: —$CH_2CO_2R_{23}$, —$CH_2CH_2CO_2R_{23}$, —$CH(CO_2R_{23})CH_3$, —$CH_2CH_2CH_2CO_2R_{23}$, —$CH(CO_2R_{23})CH_2CH_3$, —$CH_2CH(CO_2R_{23})CH_3$, —$CH(CH_3)CH_2CO_2R_{23}$, —$C(CH_3)_2CO_2R_{23}$, —$CH_2CH_2CH_2CH_2CO_2R_{23}$, —$CH_2CH_2CH_2CH_2CH_2CO_2R_{23}$, —$CH_2CH_2CH_2CH_2CH_2CH_2CO_2R_{23}$, or —$CH_2CH_2CH_2CH_2CH_2CH_2CH_2(CO_2R_{23})$, where $R_{23}$ is a lower alkoxyalkyl. In some embodiments, $R_{23}$ is $CH_2CH_2OCH_3$ or $CH_2CH_2OCH_2CH_3$. In other embodiments, a lower alkyl substituted with —$CO_2$(lower alkoxyalkyl) is: —$CH_2CO_2(CH_2CH_2OCH_3)$, —$CH_2CO_2(CH_2CH_2OCH_2CH_3)$, —$CH_2CH_2CO_2(CH_2CH_2OCH_3)$, or —$CH_2CH_2CO_2(CH_2CH_2OCH_2CH_3)$.

In any of the methods, compositions, or kits of the invention, a lower alkyl substituted with fluorine or chlorine may be: —$CH_2X$, —$CHX_2$, —$CX_3$, —$CH_2CX_3$, —$CX_2CX_3$, or —$CH(CX_3)_2$, where X is —F or —Cl. In some embodiments, a lower alkyl substituted with fluorine or chlorine is —$CF_3$, —$CCl_3$, —$CF_2CF_3$, or —$CH(CF_3)_2$.

In any of the methods, compositions, or kits of the invention, a lower alkoxyalkyl substituted with —$CO_2$(lower alkyl) may be: —$CH_2CH(CO_2R_{24})OR_{25}$, —$CH(CO_2R_{24})CH_2OR_{25}$, —$CH_2CH_2OCH_2CH_2(CO_2R_{24})$, or —$CH_2CH_2OCH(CO_2R_{24})CH_3$, where $R_{24}$ and $R_{25}$ are each, independently, lower alkyl. In some embodiments, $R_{24}$ is methyl, ethyl, propyl, isopropyl, t-butyl, or cyclopropyl. In some embodiments, $R_{25}$ is methyl, ethyl, propyl, isopropyl, n-butyl, t-butyl, or cyclopropyl.

In any of the methods, compositions, or kits of the invention, a lower alkoxyalkyl substituted with —$CO_2$(lower alkoxyalkyl) may be: —$CH_2CH(CO_2R_{26})OR_{27}$, —$CH(CO_2R_{26})CH_2OR_{27}$, —$CH_2CH_2OCH_2CH_2(CO_2R_{26})$, or —$CH_2CH_2OCH(CO_2R_{26})CH_3$, where, independently, $R_{26}$ is a lower alkoxyalkyl and $R_{27}$ is a lower alkyl. In some embodiments, $R_{26}$ is $CH_2CH_2OCH_3$ or $CH_2CH_2OCH_2CH_3$. In some embodiments, $R_{27}$ is methyl, ethyl, propyl, isopropyl, n-butyl, t-butyl, or cyclopropyl.

In any of the methods, compositions, or kits of the invention, a lower alkoxyalkyl substituted with fluorine or chlorine may be: —$CX_2CX_2OCH_2CH_3$, —$CH_2CH_2OCH_2CX_3$, —$CH_2CH_2OCX_2CX_3$, or —$CH_2CH_2OCH(CX_3)_2$, where X is —F or —Cl.

In any of the methods, compositions, or kits of the invention, $CO_2R_{10}$ may be: $CO_2CH_3$, $CO_2CH_2CH_3$, $CO_2CH(CH_3)_2$, $CO_2C(CH_3)_3$, $CO_2CH_2CH_2OCH_3$, or $CO_2CH_2CH_2OCH_2CH_3$.

In any of the methods, compositions, or kits of the invention, the compound used in the invention desirably is any of the following compounds:

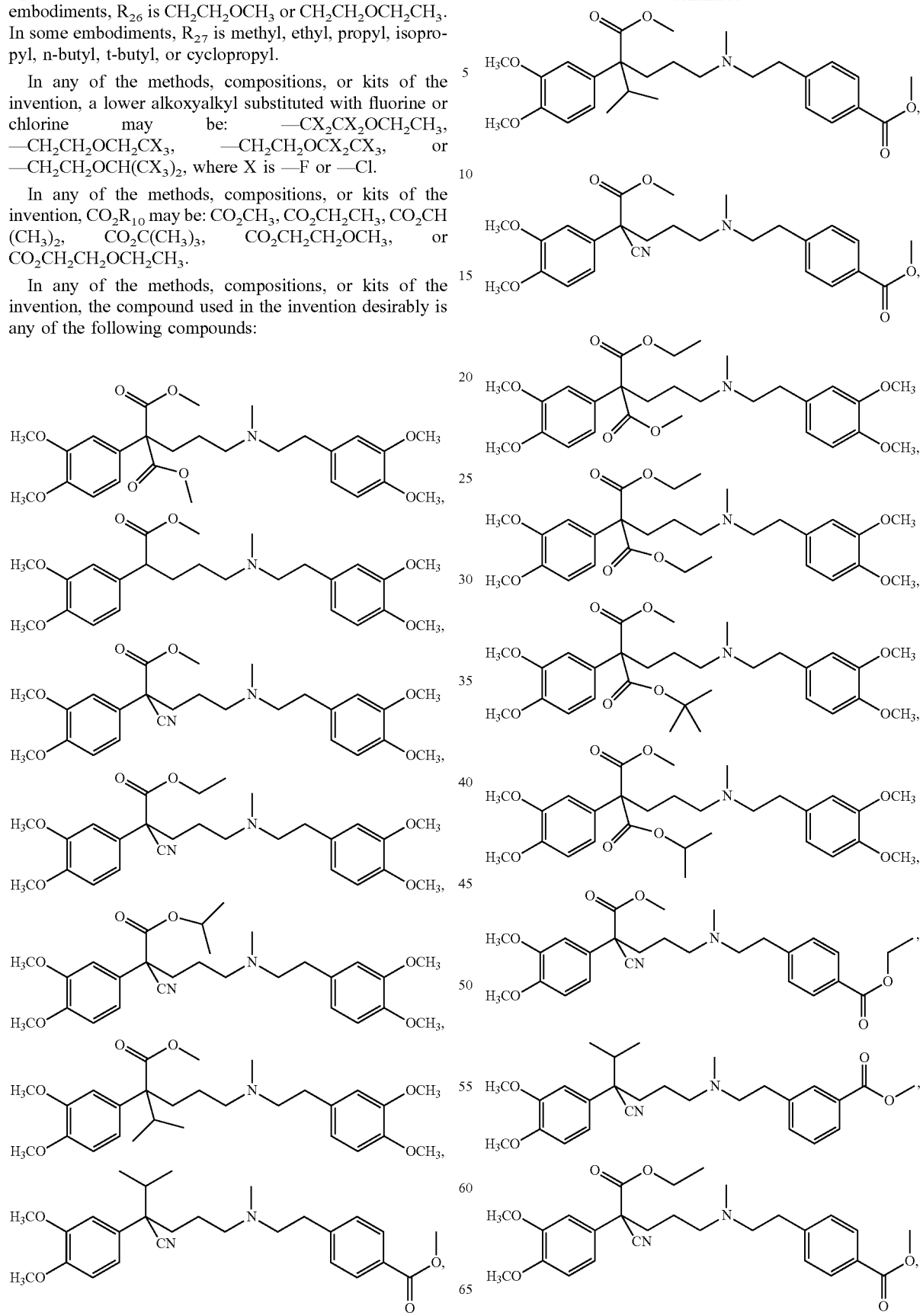

13
-continued
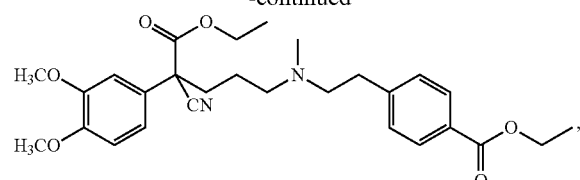
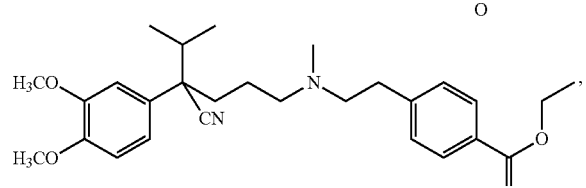
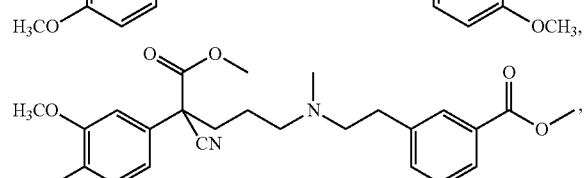
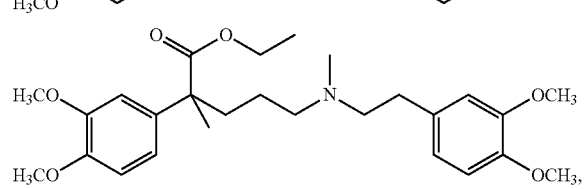
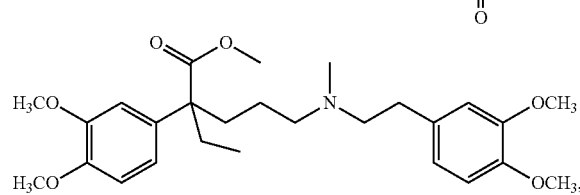
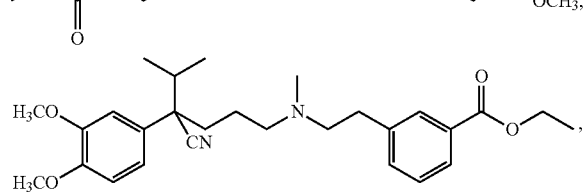
14
-continued
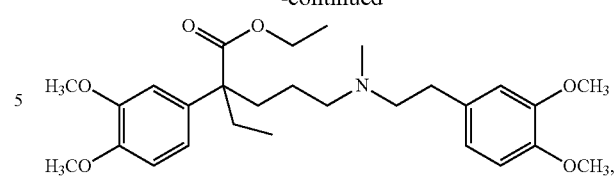
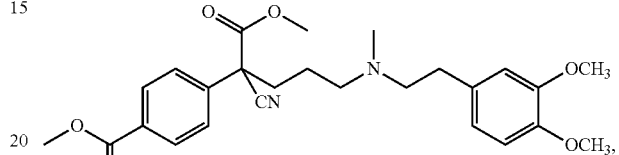
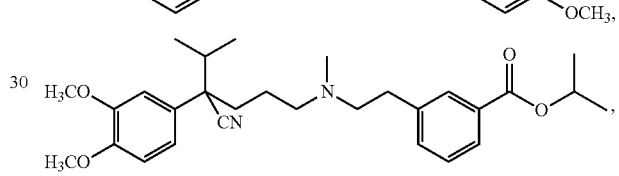
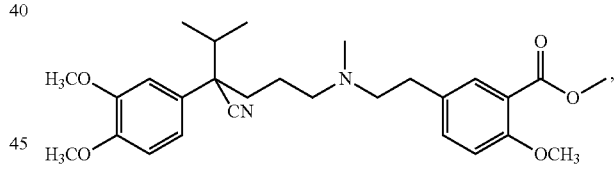
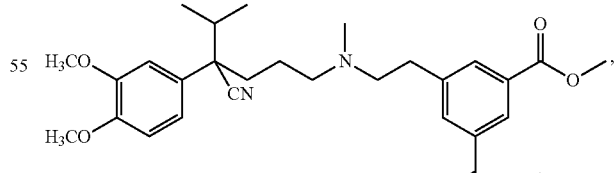
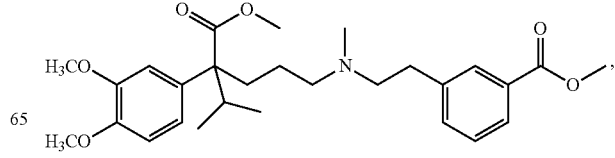

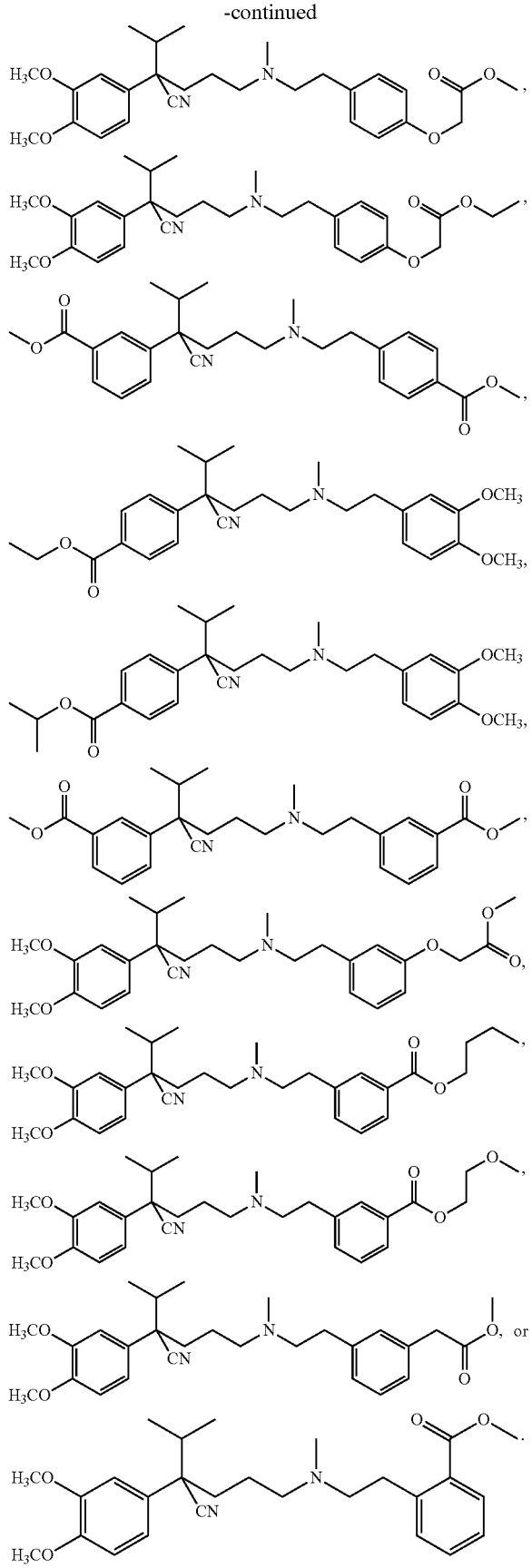

Definitions

The term "angina" as used herein refers to the chest discomfort felt due to ischemic heart disease. Angina can be classified as stable angina whose principal underlying cause is arteriosclerosis, vasospastic angina (also called variant angina or Prinzmetal angina) whose underlying cause is due to transient vasospasm of the coronary arteries, or unstable angina cause by platelet clotting at sites of ruptured arteriosclerotic plaques.

As used herein, the term "buccal administration" means absorption of a compound or a pharmaceutically acceptable formulation of a compound by administering between the cheek and gum. Desirably the compound is a compound of Formula I.

"Cardiac arrhythmia" as used herein, refers to a condition characterized by abnormal heart rhythms that are irregular, too fast, too slow, or conducted via an abnormal electrical pathway through the heart. Arrhythmias can be divided into ventricular arrhythmias occurring in the lower chambers of the heart (ventricles) and into supraventricular arrhythmias occurring in the upper chambers of the heart (aorta). Cardiac arrhythmias include atrial fibrillation and atrial flutter that are characterized by abnormally fast electrical discharge patterns that cause the atria to contract very rapidly thereby impairing efficient pumping of the blood into the ventricles. Cardiac arrhythmias also include paroxysmal supraventricular tachycardia (PSVT) that is characterized by a regular and fast heart rate originating in heart tissue above the ventricles. Other exemplary cardiac arrhythmias are premature atrial, nodal, or ventricular depolarization, atrial tachycardia, ventricular tachycardia, ventricular fibrillation, and Torsades de Pointes.

A "disease associated with decreased skeletal muscle blood flow" as used herein refers to a condition where a narrowing of the arteries that perfuse the skeletal muscle results in reduced perfusion and oxygen delivery. Such conditions include, but are not limited to, Raynaud's phenomenon and intermittent claudication.

The term "excipient" is used herein to describe any ingredient other than an active compound (e.g., those having Formula I) described herein. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

"Hypertension before, during or after surgery" as used herein refers to perioperative hypertension, i.e., a sustained elevated blood pressure (systolic/diastolic ≥140/90 mm Hg in the USA, or ≥160/95 mm Hg in many other countries) that occurs immediately prior to, during, or after a surgical procedure.

The term "hypertensive crisis in an emergency room setting" as used herein refers to a sudden increase in systolic and diastolic blood pressures that requires immediate management in a hospital or hospital emergency room environment. The sudden acute and severe increase in blood pressure may or may not be associated with acute end-organ damage (i.e. cardiovascular, renal, central nervous system).

"Inhalation administration" or "administration by inhalation" as used herein refers to delivering a drug for absorption to the body in the form of a liquid aerosol mist, solid aerosol particulates or a gaseous substance by inhalation into the lungs. Desirably the compound is a compound of Formula I.

As used herein, the term "intranasal administration" or "nasal administration" means absorption of a compound or a pharmaceutically acceptable formulation of a compound by administering to the nose or nasal cavity. Desirably the compound is a compound of Formula I.

As used herein, the term "intravenous administration" means injection of a pharmaceutically acceptable formulation of a compound directly into a vein. Desirably the compound is a compound of Formula I.

The term "ischemic heart disease" or "ischemic heart condition" as used herein refers to a condition characterized by narrowed heart arteries that results in restricted blood flow and reduced oxygen delivery to the heart muscle.

The term "lower alkoxyalkyl" as used herein means a lower alkyl group having an ether-containing substituent such as, for example, ethoxyethyl, methoxyethyl, and methoxypropyl, among others, where the ether-containing substituent may be at any position of the lower alkyl. A lower alkoxyalkyl may be, for example: $-CH_2OR_{22}$, $-CH_2CH_2OR_{22}$, $-CH(OR_{22})CH_3$, $-CH_2CH_2CH_2OR_{22}$, $-CH(OR_{22})CH_2CH_3$, $-CH_2CH(OR_{22})CH_3$, $-CH(CH_3)CH_2OR_{22}$, $-C(CH_3)_2OR_{22}$, $-CH_2CH_2CH_2COR_{22}$, $-CH_2CH_2CH_2CH_2OR_{22}$, $-CH_2CH_2CH_2CH_2CH_2OR_{22}$, or $-CH_2CH_2CH_2CH_2CH_2CH_2CH_2CH(OR_{22})$, where $R_{22}$ is a lower alkyl. Desirably, $R_{22}$ is methyl, ethyl, propyl, isopropyl, n-butyl, t-butyl, or cyclopropyl. Exemplary, non-limiting lower alkoxyalkyls include $-CH_2OCH_3$, $-CH_2OCH_2CH_3$, $-CH_2CH_2OCH_3$, and $-CH_2CH_2OCH_2CH_3$. A lower alkoxyalkyl may be optionally substituted. A substituted lower alkoxyalkyl may be optionally substituted, for example, with $CO_2R_{10}$ at any carbon position on either the lower alkyl group or at any carbon position on the ether containing substituent.

The term "lower alkyl" as used herein means alkyl groups of from 1 to 7 carbon atoms that consist of a straight, branched or cyclic configuration. Lower alkyls may include 1, 2, 3, 4, 5, 6, or 7 carbon atoms. Examples of lower alkyl groups include, but are not limited to: methyl, ethyl, propyl, isopropyl, butyl, s-, i- and t-butyl, pentyl, isoamyl, hexyl, heptyl, cyclopropyl, cyclobutyl, cyclopentyl, cyclohexyl, cyclobutylmethyl, and cycloheptyl, among others. Desirably, a lower alkyl is methyl, ethyl, propyl, isopropyl, n-butyl, t-butyl, or cyclopropyl. A lower alkyl may be optionally substituted. A substituted lower alkyl may be optionally substituted with, for example, $CO_2R_{10}$ at any carbon position.

"No-reflow phenomenon following reperfusion" as used herein refers to the inability of myocardial tissue to reperfuse after prolonged ischemia despite reopening of the occluded artery related to the ischemic condition.

As used herein "parenteral administration" means administration of a compound or a pharmaceutically acceptable formulation of a compound by a route that bypasses the gastrointestinal tract. Desirably parenteral administration is intravenous administration, injection of a pharmaceutically acceptable formulation of a compound below the skin's cutaneous layer (subcutaneous), within the dermis (intradermal), or into the muscle (intramuscular). Desirably the compound is a compound of Formula I.

As used herein a "pharmaceutically acceptable acid addition salt" is derived from a basic active compound and an organic acid or an inorganic acid. Exemplary pharmaceutically acceptable acid addition salts derived from organic acids include, but are not limited to, acetate, adipate, alginate, ascorbate, aspartate, benzenesulfonate, benzoate, butyrate, camphorate, camphorsulfonate, citrate, cyclopentanepropionate, digluconate, dodecylsulfate, ethanesulfonate, fumarate, glucoheptonate, glycerophosphate, heptonate, hexanoate, 2-hydroxy-ethanesulfonate, isethionate, lactobionate, lactate, laurate, lauryl sulfate, malate, maleate, malonate, methanesulfonate (mesylate), 2-naphthalenesulfonate, nicotinate, oleate, oxalate, palmitate, pamoate, pectinate, persulfate, 3-phenylpropionate, picrate, pivalate, propionate, stearate, succinate, tartrate, thiocyanate, toluenesulfonate, undecanoate, and valerate salts, and the like. Exemplary pharmaceutically acceptable acid addition salts derived from inorganic acids include bisulfate, sulfate, borate, hydrobromide, hydrochloride, hydroiodide, hemisulfate, nitrate, phosphate salts and the like. Desirably, a "pharmaceutically acceptable acid addition salt" is oxalate, hydrochloride, hydrobromide, methanesulfonate, sulfate, hemisulfate or bisulfate.

A "pharmaceutically acceptable carrier" as used herein refers to a vehicle capable of suspending or dissolving the active compound, and having the properties of being non-toxic and non-inflammatory in a patient. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the patient.

The term "pharmaceutically acceptable formulation" as used herein refers to a composition including a pharmaceutically acceptable carrier and an active compound. Desirably the active compound is a compound of Formula I.

As used herein, the term "pharmaceutical patch" refers to a pad containing an embedded active compound to be placed on the exterior surface of a patient for absorption of the active compound into the bloodstream, skin or underlying tissue. Desirably, patch is placed on the skin and the compound is released gradually from the patch over time. Further, the patch desirably is an adhesive patch.

As used herein, the term "sublingual administration" means absorption of a compound or a pharmaceutically acceptable formulation of a compound by administering under the tongue. Desirably the compound is a compound of Formula I.

As used herein, the term "therapeutically effective amount" refers to an amount of an active compound that, when administered to a patient, reduces, eliminates or prevents an ischemic heart condition, cardiac arrhythmia, hypertensive crisis in an emergency room setting, hypertension before, during or after surgery, no-reflow phenomenon following reperfusion, or a disease associated with decreased skeletal muscle bloodflow. Desirably, a therapeutically effective amount of a pharmaceutical formulation contains a compound of the invention (e.g., a compound having Formula I) in a concentration range of about 0.000001 to 10 percent weight/volume ("% w/v").

"Topical administration" or "topically administering" as used herein refers to the application of a pharmaceutical acceptable formulation of a compound to the external surface of a patient, such that the active compound enters the underlying tissue. Desirably, the external surface is the skin and topical administration desirably involves application of a pharmaceutically acceptable formulation to intact skin, to broken skin, to raw skin or to an open skin wound. Desirably the compound is a compound of Formula I.

"Transdermal administration" or "transdermally administering" as used herein refers to the diffusion of an agent across the barrier of the skin resulting from topical administration or other application of a compound or a pharmaceutically acceptable formulation of a compound. Desirably the compound is a compound of Formula I.

Where a group may be optionally substituted, optional substituents include, but are not limited to: halogen (i.e., —F, —Cl, —Br, or —I), —CO₂H, —CO₂(lower alkyl), —CO₂(lower alkoxyalkyl), -(lower alkyl), -(lower alkoxyalkyl), —O(lower alkyl), —O(lower alkoxyalkyl), —NH(lower alkyl), —NH(lower alkoxyalkyl), —N(lower alkyl)₂, and —N(lower alkoxyalkyl)₂.

These definitions and others stated in The Merck Manual 16$^{th}$ edition 1992 (Chapter 25. pp 461-498; Chapter 25, pp 498-507; and Chapter 24, pp 413-429) and Goodman and Gilman's "The Pharmacological Basis of Therapeutics" 11$^{th}$ edition 2006 (Chapter 34, pp 899-908; Chapter 31, pp 823-824 and pp 830-832; and Chapter 32, pp 845-846) are herein incorporated by reference in these definitions.

Other features and advantages of the invention will be apparent from the following Detailed Description and the Claims.

DETAILED DESCRIPTION

The present invention relates to the use of a pharmaceutically effective amount of a short-acting calcium channel blocking compound to treat ischemic heart conditions, cardiac arrhythmias, hypertensive crisis in an emergency room setting, hypertension before, during, or after surgery, no-reflow phenomenon following reperfusion, and diseases associated with decreased skeletal muscle blood flow. The compounds used in the compositions, kits, and methods of the present invention are rendered short-acting by covalent attachment of esterase sensitive groups to molecules derived from the phenylalkylamine (e.g., verapamil) class of calcium channel blockers and may be formulated for sublingual, buccal, transdermal, intranasal, inhalation, topical, and parenteral (e.g., intravenous) routes of administration. Pharmaceutical compositions containing the compounds disclosed herein may be included in a kit with instructions for administration according to the methods of the invention.

In the context of this invention, a short acting calcium channel blocking compound is meant to infer a compound that produces the desired effect and is then rapidly inactivated metabolically. A short acting CCB is meant to have a duration of action of from less than 1 minute to less than 60 minutes. Preferably the compound's duration of action will be from 1 minute to 30 minutes.

In desirable embodiments, the compounds used in the methods of the present invention are defined structurally in Formula I

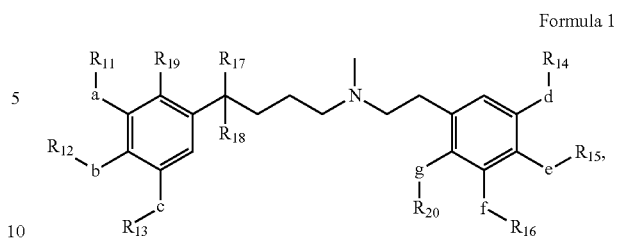

Formula 1 or a pharmaceutically acceptable addition salt thereof, or any enantiomer or diastereomer thereof, where the compounds represented by Formula I are further defined as follows:

each a, b, c, d, e, f, and g is, independently, —CH₂—, —O—, —S—, or a single bond;

each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —CO₂(lower alkyl), lower alkyl substituted with —CO₂(lower alkoxyalkyl), lower alkyl substituted with fluorine or chlorine, lower alkoxyalkyl, lower alkoxyalkyl substituted with —CO₂(lower alkyl), lower alkoxyalkyl substituted with —CO₂(lower alkoxyalkyl), lower alkoxyalkyl substituted with fluorine or chlorine, or $CO_2R_{10}$;

each $R_{10}$ is, independently, lower alkyl or lower alkoxyalkyl;

$R_{18}$ is H, CN, or $CO_2R_{10}$; and $R_{19}$ is CH₃ or H.

The compounds defined by Formula I may exist as free bases or as pharmaceutically acceptable acid addition salts.

As described above, the short-acting calcium channel blockers of the invention (e.g., the compounds defined by Formula I) may be used to treat disorders in which the regulation of calcium plays a role in normal hemostasis. Such disorders include, for example, pulmonary hypertension, peripheral vascular disease, mild congestive heart failure, hypertrophic subaortic stenosis, protection against ischemic injury, stroke, migraine, tumor resistance to antineoplastic drugs, achalasia, esophageal spasms, bronchial asthma, premature labor, dysmenorrhea, and enhancement of success in renal transplantation.

Pharmaceutical agents, such as a calcium channel-blocking compound, can be made with relatively short durations of therapeutic action, ranging from the ultra-short to medium-range, through non-hepatic means of inactivation. Such agents may be subject to extensive metabolism in blood by serum esterases, as well as potential metabolism in the liver. Rapid elimination or biotransformation to inactive or less active products minimizes accumulation with prolonged or repeated administration. A calcium channel-blocking compound that is rendered sensitive to serum esterases is expected to undergo rapid degradation to inactive or less active metabolites in the blood. This may be considered analogous to the rapid degradation experienced by succinylcholine (Stanski, D. R. and Hug, C. C., Jr. *Anesthesiology* 57: 435-438 (1982)) and enables a more predictable correlation of dose with the duration of pharmacologic effect.

Anti-anginal drugs relieve or prevent coronary ischemia by increasing oxygen supply to the heart or by decreasing myocardial oxygen demand. There are three main classes of pharmaceutical agents that are used to treat angina (organic nitrates, calcium channel blockers, and beta-adrenergic antagonists also known as beta-blockers). Organic nitrates (e.g., glyceryl trinitrate, nitroglycerin) are generally effective agents for treating angina and cause vasodilation through release of nitric oxide (NO) to coronary arteries and coronary smooth muscle. However, a major limitation of the use of organic nitrates is the development of nitrate tolerance. Calcium channel blockers (e.g., verapamil, nicardipine, nifedipine, clevidipine, diltiazem, bepredil) antagonize calcium channels in arteriole smooth muscle and cardiac muscle resulting in vasodilation and/or reduced cardiac contractility. Calcium channel blockers are generally well tolerated with minor adverse effects including hypotension, dizziness, edema, nausea, and vomiting, and are contraindicated for patients with hypertrophic obstructive cardiomyopathies.

Medications used to treat atrial fibrillation and slow down the abnormal and rapid heart rate include calcium channel blockers (e.g., verapamil, diltiazem), digoxin (e.g., digitalis), and beta-blockers (e.g., propranolol, atenolol, esmolol). These pharmaceutical agents slow the heart rate by retarding conduction of the electrical discharges through the atrio-ventricular node, but do not usually convert atrial fibrillation back into a normal rhythm. Other drugs or treatments are necessary to achieve a normal heart rhythm but these are generally associated with greater toxicity.

Calcium channel blockers and beta-blockers are often prescribed for acute pharmacological treatment of atrial flutter as well as traditional antiarrhythmic medications such as amiodarone.

Nitrate containing drugs, such as nitroglycerin or sodium nitroprusside, can be used to address these disorders involving blood flow and pressure regulation, but these drugs can produce rebound tachycardia and other adverse effects. Other traditional hypotensive agents, such as the calcium channel blocker nicardipine, are generally too long acting to effectively address blood pressure regulation surrounding surgery. In contrast, the compounds of the invention are short acting and thus overcome the undesirable characteristics and effects noted above in connection with existing therapies for cardiovascular disorders.

Pharmaceutical Formulations

Desirable routes of administration of the compounds (e.g., the compounds having Formula I) used in the present invention include sublingual, buccal, transdermal, intranasal, inhalation, topical, and parenteral (e.g., intravenous) administration. The compounds desirably are administered with a pharmaceutically acceptable carrier. Pharmaceutical formulations of the compounds described herein formulated for treatment of the disorders described herein are also part of the present invention.

For a transdermal delivery system, the administration of a therapeutic dose will, of course, be continuous rather than intermittent throughout the dosage regimen.

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of compounds of the invention. Desirably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

The compounds may also be formulated for nasal administration. For nasal administration, the solutions or suspensions are applied directly to the nasal cavity by conventional means, for example, with a dropper, pipette or spray. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example, a powder mix of the compound in a suitable powder base such as lactose, starch, and starch derivatives such as hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

For human use, a compound of the invention can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of Formula I into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. The formulation and preparation of such compositions is well-known to those skilled in the art of pharmaceutical formulation.

For administration by inhalation, compounds of in the invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount.

The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

The formulations for parenteral administration may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets.

Topical Pharmaceutical Formulations

Pharmaceutically acceptable topical formulations for use in accordance with the present invention can be formulated in conventional manner using one or more physiologically acceptable carriers comprising excipients and auxiliaries that facilitate processing of the compounds of the invention (e.g., a compound of Formula I) into preparations that can be used pharmaceutically. Proper formulation is dependent upon the desired product chosen. Non-limiting exemplary formulations are provided below.

The topical formulations useful in the subject invention can be made into a wide variety of product types. These include, but are not limited to, lotions, creams, gels, sticks, sprays, ointments, pastes, mousses, and cosmetics. The product types can include several types of carrier systems including, but not limited to, solutions, emulsions, gels, solids, and liposomes. Techniques for formulation and administration are standard in the art and can be found, for example, in "Remington: The Science and Practice of Pharmacy 20$^{th}$ edition" Lippincott Williams & Wilkins, Philadelphia, Pa. Eds Gennaro A. R. et al, 2000. The formulation can be selected to maximize delivery to a desired target site in the body such as the skin.

Lotions, which are preparations that are to be applied to the skin surface without friction, are typically liquid or semi-liquid preparations. Lotions may be formulated with an aqueous or oily base and will in general also contain one or more emulsifying agents, stabilizing agents, dispersing agents, suspending agents, thickening agents, or coloring agents.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase, also sometimes called the "internal" phase, generally contains petrolatum and a fatty alcohol such as cetyl or stearyl alcohol; the aqueous phase usually, although not necessarily, exceeds the oil phase in volume, and generally contains a humectant. The emulsifier in a cream formulation, as described in "Remington: The Science and Practice of Pharmacy 20$^{th}$ edition" Lippincott Williams & Wilkins, Philadelphia, Pa. Eds Gennaro A. R. et al, 2000, is generally a nonionic, anionic, cationic or amphoteric surfactant.

Gel formulations can also be used in connection with the present invention. As is appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Ointments, which are semisolid preparations, are typically based on petrolatum or other petroleum derivatives. As is appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As described, for example, in Remington: The Science and Practice of Pharmacy 20$^{th}$ edition" Lippincott Williams & Wilkins, Philadelphia, Pa. Eds Gennaro A. R. et al, 2000, at pages 845-849, ointment bases may be grouped in four classes: oleaginous bases; absorption bases; water-removable bases; and water-soluble bases. Oleaginous ointment bases include, for example, vegetable oils, fats obtained from animals, and semisolid hydrocarbons obtained from petroleum. Absorption bases, also known as emulsifiable ointment bases, contain little or no water and include, for example, hydroxystearin sulfate, anhydrous lanolin and hydrophilic petrolatum. Absorption bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Useful formulations of the invention also encompass sprays. Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, the carrier evaporates, leaving concentrated active agent at the site of administration.

A topical pharmaceutical formulation for use in the present invention may also include suitable solid or gel phase carriers. Examples of such carriers include, but are not limited to, calcium carbonate, calcium phosphate, various sugars, starches, cellulose derivatives, gelatin, and polymers such as polyethylene glycols.

Further, a topical pharmaceutical formulation may include a suitable emulsifier, i.e., an agent that enhances or facilitates mixing and suspending oil-in-water or water-in-oil. An emulsifying agent for use in the invention may consist of a single emulsifying agent or may be a blend of emulsifying agents and may be a nonionic, anionic or cationic surfactant or a blend of two or more such surfactants. Such surface-active agents are described, for example, in "McCutcheon's Detergent and Emulsifiers," North American Edition, 1980 Annual published by the McCutcheon Division, MC Publishing Company, 175 Rock Road, Glen Rock, N.J. 07452, USA.

Especially suitable nonionic emulsifying agents for inclusion in the pharmaceutically acceptable formulations for use in the present invention are those with a hydrophile-lipophile balance (HLB) as determined by the method described, for example, by Paul L. Lindner in "Emulsions and Emulsion", edited by Kenneth Lissant, published by Dekker, New York, N.Y., 1974, pages 188-190. Examples of such nonionic emulsifiers include, but are not limited to, "BRIJ 72," the trade name for a polyoxyethylene (2) stearyl ether having an HLB of 4.9; "BRIJ 721," the trade name for a polyoxyethylene (21) stearyl ether having an HLB of 15.5.

A topical pharmaceutical formulation may also contain suitable emollients. Emollients are materials that may be used for the prevention or relief of dryness, as well as for the protection of the skin. Useful emollients include, but are not limited to, cetyl alcohol, isopropyl myristate, stearyl alcohol, and the like. A wide variety of suitable emollients are known in the art and can be used in the formulations encompassed by the invention. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety.

A topical pharmaceutical formulation for use in the methods of the invention may also include suitable antioxidants, i.e., substances that inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene.

Moreover, topical pharmaceutical formulations for use in the present invention may also include suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel).

A topical pharmaceutical formulation for use in the present invention may further contain suitable chelating agents to form complexes with metal cations which do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2).

Topical pharmaceutical formulations useful for the methods of the invention may also include suitable neutralizing agents used to adjust the pH of the formulation to within a pharmaceutically acceptable range. For topical formulations, pH range desirably is 4.5-7.1. Most desirably, the pH range is 4.5-6.5.

Further, a topical pharmaceutical formulation may include suitable hydrophilic gelling agents. These components are, for example, diffusable compounds capable of increasing the viscosity of a polymer-containing solution through the interaction of the agent with the polymer. Also useful herein are hydrophilic gelling agents such as the acrylic acid/ethyl acrylate copolymers and the carboxyvinyl polymers sold by the B. F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyally pentaerythritol. A desirable viscosity increasing agent is for example Carbopol® Ultrez 10.

A topical pharmaceutical formulation may also contain one or more suitable solvents. Suitable solvents include ethanol, propylene glycol, glycerin, dipropylene glycol and polyethylene glycol. Non-lipophilic drugs typically display very low solubility in pharmaceutically acceptable solvents and/or carriers.

In addition, a topical pharmaceutical formulation for use in the present invention may include one or more suitable skin penetration enhancers. Suitable excipients are known in the art to be skin penetration enhancers (as described, for example, in Osborne D. W. and Henke J. J., "Skin penetration enhancers cited in the technical literature" *Pharm. Tech.* 21:58-66, 1997). Examples of skin penetration enhancers include water, ethanol, propylene glycol, oleic acid, oleyl alcohol, sodium lauryl sulfate, dimethylsulfoxide, 1-dodecylazacycloheptan-2-one (trade name Azone®), N-methyl-2-pyrrolidinone, 2-pyrrolidinone, D-limonene, 1,8-cineole, urea, and menthol are just a few of the known penetration enhancers. Diethylene glycol monoethyl ether NF (CAS number 111-90-0, INCI name ethoxydiglycol, trade name TRANSCUTOL®) (see, for example, Watkinson A. C. et al., "Aspects of the transdermal delivery of prostaglandins," *Int. J. Pharm.* 74:229-236, 1991; Rojas J. et al., "Optimization of binary and ternary solvent systems in the percutaneous absorption of morphine base," *STP Pharma Sciences,* 1:70-75, 1991; Watkinson A. C., Ph.D. Thesis, University of Wales, 1991; Ritschel W. A. et al., "Development of an intracutaneous depot for drugs. Binding, drug accumulation and retention studies," *Skin Pharmacol.* 4:235-245, 1991).

Diethylene glycol monoethyl ether NF (DGME) is a useful solvent for many drugs, especially non-lipophilic drugs having very low water solubility. In vitro skin absorption studies have shown increased flux values for compounds dissolved in DGME; however, DGME does not fluidize the stratum corneum lipids (Harrison J. E. et al., "The relative effect of Azone and Transcutol on permeant diffusivity and solubility in human stratum corneum," *Pharm. Res.,* 13:542-546, 1996), nor does DGME decrease the lag time associated with the permeant (Rojas J. et al., "Optimization of binary and ternary solvent systems in the percutaneous absorption of morphine base," *STP Pharma Sciences,* 1:70-75, 1991). These additional penetration-enhancing compounds can be used when desired in the pharmaceutical compositions described herein in the conventional range of from about 0.1 to about 10% and preferably about 1.0% to about 5.0% by weight of the topical composition.

Liquid forms, such as lotions suitable for topical administration or suitable for cosmetic application, may include a suitable aqueous or non-aqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges, patches, and the like.

Topical Administration

The compounds for use in the invention (e.g., compounds of Formula I) can be administered in a pharmaceutically acceptable topical (e.g., transdermal) formulation. Topical treatment regimens according to the practice of the invention may include applying the composition directly to the skin at the application site, from one to several times daily. Also included are delivery methods in the form of pharmaceutical patches.

These formulations may include a pharmaceutically acceptable carrier such as water, oils (including vegetable and mineral oils), cream bases, lotion bases, ointment bases, and the like. These bases include suspending agents, thickeners, penetration enhancers, and the like. Topical and transdermal formulations are well known to those in the art of cosmetics and topical pharmaceuticals and are described, for example, in Chapter 44 of "Remington: The Science and Practice of Pharmacy 20$^{th}$ edition" Lippincott Williams & Wilkins, Philadelphia, Pa. Eds Gennaro A. R. et al, 2000, which is incorporated herein by reference.

Topical (e.g., transdermal) formulations may also include pharmaceutically acceptable vehicles. Additives for topical formulations are well-known in the art, and may be added to the topical composition, as long as they are pharmaceutically acceptable and not deleterious to the epithelial cells or their function. Further, the additives should not cause deterioration in the stability of the formulation, in particular, of the active compound. For example, inert fillers, anti-irritants, tackifiers, excipients, fragrances, opacifiers, antioxidants, gelling agents, stabilizers, surfactants, emollients, coloring agents, preservatives, buffering agents, other permeation enhancers, and other conventional components of transdermal delivery devices as are known in the art. Excipients generally are carriers, diluents and/or vehicles used in formulating drug compositions. Excipients are standard in the art and examples of excipients and their application can be found, for instance, in Katz, M. (*Drug Design* 4:93-148, 1973).

Penetration or permeation through the skin of an active compound may be enhanced by an agent (e.g., p20 solvents) or a mixture of agents which, alone or in combination, act to increase the permeability of the skin to a drug. The enhanced permeation effected through the use of such enhancers can be observed, for example, by measuring the rate of diffusion of the drug through animal or human skin using a diffusion cell apparatus. A diffusion cell is described by Merritt et al. "Diffusion Apparatus for Skin Penetration," *J. of Controlled Release*, 1:161-162, 1984. Topical administration of a pharmaceutical agent can result in a limited distribution of the agent to the skin and surrounding tissues or, when the agent is removed from the treatment area by the bloodstream, can result in systemic distribution of the agent. However, transdermal administration desirably results in the diffusion of an agent across the barrier of the skin resulting from topical administration or other application of a pharmaceutically acceptable formulation. The stratum corneum acts as a barrier and few pharmaceutical agents are able to penetrate intact skin. In contrast, the epidermis and dermis are permeable to many solutes and absorption of drugs therefore occurs more readily through skin that is abraded or otherwise stripped of the stratum corneum to expose the epidermis. Transdermal delivery includes injection or other delivery through any portion of the skin or mucous membrane and absorption or permeation through the remaining portion. Absorption through intact skin can be enhanced by placing the active agent in an appropriate pharmaceutically acceptable vehicle before application to the skin. Passive topical administration may consist of applying the active agent directly to the treatment site in combination with emollients or penetration enhancers.

A topically (e.g., transdermally) administrable pharmaceutical formulation may also include an amount of a form of hyaluronic acid sufficient to transport the composition through the skin of a patient into the epidermis or dermis where the composition remains until discharged via the lymphatic system. Desirably, the active compound is 1-5% by weight of the formulation and hyaluronic acid is 1-3% by weight of the formulation. Desirable forms of hyaluronic acid have a molecular weight greater than about 150,000 daltons and less than 750,000 daltons. Salts of hyaluronic acid are also desirable for use in the methods encompassed by the present invention.

Many of the compounds of the present invention can be provided as pharmaceutically acceptable acid addition salts. Such pharmaceutically acceptable acid addition salts are those salts that retain the biological effectiveness and properties of the free bases.

The sensitivity of the CCB analogs to hydrolysis by esterase enzymes can be inferred by measuring their stability in human plasma. This measure provides a qualitative in-vitro method of ranking the compounds in order of relative stability and provides a useful comparison to CCBs with longer half-lives (i.e. diltiazem, verapamil and nifedipine). Such assays are available from commercial service providers such as MDS Pharma Services. The assay is conducted in the following manner:

The test matrix is pooled human plasma;
The concentration of the analog being tested is 10 µM;
The mixture is incubated in duplicate at 37° C.;
The incubation is stopped at 0, 0.5, 1, 2 and 30 min by adding an equal volume of acetonitrile; and
The extracted samples are analyzed by either (+)- or (−)-ESI LC/MS using a pre-established generic method.

Data is expressed as % of the zero time samples.

General Synthetic Methodology

Compounds of the invention may be prepared as described herein. In particular, the method depicted in Scheme 1 may be used for the synthesis of compounds having Formula I. The compounds may be prepared by heating a halogen substituted compound of general structure A with an amine of general structure B. The reaction may be conducted by heating the reactants together neat or in the presence of a solvent such as dichloromethane or tetrahydrofuran. A catalyst such as sodium iodide may or may not be added.

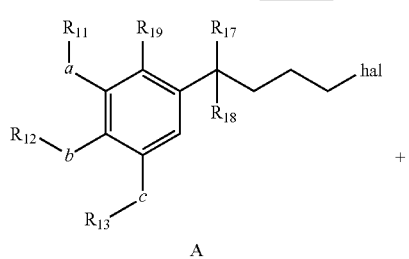

Scheme 1

A

+

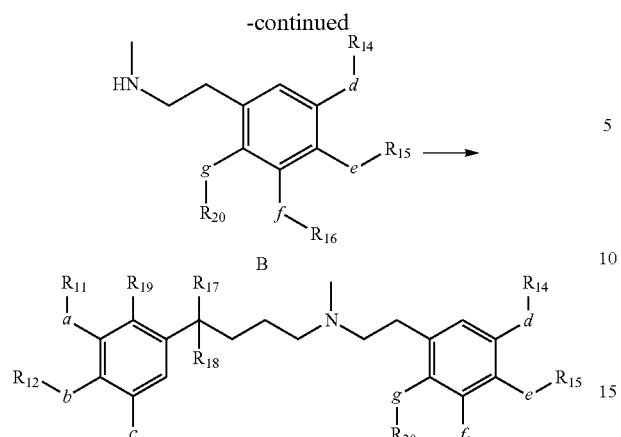

Formula 1

The compounds of Formula I are further described as follows:

each a, b, c, d, e, f, and g is, independently, —CH$_2$—, —O—, —S—, or a single bond;

each $R_{11}$, $R_{12}$, $R_{13}$, $R_{14}$, $R_{15}$, $R_{16}$, $R_{17}$, and $R_{20}$ is, independently: H, lower alkyl, lower alkyl substituted with —CO$_2$(lower alkyl), lower alkyl substituted with —CO$_2$(lower alkoxyalkyl), lower alkyl substituted with fluorine or chlorine, lower alkoxyalkyl, lower alkoxyalkyl substituted with —CO$_2$(lower alkyl), lower alkoxyalkyl substituted with —CO$_2$(lower alkoxyalkyl), lower alkoxyalkyl substituted with fluorine or chlorine, or CO$_2$R$_{10}$;

each $R_{10}$ is, independently, lower alkyl or lower alkoxyalkyl;

$R_{18}$ is H, CN, or CO$_2$R$_{10}$; and $R_{19}$ is CH$_3$ or H.

Starting Materials and Intermediate Compounds

The halogen substituted compounds of general structure A used to prepare compounds of Formula 1 exemplified in this invention are depicted in Table 1.

TABLE 1

(Table 1 contains chemical structures 1a through 1k with associated structural diagrams.)

TABLE 1-continued

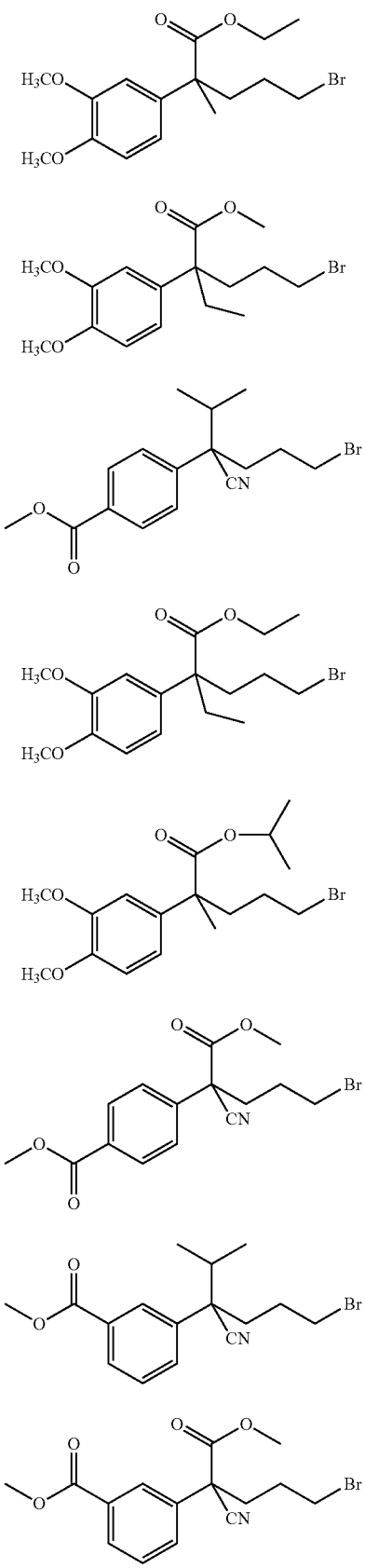
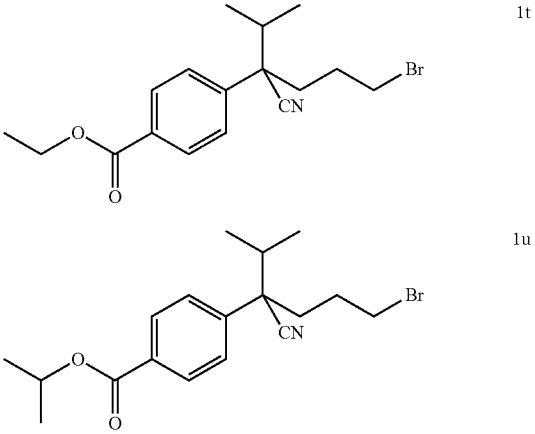

The compounds of Table 1 may be alternatively described using the following nomenclature:

1a: Dimethyl 2-(3-bromopropyl)-2-(3,4-dimethoxyphenyl)malonate;
1b: Methyl 5-bromo-2-cyano-2-(3,4-dimethoxyphenyl)pentanoate;
1c: Ethyl 5-bromo-2-cyano-2-(3,4-dimethoxyphenyl)pentanoate;
1d: Isopropyl 5-bromo-2-cyano-2-(3,4-dimethoxyphenyl)pentanoate;
1e: Methyl 5-chloro-2-(3,4-dimethoxyphenyl)-2-isopropylpentanoate;
1f: 5-Bromo-2-(3,4-dimethoxyphenyl)-2-isopropylpentanenitrile;
1g: 1-Ethyl 3-methyl 2-(3-bromopropyl)-2-(3,4-dimethoxyphenyl)malonate;
1h: Diethyl 2-(3-bromopropyl)-2-(3,4-dimethoxyphenyl)malonate;
1i: 1-tert-butyl 3-methyl 2-(3-bromopropyl)-2-(3,4-dimethoxyphenyl)malonate;
1j: 1-Isopropyl 3-methyl 2-(3-bromopropyl)-2-(3,4-dimethoxyphenyl)malonate;
1k: Methyl 5-bromo-2-(3,4-dimethoxyphenyl)-2-methylpentanoate;
1l: Ethyl 5-bromo-2-(3,4-dimethoxyphenyl)-2-methylpentanoate;
1m: Methyl 5-bromo-2-(3,4-dimethoxyphenyl)-2-ethylpentanoate;
1n: Methyl 4-(6-bromo-3-cyano-2-methylhexan-3-yl)benzoate;
1o: Ethyl 5-bromo-2-(3,4-dimethoxyphenyl)-2-ethylpentanoate;
1p: Isopropyl 5-bromo-2-(3,4-dimethoxyphenyl)-2-methylpentanoate;
1q: Methyl 4-(5-bromo-2-cyano-1-methoxy-1-oxopentan-2-yl)benzoate;
1r: Methyl 3-(6-bromo-3-cyano-2-methylhexan-3-yl)benzoate;
1s: Methyl 3-(5-bromo-2-cyano-1-methoxy-1-oxopentan-2-yl)benzoate;
1t: Ethyl 4-(6-bromo-3-cyano-2-methylhexan-3-yl)benzoate; and
1u: Isopropyl 4-(6-bromo-3-cyano-2-methylhexan-3-yl)benzoate.

The amine compounds of general structure B used to prepare compounds of Formula I exemplified in this invention are depicted in Table 2.

TABLE 2

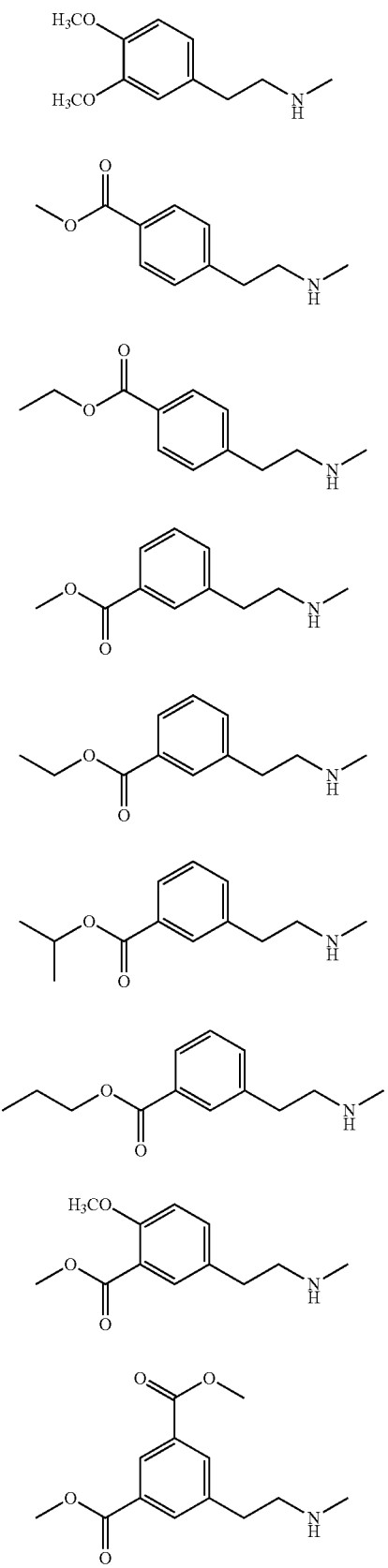

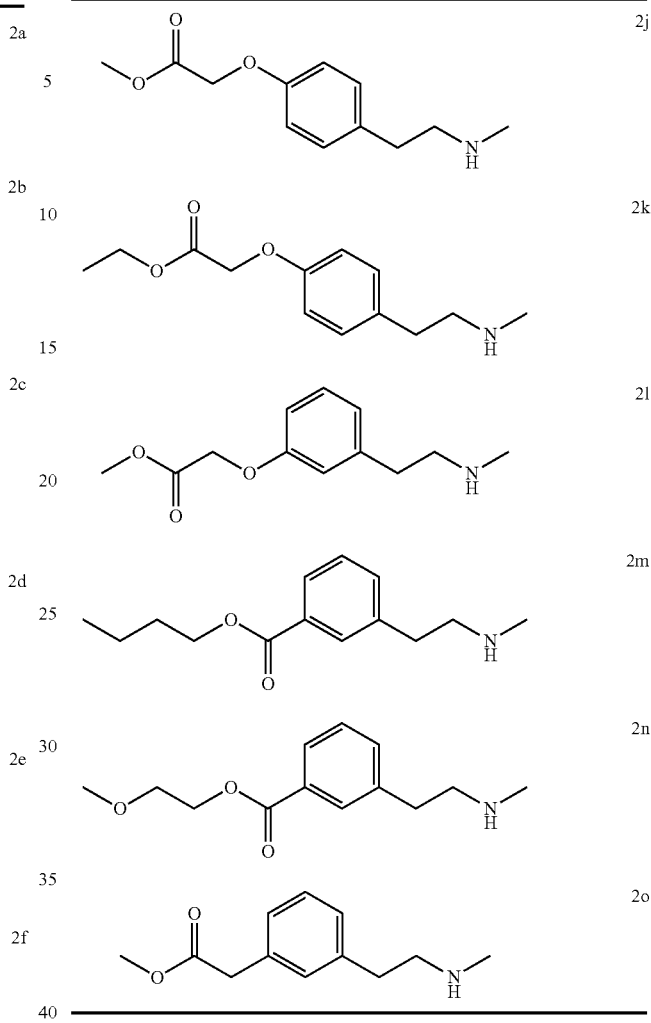

The compounds of Table 2 may be alternatively described using the following nomenclature:

2a: 2-(3,4-Dimethoxyphenyl)-N-methylethanamine;
2b: Methyl 4-(2-(methylamino)ethyl)benzoate;
2c: Ethyl 4-(2-(methylamino)ethyl)benzoate;
2d: Methyl 3-(2-(methylamino)ethyl)benzoate;
2e: Ethyl 3-(2-(methylamino)ethyl)benzoate;
2f: Isopropyl 3-(2-(methylamino)ethyl)benzoate;
2g: Propyl 3-(2-(methylamino)ethyl)benzoate;
2h: Methyl 2-methoxy-5-(2-(methylamino)ethyl)benzoate;
2i: Dimethyl 5-(2-(methylamino)ethyl)isophthalate;
2j: Methyl 2-(4-(2-(methylamino)ethyl)phenoxy)acetate;
2k: Ethyl 2-(4-(2-(methylamino)ethyl)phenoxy)acetate;
2l: Methyl 2-(3-(2-(methylamino)ethyl)phenoxy)acetate;
2m: Butyl 3-(2-(methylamino)ethyl)benzoate;
2n: 2-Methoxyethyl 3-(2-(methylamino)ethyl)benzoate; and
2o: Methyl 2-(3-(2-(methylamino)ethyl)phenyl)acetate;

Compounds of Formula 1 Exemplified in this Invention

The compounds of Formula 1 exemplified in this invention are depicted in Table 3.

TABLE 3
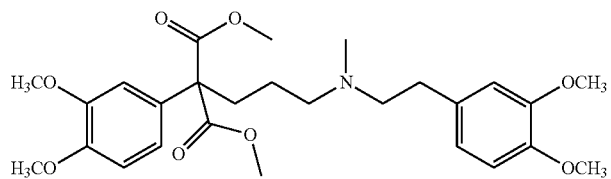 [SMILES: COC(=O)C(CCCN(C)CCc1ccc(OC)c(OC)c1)(C(=O)OC)c1ccc(OC)c(OC)c1] 3a
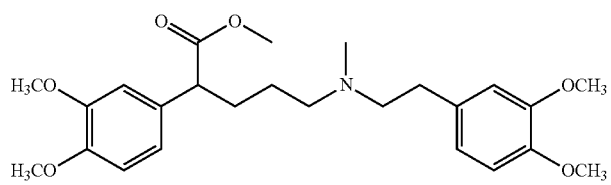 [SMILES: COC(=O)C(CCCN(C)CCc1ccc(OC)c(OC)c1)c1ccc(OC)c(OC)c1] 3b
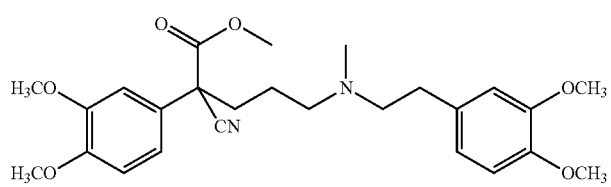 [SMILES: COC(=O)C(C#N)(CCCN(C)CCc1ccc(OC)c(OC)c1)c1ccc(OC)c(OC)c1] 3c
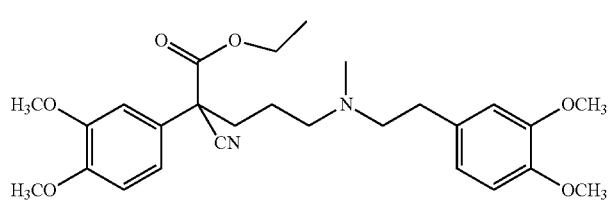 [SMILES: CCOC(=O)C(C#N)(CCCN(C)CCc1ccc(OC)c(OC)c1)c1ccc(OC)c(OC)c1] 3d
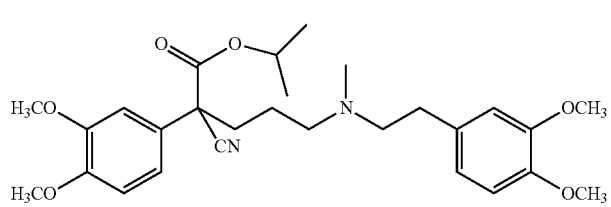 [SMILES: COc1ccc(CCN(C)CCCC(C#N)(C(=O)OC(C)C)c2ccc(OC)c(OC)c2)cc1OC] 3e
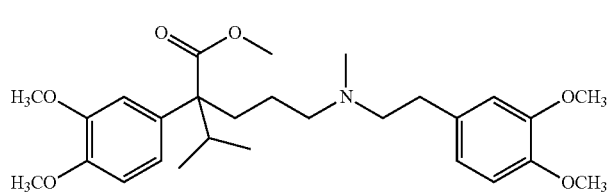 [SMILES: COC(=O)C(CCCN(C)CCc1ccc(OC)c(OC)c1)(c1ccc(OC)c(OC)c1)C(C)C] 3f
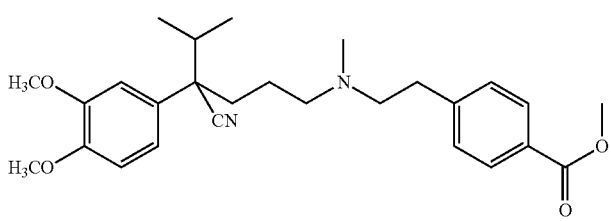 [SMILES: COC(=O)c1ccc(CCN(C)CCCC(C#N)(c2ccc(OC)c(OC)c2)C(C)C)cc1] 3g
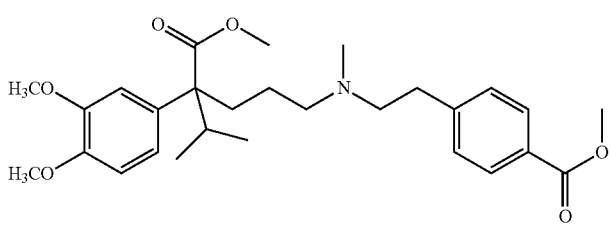 [SMILES: COC(=O)c1ccc(CCN(C)CCCC(C(=O)OC)(c2ccc(OC)c(OC)c2)C(C)C)cc1] 3h TABLE 3-continued
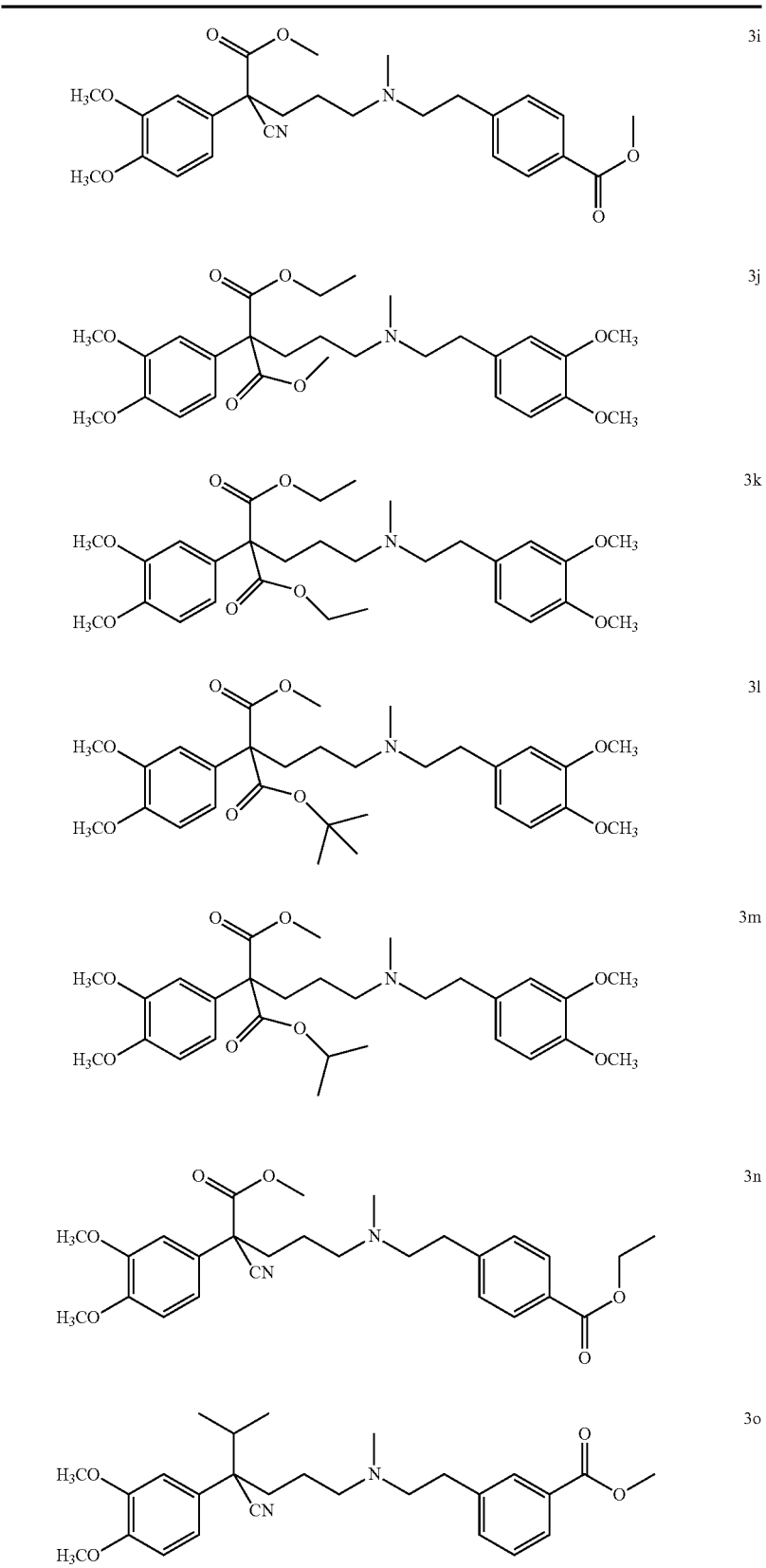

TABLE 3-continued
| | |
|---|---|
| 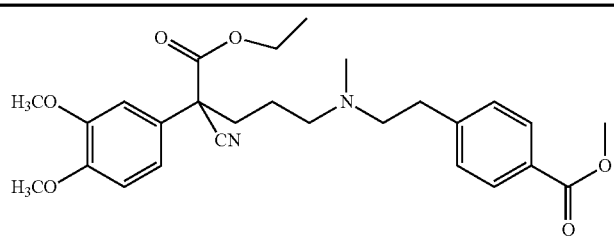 | 3p |
| 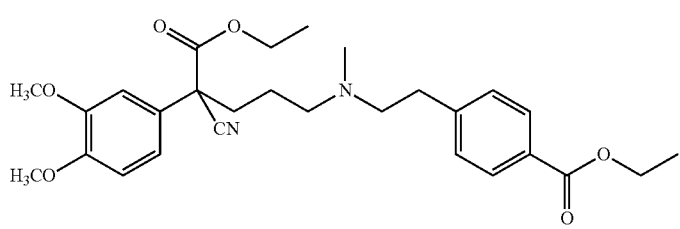 [SMILES: CCOC(=O)c1ccc(CCN(C)CCCC(C#N)(C(=O)OCC)c2ccc(OC)c(OC)c2)cc1] | 3q |
| 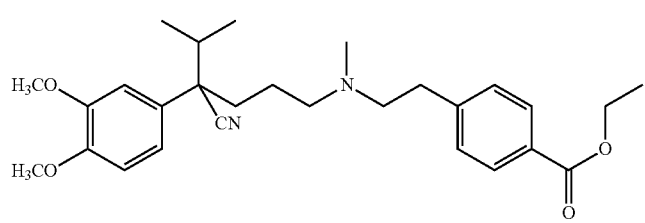 [SMILES: CCOC(=O)c1ccc(CCN(C)CCCC(C#N)(c2ccc(OC)c(OC)c2)C(C)C)cc1] | 3r |
| 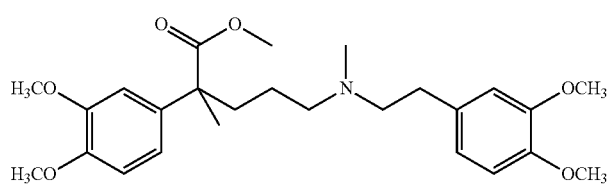 | 3s |
| 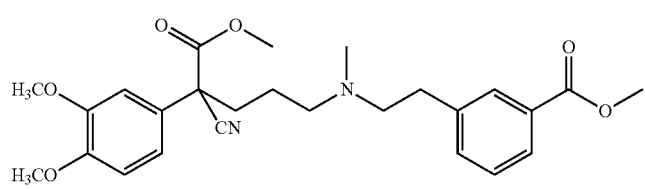 [SMILES: COC(=O)c1cccc(CCN(C)CCCC(C#N)(C(=O)OC)c2ccc(OC)c(OC)c2)c1] | 3t |
| 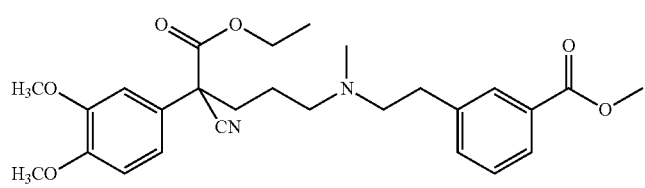 [SMILES: CCOC(=O)C(C#N)(CCCN(C)CCc1cccc(C(=O)OC)c1)c1ccc(OC)c(OC)c1] | 3u |
| 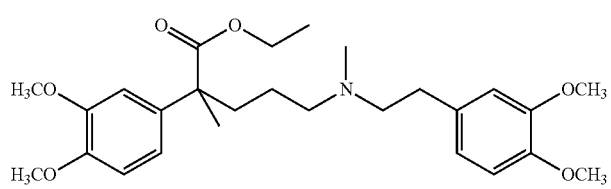 | 3v |
| 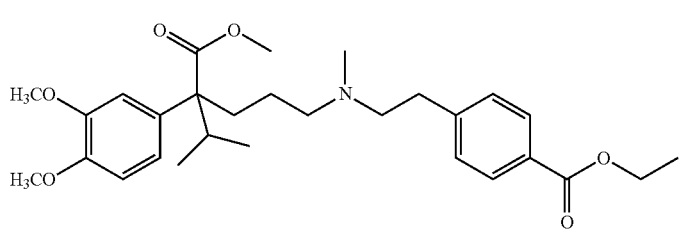 [SMILES: CCOC(=O)c1ccc(CCN(C)CCCC(C(=O)OC)(c2ccc(OC)c(OC)c2)C(C)C)cc1] | 3w |

TABLE 3-continued
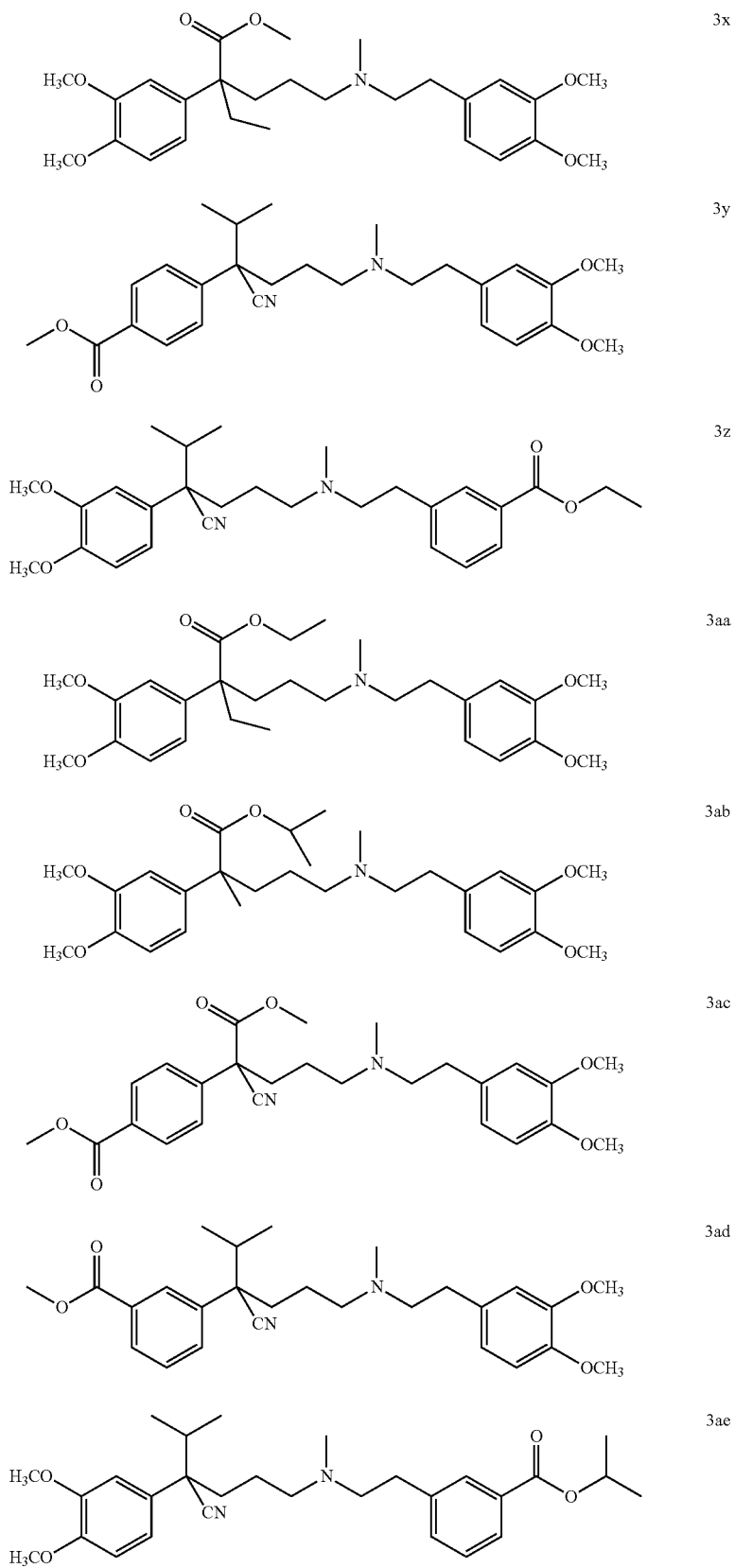

TABLE 3-continued
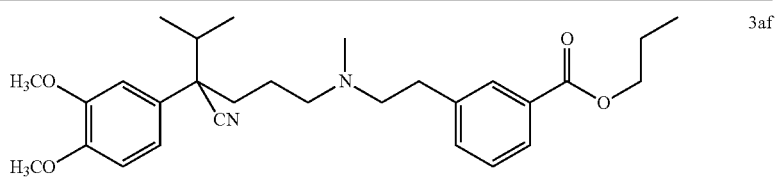
3af
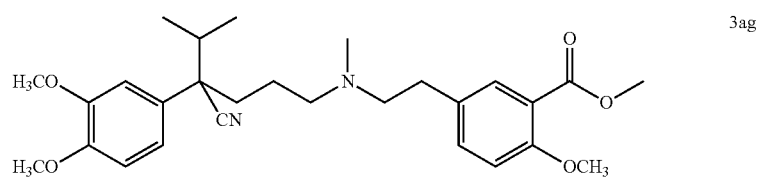
3ag
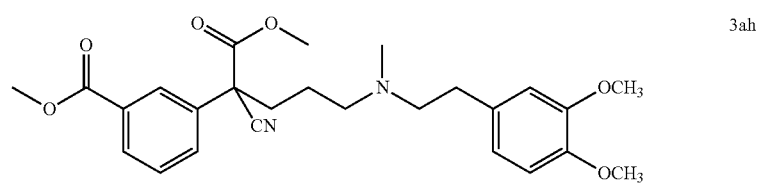
3ah
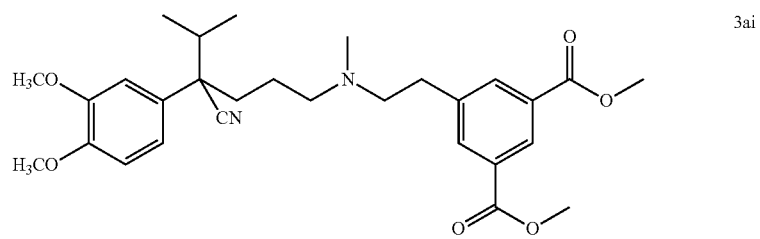
3ai
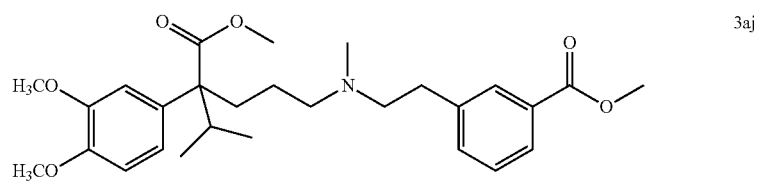
3aj
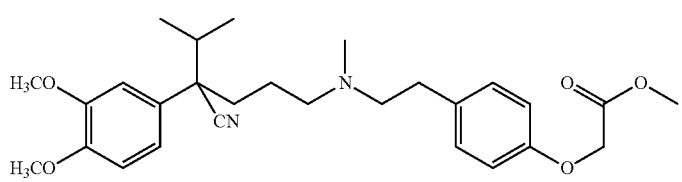 [SMILES: COC(=O)COc1ccc(CCN(C)CCCC(C#N)(c2ccc(OC)c(OC)c2)C(C)C)cc1]
3ak
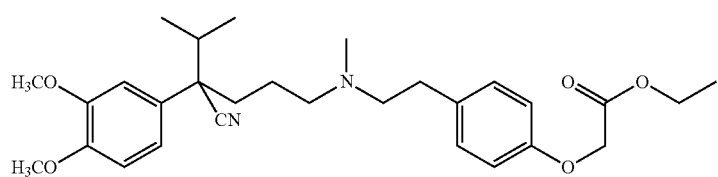 [SMILES: CCOC(=O)COc1ccc(CCN(C)CCCC(C#N)(c2ccc(OC)c(OC)c2)C(C)C)cc1]
3al
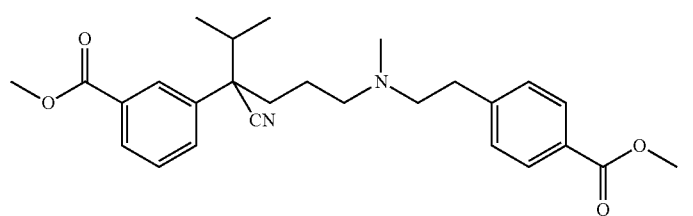
3am TABLE 3-continued
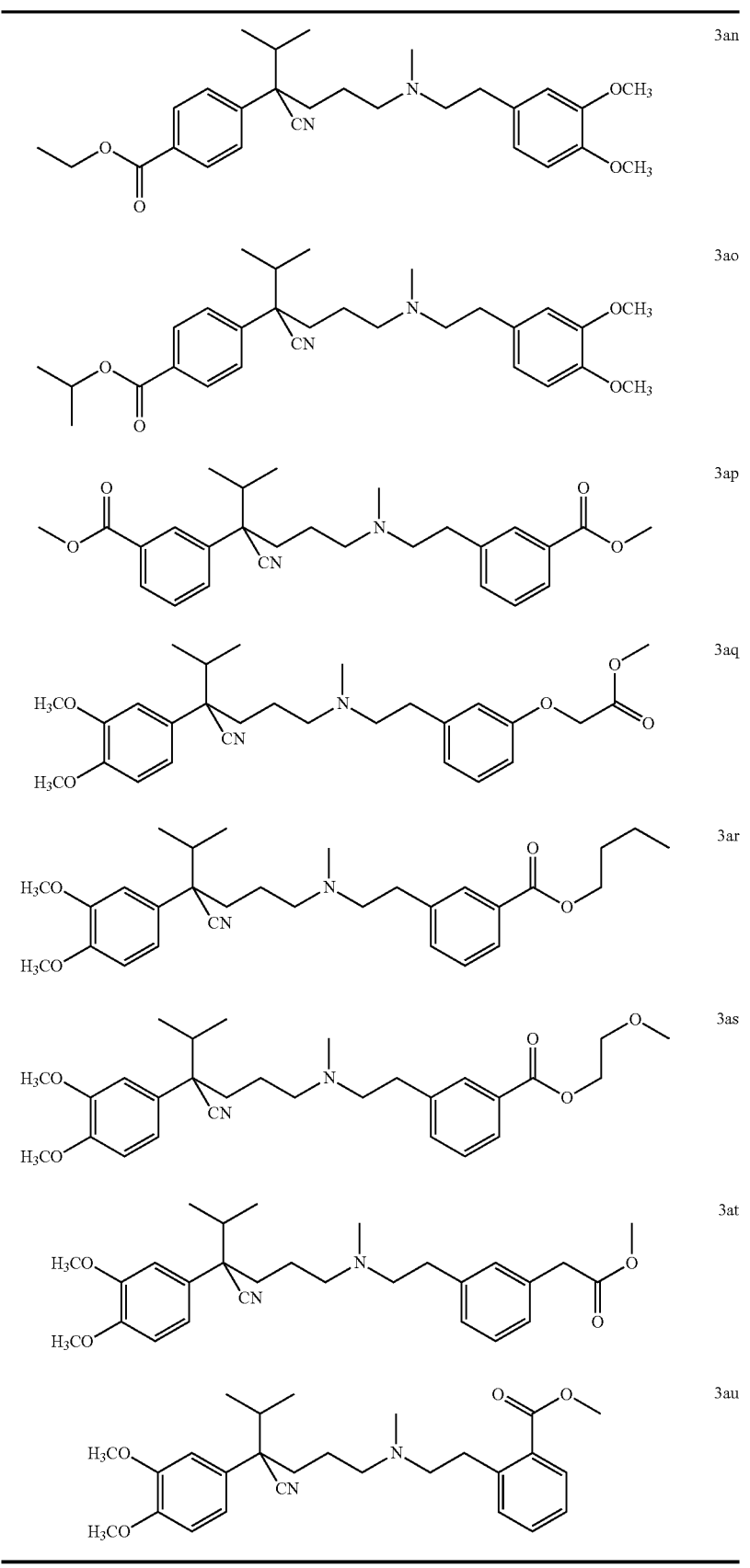

The compounds of Table 3 may be alternatively described using the following nomenclature:

3a: Dimethyl 2-(3-((3,4-dimethoxyphenethyl)(methyl)amino)propyl)-2-(3,4-dimethoxyphenyl)malonate;
3b: Methyl 5-((3,4-dimethoxyphenethyl)(methyl)amino)-2-(3,4-dimethoxyphenyl)pentanoate;
3c: Methyl 2-cyano-5-((3,4-dimethoxyphenethyl)(methyl)amino)-2-(3,4-dimethoxyphenyl)pentanoate;
3d: Ethyl 2-cyano-5-((3,4-dimethoxyphenethyl)(methyl)amino)-2-(3,4-dimethoxyphenyl)pentanoate;
3e: Isopropyl 2-cyano-5-((3,4-dimethoxyphenethyl)(methyl)amino)-2-(3,4-dimethoxyphenyl)pentanoate;
3f: Methyl 5-((3,4-dimethoxyphenethyl)(methyl)amino)-2-(3,4-dimethoxyphenyl)-2-isopropylpentanoate;
3g: Methyl 4-(2-((4-cyano-4-(3,4-dimethoxyphenyl)-5-methylhexyl)(methyl)amino)ethyl)benzoate;
3h: Methyl 4-(2-((4-(3,4-dimethoxyphenyl)-4-(methoxycarbonyl)-5-methylhexyl)(methyl)amino)ethyl)benzoate;
3i: Methyl 4-(2-((4-cyano-4-(3,4-dimethoxyphenyl)-5-methoxy-5-oxopentyl)(methyl)amino)ethyl)benzoate;
3j: 1-Ethyl 3-methyl 2-(3-((3,4-dimethoxyphenethyl)(methyl)amino)propyl)-2-(3,4-dimethoxyphenyl)malonate;
3k: Diethyl 2-(3-((3,4-dimethoxyphenethyl)(methyl)amino)propyl)-2-(3,4-dimethoxyphenyl)malonate;
3l: 1-tert-Butyl 3-methyl 2-(3-((3,4-dimethoxyphenethyl)(methyl)amino)propyl)-2-(3,4-dimethoxyphenyl)malonate;
3m: 1-Isopropyl 3-methyl 2-(3-((3,4-dimethoxyphenethyl)(methyl)amino)propyl)-2-(3,4-dimethoxyphenyl)malonate;
3n: Ethyl 4-(2-((4-cyano-4-(3,4-dimethoxyphenyl)-5-methoxy-5-oxopentyl)(methyl)amino)ethyl)benzoate;
3o: Methyl 3-(2-((4-cyano-4-(3,4-dimethoxyphenyl)-5-methylhexyl)(methyl)amino)ethyl)benzoate;
3p: Methyl 4-(2-((4-cyano-4-(3,4-dimethoxyphenyl)-5-ethoxy-5-oxopentyl)(methyl)amino)ethyl)benzoate;
3q: Ethyl 4-(2-((4-cyano-4-(3,4-dimethoxyphenyl)-5-ethoxy-5-oxopentyl)(methyl)amino)ethyl)benzoate;
3r: Ethyl 4-(2-((4-cyano-4-(3,4-dimethoxyphenyl)-5-methylhexyl)(methyl)amino) ethyl)benzoate;
3s: Methyl 5-((3,4-dimethoxyphenethyl)(methyl)amino)-2-(3,4-dimethoxyphenyl)-2-methylpentanoate;
3t: Methyl 3-(2-((4-cyano-4-(3,4-dimethoxyphenyl)-5-methoxy-5-oxopentyl)(methyl)amino) ethyl)benzoate;
3u: Methyl 3-(2-((4-cyano-4-(3,4-dimethoxyphenyl)-5-ethoxy-5-oxopentyl)(methyl)amino) ethyl)benzoate;
3v: Ethyl 5-((3,4-dimethoxyphenethyl)(methyl)amino)-2-(3,4-dimethoxyphenyl)-2-methylpentanoate;
3w: Ethyl 4-(2-((4-(3,4-dimethoxyphenyl)-4-(methoxycarbonyl)-5-methylhexyl)(methyl)amino)ethyl)benzoate;
3x: Methyl 5-((3,4-dimethoxyphenethyl)(methyl)amino)-2-(3,4-dimethoxyphenyl)-2-ethylpentanoate;
3y: Methyl 4-(3-cyano-6-((3,4-dimethoxyphenethyl)(methyl)amino)-2-methylhexan-3-yl)benzoate;
3z: Ethyl 3-(2-((4-cyano-4-(3,4-dimethoxyphenyl)-5-methylhexyl)(methyl)amino) ethyl)benzoate;
3aa: Ethyl 5-((3,4-dimethoxyphenethyl)(methyl)amino)-2-(3,4-dimethoxyphenyl)-2-ethylpentanoate;
3ab: Isopropyl 5-((3,4-dimethoxyphenethyl)(methyl)amino)-2-(3,4-dimethoxyphenyl)-2-methylpentanoate;
3ac: Methyl 4-(2-cyano-5-((3,4-dimethoxyphenethyl)(methyl)amino)-1-methoxy-1-oxopentan-2-yl)benzoate;
3ad: Methyl 3-(3-cyano-6-((3,4-dimethoxyphenethyl)(methyl)amino)-2-methylhexan-3-yl)benzoate;
3ae: Isopropyl 3-(2-((4-cyano-4-(3,4-dimethoxyphenyl)-5-methylhexyl)(methyl)amino)ethyl)benzoate;
3af: Propyl 3-(2-((4-cyano-4-(3,4-dimethoxyphenyl)-5-methylhexyl)(methyl)amino)ethyl)benzoate;
3ag: Methyl 5-(2-((4-cyano-4-(3,4-dimethoxyphenyl)-5-methylhexyl)(methyl)amino)ethyl)-2-methoxybenzoate;
3ah: Methyl 3-(2-cyano-5-((3,4-dimethoxyphenethyl)(methyl)amino)-1-methoxy-1-oxopentan-2-yl)benzoate;
3ai: Dimethyl 5-(2-((4-cyano-4-(3,4-dimethoxyphenyl)-5-methylhexyl) (methyl)amino)ethyl)isophthalate;
3aj: Methyl 3-(2-((4-(3,4-dimethoxyphenyl)-4-(methoxycarbonyl)-5-methylhexyl)(methyl)amino)ethyl)benzoate;
3ak: Methyl 2-(4-(2-((4-cyano-4-(3,4-dimethoxyphenyl)-5-methylhexyl)(methyl)amino)ethyl)phenoxy)acetate;
3al: Ethyl 2-(4-(2-((4-cyano-4-(3,4-dimethoxyphenyl)-5-methylhexyl)(methyl)amino) ethyl)phenoxy)acetate;
3am: Methyl 3-(3-cyano-6-((4-(methoxycarbonyl)phenethyl)(methyl)amino)-2-methylhexan-3-yl)benzoate;
3an: Ethyl 4-(3-cyano-6-((3,4-dimethoxyphenethyl)(methyl)amino)-2-methylhexan-3-yl)benzoate;
3ao: Isopropyl 4-(3-cyano-6-((3,4-dimethoxyphenethyl)(methyl)amino)-2-methylhexan-3-yl)benzoate;
3ap: Methyl 3-(2-((4-cyano-4-(3-(methoxycarbonyl)phenyl)-5-methylhexyl) (methyl)amino)ethyl)benzoate;
3aq: Methyl 2-(3-(2-((4-cyano-4-(3,4-dimethoxyphenyl)-5-methylhexyl) (methyl)amino)ethyl)phenoxy)acetate;
3ar: Butyl 3-(2-((4-cyano-4-(3,4-dimethoxyphenyl)-5-methylhexyl) (methyl)amino)ethyl)benzoate;
3as: 2-Methoxyethyl 3-(2-((4-cyano-4-(3,4-dimethoxyphenyl)-5-methylhexyl) (methyl)amino)ethyl)benzoate;
3at: Methyl 2-(3-(2-((4-cyano-4-(3,4-dimethoxyphenyl)-5-methylhexyl)(methyl) amino)ethyl)phenyl)acetate; and
3au: Methyl 2-(2-((4-cyano-4-(3,4-dimethoxyphenyl)-5-methylhexyl)(methyl) amino)ethyl)benzoate.

In order that this invention be more fully understood, the following preparative examples are set forth. These examples are for the purpose of illustration only and are not to be construed as limiting the scope of the invention in any way.

EXAMPLES

Compounds needed as synthetic starting materials that were not available from commercial sources were synthesized. If not mentioned otherwise, all evaporations were performed under reduced pressure, preferably between about 15 mm Hg and 100 mm Hg. The structure of final products, intermediates and starting materials was confirmed by standard analytical methods such as elemental analysis, NMR and MS.

Preparation of starting materials and intermediate compounds used to prepare the compounds of Formula 1 exemplified in this invention are described in the following examples.

For the Compounds Listed in Table 1

Example 1. 5-Bromo-2-(3,4-dimethoxyphenyl)-2-isopropylpentanenitrile (1f)

Method A Step 1:

To a solution of 9.99 g (56.4 mmol) of (3,4-Dimethoxyphenyl)acetonitrile in 141 mL of tetrahydrofuran (THF) at −30° C., was slowly added 56.4 mL (56.4 mmol) of sodium bis(trimethylsilyl)amide (NaHMDS, 1.0 M in THF). The mixture was stirred at −30° C. for 10 minutes and 10.6 mL (113.0 mmol) of 2-bromopropane was added. The mixture was heated to reflux for 2 hours (h) then left at 22° C. for about 16 h. A saturated aqueous solution of NH$_4$Cl was added and the mixture was extracted with ethyl acetate. The organic layer was washed with brine, dried (Na$_2$SO$_4$), filtered and evaporated. The residue was purified by flash chromatography on silica gel eluting first with hexane and then gradually increasing to 15% ethyl acetate/hexane to give 2-(3,4-dimethoxyphenyl)-3-methylbutanenitrile as an oil.

Method A Step 2:

To a solution of 11.21 g (51.1 mmol) of 2-(3,4-dimethoxyphenyl)-3-methylbutanenitrile in 126 mL of tetrahydrofuran (THF) at −30° C., was slowly added 46.0 mL (46.0 mmol) of sodium bis(trimethylsilyl)amide (NaHMDS, 1.0 M in THF). The mixture was stirred at −30° C. for 10 minutes and 9.40 mL (256 mmol) of 1,3-dibromopropane was added dropwise. The mixture was warmed to 22° C. and stirred for about 16 h. A saturated aqueous solution of NH$_4$Cl was then added and the mixture was extracted with ethyl acetate. The organic layer was washed with brine, dried (Na$_2$SO$_4$), filtered and evaporated. The residue was purified by flash chromatography on silica gel eluting first with hexane and then gradually increasing to 15% ethyl acetate/hexane to give 5-bromo-2-(3,4-dimethoxyphenyl)-2-isopropylpentanenitrile as an oil.

Unless otherwise indicated, the following compounds were prepared by procedures analogous to those described in Method A:

Example 2

1a: Dimethyl 2-(3-bromopropyl)-2-(3,4-dimethoxyphenyl)malonate

For Step 1, (3,4-dimethoxy-phenyl)-acetic acid methyl ester was substituted for (3,4-Dimethoxyphenyl)acetonitrile, dimethyl carbonate was substituted for 2-bromopropane and sodium hydride was substituted for NaHMDS. For Step 2, sodium hydride was substituted for NaHMDS.

Example 3

1b: Methyl 5-bromo-2-cyano-2-(3,4-dimethoxyphenyl)pentanoate

For Step 1, dimethyl carbonate was substituted for 2-bromopropane and sodium hydride was substituted for NaHMDS.

Example 4

1c: Ethyl 5-bromo-2-cyano-2-(3,4-dimethoxyphenyl)pentanoate

For Step 1, diethyl carbonate was substituted for 2-bromopropane and sodium hydride was substituted for NaHMDS.

Example 5

1d: Isopropyl 5-bromo-2-cyano-2-(3,4-dimethoxyphenyl)pentanoate

For Step 1, isopropyl chloroformate was substituted for 2-bromopropane.

Example 6

1e: Methyl 5-chloro-2-(3,4-dimethoxyphenyl)-2-isopropylpentanoate

For Step 1, (3,4-dimethoxy-phenyl)-acetic acid methyl ester was substituted for (3,4-Dimethoxyphenyl)acetonitrile, 2-iodopropane was substituted for 2-bromopropane and KHMDS was substituted for NaHMDS. For Step 2, 1-bromo-3-chloropropane was substituted for 1,3-dibromopropane.

Example 7

1g: 1-Ethyl 3-methyl 2-(3-bromopropyl)-2-(3,4-dimethoxyphenyl)malonate

For Step 1, (3,4-dimethoxy-phenyl)-acetic acid methyl ester was substituted for (3,4-Dimethoxyphenyl)acetonitrile, ethyl chloroformate was substituted for 2-bromopropane and lithium diisopropylamide (LDA) was substituted for NaHMDS. For Step 2, sodium hydride was substituted for NaHMDS.

Example 8

1b: Diethyl 2-(3-bromopropyl)-2-(3,4-dimethoxyphenyl)malonate

For Step 1, (3,4-dimethoxy-phenyl)-acetic acid ethyl ester was substituted for (3,4-Dimethoxyphenyl)acetonitrile, ethyl chloroformate was substituted for 2-bromopropane and lithium diisopropylamide (LDA) was substituted for NaHMDS. For Step 2, sodium hydride was substituted for NaHMDS.

Example 9

1i: 1-tert-butyl 3-methyl 2-(3-bromopropyl)-2-(3,4-dimethoxyphenyl)malonate

For Step 1, (3,4-dimethoxy-phenyl)-acetic acid methyl ester was substituted for (3,4-Dimethoxyphenyl)acetonitrile, di-tert-butyl dicarbonate was substituted for 2-bromopropane and LDA was substituted for NaHMDS. For Step 2, sodium hydride was substituted for NaHMDS.

Example 10

1j: 1-Isopropyl 3-methyl 2-(3-bromopropyl)-2-(3,4-dimethoxyphenyl)malonate

For Step 1, (3,4-dimethoxy-phenyl)-acetic acid methyl ester was substituted for (3,4-Dimethoxyphenyl)acetonitrile, isopropyl chloroformate was substituted for 2-bromopropane and LDA was substituted for NaHMDS. For Step 2, sodium hydride was substituted for NaHMDS.

Example 11

1k: Methyl 5-bromo-2-(3,4-dimethoxyphenyl)-2-methylpentanoate

For Step 1, (3,4-dimethoxy-phenyl)-acetic acid methyl ester was substituted for (3,4-Dimethoxyphenyl)acetonitrile and dimethyl sulfate was substituted for 2-bromopropane.

Example 12

1l: Ethyl 5-bromo-2-(3,4-dimethoxyphenyl)-2-methylpentanoate

For Step 1, (3,4-dimethoxy-phenyl)-acetic acid ethyl ester was substituted for (3,4-Dimethoxyphenyl)acetonitrile and dimethyl sulfate was substituted for 2-bromopropane.

Example 13

1m: Methyl 5-bromo-2-(3,4-dimethoxyphenyl)-2-ethylpentanoate

For Step 1, (3,4-dimethoxy-phenyl)-acetic acid methyl ester was substituted for (3,4-Dimethoxyphenyl)acetonitrile and diethyl sulfate was substituted for 2-bromopropane.

Example 14

1n: Methyl 4-(6-bromo-3-cyano-2-methylhexan-3-yl)benzoate

For Step 1, methyl 4-(cyanomethyl)benzoate was substituted for (3,4-Dimethoxyphenyl)acetonitrile. For Step 2, sodium hydride was substituted for NaHMDS.

Example 15

1o: Ethyl 5-bromo-2-(3,4-dimethoxyphenyl)-2-ethylpentanoate

For Step 1, (3,4-dimethoxy-phenyl)-acetic acid ethyl ester was substituted for (3,4-Dimethoxyphenyl)acetonitrile and diethyl sulfate was substituted for 2-bromopropane.

Example 16

1p: Isopropyl 5-bromo-2-(3,4-dimethoxyphenyl)-2-methylpentanoate

For Step 1, (3,4-dimethoxy-phenyl)-acetic acid isopropyl ester was substituted for (3,4-Dimethoxyphenyl)acetonitrile and dimethyl sulfate was substituted for 2-bromopropane.

Example 17

1q: Methyl 4-(5-bromo-2-cyano-1-methoxy-1-oxo-pentan-2-yl)benzoate

For Step 1, methyl 4-(cyanomethyl)benzoate was substituted for (3,4-Dimethoxyphenyl)acetonitrile and dimethyl carbonate was substituted for 2-bromopropane. For Step 2, sodium hydride was substituted for NaHMDS.

Example 18

1r: Methyl 3-(6-bromo-3-cyano-2-methylhexan-3-yl)benzoate

For Step 1, methyl 3-(cyanomethyl)benzoate was substituted for (3,4-Dimethoxyphenyl)acetonitrile and sodium hydride was substituted for NaHMDS. For Step 2, sodium hydride was substituted for NaHMDS.

Example 19

1s: Methyl 3-(5-bromo-2-cyano-1-methoxy-1-oxo-pentan-2-yl)benzoate

For Step 1, methyl 3-(cyanomethyl)benzoate was substituted for (3,4-Dimethoxyphenyl)acetonitrile and dimethyl carbonate was substituted for 2-bromopropane.

Example 20

1t: Ethyl 4-(6-bromo-3-cyano-2-methylhexan-3-yl)benzoate

Ethyl 4-(1-cyano-2-methylpropyl)benzoate was obtained by NaOH hydrolysis of methyl 4-(1-cyano-2-methylpropyl)benzoate (obtained as an intermediate in the transformations described in Example 14) and subsequent esterification by heating in ethanol and catalytic $H_2SO_4$. The ethyl ester was then subjected to the procedure of Method A, Step 2.

Example 21

1u: Isopropyl 4-(6-bromo-3-cyano-2-methylhexan-3-yl)benzoate

Isopropyl 4-(1-cyano-2-methylpropyl)benzoate was obtained by NaOH hydrolysis of methyl 4-(1-cyano-2-methylpropyl)benzoate (obtained as an intermediate in the transformations described in Example 14) and subsequent esterification by heating in 2-propanol and catalytic $H_2SO_4$. The isopropyl ester was then subjected to the procedure of Method A, Step 2.

For the Compounds Listed in Table 2

Example 22. Methyl 4-(2-(methylamino)ethyl)benzoate (2b)

To a solution of 2.02 g (10.0 mmol) of 4-(2-aminoethyl)benzoic acid hydrochloride in 25 mL of methanol was added 1.5 mL of $H_2SO_4$. The mixture was heated to reflux and became a homogeneous solution after 1 h. The solution was refluxed for about 16 h, cooled to 22° C. and concentrated to about 10 mL by evaporation. The solution was diluted with 100 mL of water, made basic with 1 N NaOH and extracted with 100 mL of dichloromethane (DCM). The aqueous layer was back-extracted with DCM (4×100 mL). The combined extracts were dried ($Na_2SO_4$) and evaporated to give methyl 4-(2-aminoethyl)benzoate as a colorless oil. The material was used directly in the subsequent transformation.

To a solution of methyl 4-(2-aminoethyl)benzoate in 30 mL of DCM at 0° C. was added 1.10 mL (6.31 mmol) of diisopropylethylamine (DIEA) followed by 0.850 mL (6.11 mmol) of trifluoroacetic anhydride. The reaction was allowed to warm to 22° C. and stirred for 2 h. The reaction was washed with 30 mL of saturated $NaHCO_3$. The aqueous solution was back-extracted with 30 mL of DCM and the combined organic extracts were dried ($Na_2SO_4$) and evaporated to give methyl 4-(2-(2,2,2-trifluoroacetamido)ethyl)benzoate as a solid. The material was further purified by flash chromatography on silica gel, eluting first with hexane and then gradually increasing to 20% ethyl acetate/hexane.

To a solution of 1.53 g (5.54 mmol) of methyl 4-(2-(2,2,2-trifluoroacetamido)ethyl)benzoate in 30 mL of dimethylformamide (DMF) at 0° C. was added 1.91. g (13.9 mmol) of potassium carbonate and 1.75 mL (27.7 mmol) of iodomethane. The reaction was warmed to 22° C. and left to stir for about 16 h. A white precipitate resulted which was collected. The solid was washed well with 100 mL of water to dissolve the potassium salts, collected and washed again with 50 mL of hexane. The resulting crude methyl 4-(2-(2,2,2-trifluoro-N-methylacetamido)ethyl)benzoate was used directly in the next step.

A solution of 0.80 g (5.5 mmol) of sodium hydride (60% mineral oil dispersion) dissolved in 20 mL of methanol was prepared and added to a separate solution of 1.05 g (3.64 mmol) of methyl 4-(2-(2,2,2-trifluoro-N-methylacetamido)ethyl)benzoate dissolved in 12 mL of THF at 0° C. The solution was warmed to 22° C. and stirred for about 36 h. Water was added (100 mL) and the solution was acidified to pH 1 with 1 N HCl. The mixture was washed with DCM (2×100 mL) and then basified with 1 N NaOH to pH 8-9. The aqueous solution was extracted with DCM (3×100 mL) and the organic extracts dried ($Na_2SO_4$) and evaporated to give 2b as a white solid which was used without further purification in the subsequent transformation.

Example 23

2c: Ethyl 4-(2-(methylamino)ethyl)benzoate

To a solution of 2.72 g (13.5 mmol) of 4-(2-aminoethyl) benzoic acid hydrochloride in 67.5 mL of 1 N NaOH and 30 mL of dioxane was added 3.24 g (14.9 mmol) of di-tert-butyl dicarbonate ($BOC_2O$) in 10 mL of dioxane at 22° C. The solution was stirred for 2 h at 22° C. and an additional 1.66 g (7.61 mmol) of $BOC_2O$ was added. After stirring another 30 min the reaction was poured into 250 mL of ice water and the mixture acidified with 1 N HCl to about pH 2, extracted with 250 mL of ethyl acetate, dried ($Na_2SO_4$) and evaporated to give a white solid. The solid was recrystallized from 50 mL of ethyl acetate to remove the excess $BOC_2O$ and to yield 4-(2-(tert-butoxycarbonylamino)ethyl) benzoic acid as a white solid.

To a solution of 1.96 g (7.39 mmol) of 4-(2-(tert-butoxycarbonylamino)ethyl) benzoic acid in 25 mL of DMF was added 4.43 g (32.1 mmol) of potassium carbonate and 3.00 mL (37.2 mmol) of iodoethane at 0° C. The mixture was warmed to 22° C. and stirred for about 16 h. The reaction was then diluted with 20 mL of water and 100 mL of saturated $NaHCO_3$. The mixture was extracted with DCM (3×200 mL) and the combined organics were washed with 100 mL of water, dried ($MgSO_4$) and evaporated to give ethyl 4-(2-(tert-butoxycarbonylamino)ethyl)benzoate as a sticky off-white solid.

Method B Step 1:

To a solution of 1.25 g (4.26 mmol) of ethyl 4-(2-(tert-butoxycarbonylamino)ethyl)benzoate in 40 mL of dry THF under a nitrogen atmosphere was added dropwise, 4.7 mL (4.7 mmol) of NaHMDS (1.0 M in THF) at 0° C. After stirring for 10 min, 0.50 mL (5.3 mmol) of dimethyl sulfate was added and the reaction was warmed to 22° C. and stirred for about 16 h. The reaction was quenched by adding 25 mL of saturated $NaHCO_3$ and the mixture was extracted with DCM (2×25 mL). The combined organic extracts were dried ($Na_2SO_4$) and evaporated and the residue was purified by flash chromatography on silica gel, eluting first with hexane and then gradually increasing to 10% ethyl acetate/hexane to give ethyl 4-(2-(tert-butoxycarbonyl(methyl)amino)ethyl) benzoate as a colorless oil.

Method B Step 2:

To a solution of 0.907 g (2.95 mmol) of ethyl 4-(2-(tert-butoxycarbonyl(methyl)amino) ethyl)benzoate in 10 mL of DCM at 0° C. was added 2.0 mL (26 mmol) of trifluoroacetic acid (TFA). The reaction was warmed to 22° C., stirred for 3 h and the solvents were then evaporated. The residue was partitioned between 100 mL of ethyl acetate and 100 mL of 1 N NaOH which had been saturated with NaCl. The aqueous layer was back-extracted with ethyl acetate (6×50 mL) and the combined organics were dried ($Na_2SO_4$) and evaporated to give 2c as a colorless oil.

Example 24

2d: Methyl 3-(2-(methylamino)ethyl)benzoate

To a solution of 5.71 g (24.9 mmol) of methyl 3-bromomethylbenzoate in 36 mL of methanol was added 2.11 g (32.4 mmol) of potassium cyanide. The mixture was refluxed for about 16 h, cooled to 22° C. and filtered. The filtrate was evaporated and the residue was purified by flash chromatography on silica gel, eluting first with hexane and then gradually increasing to 15% ethyl acetate/hexane to give methyl 3-(cyanomethyl)benzoate.

To a solution of 1.31 g (7.48 mmol) of methyl 3-(cyanomethyl)benzoate in 31 mL of THF stirred at −10° C. was slowly added 710 mg (18.7 mmol) of sodium borohydride followed by 1.44 mL (18.7 mmol) of trifluoroacetic acid. The mixture was warmed to 22° C. and stirred for about 16 h. About 100 ml. of water was carefully added to the mixture (gas evolution). The mixture was extracted with ethyl acetate (5×50 mL). The organic phase was washed with brine, dried ($Na_2SO_4$), filtered and evaporated to give methyl 3-(2-aminoethyl)benzoate which was used in the next step without purification.

Method C:

To 5.12 g (28.6 mmol) of methyl 3-(2-aminoethyl)benzoate in 71 mL tetrahydrofuran (THF) was added 7.48 g (34.3 mmol) of $BOC_2O$. The mixture was stirred for about 16 h at 22° C. and 100 mL of water was added. The mixture was extracted with ethyl acetate (2×100 mL) and the organic phase was washed with brine, dried ($Na_2SO_4$) and evaporated. The residue was purified by flash chromatography on silica gel, eluting first with hexane and then gradually increasing to 20% ethyl acetate/hexane to give methyl 3-(2-(tert-butoxycarbonylamino)ethyl)benzoate which was further converted to 2d in a manner analogous to Method B.

Example 25

2e: Ethyl 3-(2-(methylamino)ethyl)benzoate

To a solution of 1.90 g (10.6 mmol) of methyl 3-(2-aminoethyl)benzoate in 106 mL of 1 N NaOH and 50 mL of dioxane was added 3.47 g (15.9 mmol) of $BOC_2O$ in 10 mL of dioxane at 22° C. The solution was stirred for 2 h at 22° C. and then acidified to pH 2 by addition of 1 N HCl. The aqueous/organic mixture was saturated by stirring with solid NaCl and then extracted with DCM (5×100 mL). The combined organic extracts were dried ($Na_2SO_4$) and evaporated to give 3-(2-(tert-butoxycarbonylamino)ethyl)benzoic acid as a foamy white solid which was used subsequently without purification.

Transformation of 3-(2-(tert-butoxycarbonylamino)ethyl) benzoic acid to ethyl 3-(2-(tert-butoxycarbonylamino)ethyl) benzoate with iodoethane and potassium carbonate was accomplished in a manner analogous to that described in Example 23.

Transformation of ethyl 3-(2-(tert-butoxycarbonylamino) ethyl)benzoate to 2e was accomplished in a manner analogous to that described in Method B.

Example 26

2f: Isopropyl 3-(2-(methylamino)ethyl)benzoate

Transformation of 3-(2-(tert-butoxycarbonylamino)ethyl) benzoic acid to isopropyl 3-(2-(tert-butoxycarbonylamino) ethyl)benzoate was accomplished with 2-iodopropane and potassium carbonate in a manner analogous to that described in Example 23.

Transformation of isopropyl 3-(2-(tert-butoxycarbonylamino)ethyl)benzoate to 2f was accomplished in a manner analogous to that described in Method B.

Example 27

2g: Propyl 3-(2-(methylamino)ethyl)benzoate

To a solution of 0.580 g (1.98 mmol) of methyl 3-(2-(tert-butoxycarbonyl(methyl)amino)ethyl)benzoate in 5 mL of dioxane was added 10 mL of 1 N NaOH. The mixture was stirred at 22° C. for 2 h and then acidified to ca. pH 1 with 1 N HCl. The mixture was then extracted with DCM (4×25 mL), dried (Na$_2$SO$_4$) and evaporated to give 3-(2-(tert-butoxycarbonyl(methyl)amino)ethyl)benzoic acid as a foamy white solid which was subsequently used without purification.

Transformation of 3-(2-(tert-butoxycarbonyl(methyl) amino)ethyl)benzoic acid to propyl 3-(2-(tert-butoxycarbonyl(methyl)amino)ethyl)benzoate was accomplished with 1-iodopropane and potassium carbonate in a manner analogous to that described in Example 23.

Transformation of propyl 3-(2-(tert-butoxycarbonyl (methyl)amino)ethyl)benzoate to 2g was accomplished in a manner analogous to that described in Method B Step 2.

Example 28

2h: Methyl 2-methoxy-5-(2-(methylamino)ethyl)benzoate

To a solution of 1.01 g (6.09 mmol) of 5-formyl-2-hydroxybenzoic acid in 25 mL of acetone was added 4.25 g (30.5 mmol) of potassium carbonate and 1.15 mL (18.3 mmol) of iodomethane. The mixture was heated to reflux for about 16 h, cooled to 22° C. and filtered. The collected solid was washed with acetone. The filtrates were combined, evaporated and the residue purified by flash chromatography on silica gel eluting with a mixture of hexane and ethyl acetate to give methyl 5-formyl-2-methoxybenzoate as an off-white solid.

To a solution of 0.609 g (3.66 mmol) of 5-formyl-2-methoxybenzoate in 10 mL of acetic acid at 22° C. was added 2.2 mL (22 mmol) of n-butylamine followed by 0.337 mL (5.50 mmol) of nitromethane. The mixture was heated to reflux for 3 h, cooled to 22° C. and poured into 250 mL of water. A yellow precipitate resulted which dissolved when the mixture was extracted with 200 mL of ethyl acetate. The organic layer was washed with saturated NaHCO$_3$ (2×100 mL), dried (Na$_2$SO$_4$) and evaporated. The residue was purified by flash chromatography on silica gel eluting with a mixture of hexane and ethyl acetate to give methyl 2-methoxy-5-(2-nitrovinyl)benzoate.

To a solution of 0.429 g (1.81 mmol) of 2-methoxy-5-(2-nitrovinyl)benzoate in 18 mL of methanol was added 0.75 mL of 12 N HCl followed by 50 mg of 10% palladium on carbon. The mixture was stirred for 3 h under a balloon hydrogen atmosphere then degassed with nitrogen and filtered. Evaporation gave methyl 5-(2-aminoethyl)-2-methoxybenzoate hydrochloride as a sticky oil.

Transformation of methyl 5-(2-aminoethyl)-2-methoxybenzoate to 2h was accomplished in a manner analogous to that described in Method C and Method B.

Example 29

2i: Dimethyl 5-(2-(methylamino)ethyl)isophthalate

To a solution of 3.15 g (14.1 mmol) of dimethyl 5-(hydroxymethyl)isophthalate (prepared as described in Dimick et al., J. Am. Chem. Soc. (1999) 121, No. 44, 10286-10296) in 60 mL of DCM was added 7.34 g (84.4 mmol) of MnO$_2$. The mixture was stirred at reflux for about 16 h and an additional 3.5 g of MnO$_2$ was added. Refluxing was continued for another 6 h and the mixture was cooled, filtered through celite and evaporated to give dimethyl 5-formylisophthalate as a white solid which was used subsequently without purification.

To a solution of 2.45 g (11.0 mmol) of dimethyl 5-formylisophthalate in 30 mL of methanol was added 1.48 mL (27.6 mmol) of nitromethane and 1.53 mL (11.0 mmol) of triethylamine (TEA). The solution was stirred at 22° C. for about 16 h, evaporated then coevaporated with xylenes. The residue was purified by flash chromatography on silica gel, eluting first with 5% ethyl acetate/hexane and then gradually increasing to 20% ethyl acetate/hexane which gave dimethyl 5-(1-hydroxy-2-nitroethyl)isophthalate as a solid.

To a solution of 2.29 g (8.09 mmol) of dimethyl 5-(1-hydroxy-2-nitroethyl)isophthalate in 50 mL of DCM and 10 mL of acetic anhydride at 22° C. was added 100 mg of 4-dimethylaminopyridine. The solution was stirred at 22° C. for 1.5 h, evaporated and then coevaporated with xylenes (the material darkened slightly). The residue was partitioned between 100 mL of DCM and 50 mL of 1 N HCl. The organic layer was washed with water (50 mL), satd NaHCO$_3$, dried (Na$_2$SO$_4$) and evaporated. The resulting residue was purified by flash chromatography on silica gel eluting with DCM to give dimethyl 5-(2-nitrovinyl) isophthalate as a light yellow solid.

To a solution of 365 mg (1.38 mmol) of dimethyl 5-(2-nitrovinyl)isophthalate in 15 mL of methanol and 0.46 mL of 12 N HCl, was added 80 mg of 10% palladium on carbon. The mixture was stirred under a hydrogen balloon atmosphere for 7 h then filtered through celite and evaporated to give dimethyl 5-(2-aminoethyl)isophthalate hydrochloride as a white solid which was used as such immediately in the next step.

Transformation of dimethyl 5-(2-aminoethyl)isophthalate hydrochloride to 2i was accomplished in a manner analogous to Method C (using DMF instead of THF and adding TEA) followed by Method B.

Example 30

2j: Methyl 2-(4-(2-(methylamino)ethyl)phenoxy)acetate

Method D:

To a solution of 1.00 g (5.75 mmol) of 4-(2-aminoethyl) phenol in 5 mL of dioxane at 22° C. was added 2 mL of 1 N NaOH followed by 1.88 g (8.62 mmol) of $BOC_2O$ dissolved in 2 mL of dioxane. The mixture was stirred at 22° C. for 2 h and then neutralized by adding 25 mL of saturated $NaHCO_3$ which resulted in a pH of about 7.5-8. The aqueous layer was separated and extracted with DCM (3×50 mL). The organics were combined, dried ($Na_2SO_4$) and evaporated. The residue was purified by flash chromatography on silica gel eluting with a mixture of hexane and ethyl acetate to give tert-butyl 4-hydroxyphenethylcarbamate as a colorless oil.

Method E:

To a solution of 1.11 g (4.70 mmol) of tert-butyl 4-hydroxyphenethylcarbamate in 20 mL of DMF at 22° C. was added 1.3 g (9.4 mmol) of potassium carbonate and 0.700 mL (5.87 mmol) of benzyl bromide. The mixture was stirred for about 16 h at 22° C., diluted with 100 mL of water and extracted with ethyl acetate (3×75 mL). The organic layers were combined, washed with 100 mL of 1 N HCl, dried ($Na_2SO_4$), and evaporated.

The residue was purified by flash chromatography on silica gel eluting with a mixture of hexane and ethyl acetate to give tert-butyl 4-(benzyloxy)phenethylcarbamate as an oil which later solidified under vacuum.

Transformation of tert-butyl 4-(benzyloxy)phenethylcarbamate to tert-butyl 4-(benzyloxy)phenethyl(methyl)carbamate was accomplished in a manner analogous to Method B Step 1.

To a solution of 1.13 g (3.32 mmol) of tert-butyl 4-(benzyloxy)phenethyl(methyl)carbamate in 15 mL of methanol was added 35 mg of 10% palladium on carbon. The reaction was stirred under a hydrogen balloon atmosphere for 6 h, filtered through celite and evaporated to give tert-butyl 4-hydroxyphenethyl(methyl)carbamate as a colorless oil which was subsequently used without purification.

Transformation of tert-butyl 4-hydroxyphenethyl(methyl) carbamate to 2j was accomplished in a manner analogous to Method E (using methyl 2-bromoacetate instead of benzyl bromide and acetone in place of DMF) followed by Method B Step 2.

Example 31

2k: Ethyl 2-(4-(2-(methylamino)ethyl)phenoxy)acetate

Transformation of tert-butyl 4-hydroxyphenethyl(methyl) carbamate to 2k was accomplished in a manner analogous to Method E (using ethyl 2-bromoacetate instead of benzyl bromide and acetone in place of DMF) followed by Method B Step 2.

Example 32

2l: Methyl 2-(3-(2-(methylamino)ethyl)phenoxy)acetate

Transformation of 2-(3-methoxyphenyl)ethanamine to tert-butyl 3-methoxyphenethyl(methyl)carbamate was accomplished in a manner analogous to Method D followed by Method B Step 1.

A solution of 3.16 g (11.9 mmol) of tert-butyl 3-methoxyphenethyl(methyl)carbamate in 10 mL of 48% aqueous HBr was prepared and heated to 110° C. for about 16 h. The solution was cooled to 0° C. and carefully neutralized to slightly basic pH with 10 N NaOH. To the cooled mixture was added 3.90 g (17.8 mmol) of $BOC_2O$ in 10 mL of dioxane. The reaction was warmed to 22° C., stirred for 2 h and 1 N HCl was added carefully to adjust to about pH 7. The mixture was partitioned between 100 mL of saturated $NaHCO_3$ and ethyl acetate. The organic layer was dried ($Na_2SO_4$) and evaporated. The residue was purified by flash chromatography on silica gel eluting with a mixture of hexane and ethyl acetate to give tert-butyl 3-hydroxyphenethyl(methyl)carbamate.

Transformation of tert-butyl 3-hydroxyphenethyl(methyl) carbamate to 2l was accomplished in a manner analogous to Method E (using methyl 2-bromoacetate instead of benzyl bromide and acetone in place of DMF) followed by Method B Step 2.

Example 33

2m: Butyl 3-(2-(methylamino)ethyl)benzoate

Transformation of 3-(2-(tert-butoxycarbonyl (methyl)amino)ethyl)benzoic acid to butyl 3-(2-(tert-butoxycarbonyl (methyl)amino)ethyl)benzoate was accomplished with 1-iodobutane and potassium carbonate in a manner analogous to that described in Example 23. Transformation of butyl 3-(2-(tert-butoxycarbonyl(methyl) amino)ethyl)benzoate to 2m was accomplished in a manner analogous to that described in Method B Step 2.

Example 34

2n: 2-Methoxyethyl 3-(2-(methylamino)ethyl)benzoate

Transformation of 3-(2-(tert-butoxycarbonyl(methyl) amino)ethyl)benzoic acid to 2-methoxyethyl 3-(2-(tert-butoxycarbonyl(methyl)amino) ethyl)benzoate was accomplished with 1-bromo-2-methoxyethane and potassium carbonate in a manner analogous to that described in Example 23.

Transformation of 2-methoxyethyl 3-(2-(tert-butoxycarbonyl(methyl)amino)ethyl)benzoate to 2n was accomplished in a manner analogous to that described in Method B Step 2.

Example 35

2o: Methyl 2-(3-(2-(methylamino)ethyl)phenyl)acetate

Conversion of 2-(3-bromophenyl)ethanamine to tert-butyl 3-bromophenethyl(methyl)carbamate was accomplished in a manner analogous to Method C followed by Method B, Step 1.

To a solution of 200 mg (1.51 mmol) of dimethylmalonate in 4 mL of dioxane at 22° C. was added 61.0 mg (1.53 mmol) of sodium hydride (60% dispersion in mineral oil). After the mixture was stirred for 10 minutes, 61 µL (0.06 mmol) of tri-tert-butylphosphine (1 M in toluene), 17.4 mg (0.030 mmol) of bis(dibenzylideneacetone)palladium(0) and 333 mg (1.06 mmol) of tert-butyl 3-bromophenethyl(methyl) carbamate were added sequentially and the mixture heated to reflux for about 16 h under nitrogen. After cooling to 22°

C., the solvent was evaporated and the residue partitioned between saturated NH₄Cl and ethyl acetate. The organic layer was washed with brine, dried (Na₂SO₄), filtered and evaporated to give dimethyl 2-(3-(2-(tert-butoxycarbonyl (methyl)amino)ethyl)phenyl)malonate which was used directly in the next step without further purification.

To 429 µL (10.6 mmol) of methanol was slowly added 85 mg (2.1 mmol) of sodium hydride (60% dispersion in mineral oil). This mixture was then added to a separate solution of 387 mg (1.06 mmol) of dimethyl 2-(3-(2-(tert-butoxycarbonyl(methyl)amino)ethyl)phenyl)malonate in 5 mL of tetrahydrofuran. The resulting solution was refluxed for 2 h then cooled to 22° C. An additional 85 mg of NaH in 429 ml of methanol was added and the solution was again heated to reflux for about 16 h. The solvent was evaporated and the residue partitioned between saturated NH₄Cl and ethyl acetate. The organic layer was washed with brine, dried (Na₂SO₄), filtered and evaporated. The residue was purified by flash chromatography on silica gel, eluting first with hexane and then gradually increasing to 15% ethyl acetate/hexane to give methyl 2-(3-(2-(tert-butoxycarbonyl (methyl)amino)ethyl)phenyl)acetate.

Conversion of methyl 2-(3-(2-(tert-butoxycarbonyl (methyl)amino)ethyl)phenyl)acetate to 2o was accomplished in a manner analogous to Method B, Step 2.

Preparation of Compounds of Formula 1 Exemplified in this Invention:

Preparation of compounds of Formula 1 exemplified in this invention was accomplished by the general procedure of Method F. The conditions of Method F are suitable for the synthesis of the compounds described in the below Examples. In some cases, the reaction was conducted without evaporation of THF or other suitable non-reactive organic solvents were used instead. In some cases a few crystals of sodium iodide were added to help accelerate the reaction or a base such as DIEA was added. These variations did not significantly alter the outcome of the general procedure.

Example 36

Ethyl 4-(2-((4-cyano-4-(3,4-dimethoxyphenyl)-5-methylhexyl)(methyl)amino) ethyl)benzoate (3r)

Method F:

A solution of 0.326 g (0.961 mmol) of 1f in 1 mL of THF and a separate solution of 0.292 g (1.41 mmol) of 2c in 1 mL of THF were combined. The resulting solution was heated in a 90° C. oil bath and the THF was evaporated under a slow stream of nitrogen. The resulting mixture was stirred under nitrogen at 85° C. for 18 h, cooled to 22° C. and partitioned between saturated NaHCO₃ and ethyl acetate. The organic layer was dried (Na₂SO₄) and evaporated and the residue purified by flash chromatography on silica gel, eluting first with DCM and then gradually increasing to 2% methanol/DCM to give 3r as a colorless oil; MS found M+H=467. The oxalate salt of 3r was recrystallized from ethyl acetate; mp 111-112° C.

Unless otherwise indicated, the following Examples were prepared by procedures analogous to Method F:

Example 37

3a: Dimethyl 2-(3-((3,4-dimethoxyphenethyl) (methyl)amino)propyl)-2-(3,4-dimethoxyphenyl) malonate Reaction of 1a with 2a produced 3a. MS found M+H=504. The oxalate salt of 3a was recrystallized from ethyl acetate; mp 165-166° C.

Example 38

3b: Methyl 5-((3,4-dimethoxyphenethyl)(methyl) amino)-2-(3,4-dimethoxyphenyl)pentanoate To a solution of 0.349 g (0.694 mmol) of 3a in 20 mL of THF at 22° C. was added 0.281 mL (6.94 mmol) of methanol followed by 56 mg (1.39 mmol) of NaH (60% dispersion in mineral oil). The reaction was refluxed for 1 h, cooled to 22° C. and diluted with 100 mL of DCM. The mixture was washed with 50 mL of saturated NaHCO₃, 50 mL of water, dried, and evaporated to give an oil. The oil was purified by flash chromatography on silica gel, eluting first with 2% methanol/DCM and then gradually increasing to 4% methanol/DCM to give 3b as a colorless oil; MS found M+H=446. The oxalate salt of 3r was recrystallized from ethyl acetate; mp 112-113.5° C.

Example 39

3c: Methyl 2-cyano-5-((3,4-dimethoxyphenethyl) (methyl)amino)-2-(3,4-dimethoxyphenyl)pentanoate Reaction of 1b with 2a produced 3c. MS found M+H=471. The oxalate salt of 3c was recrystallized from ethyl acetate; mp 129-130° C.

Example 40

3d: Ethyl 2-cyano-5-((3,4-dimethoxyphenethyl) (methyl)amino)-2-(3,4-dimethoxyphenyl)pentanoate Reaction of 1c with 2a produced 3d. MS found M+H=485. The oxalate salt of 3d was recrystallized from ethyl acetate; mp 77-78° C.

Example 41

3e: Isopropyl 2-cyano-5-((3,4-dimethoxyphenethyl) (methyl)amino)-2-(3,4-dimethoxyphenyl)pentanoate Reaction of 1d with 2a produced 3e. MS found M+H=499. The oxalate salt of 3e was recrystallized from ethyl acetate; mp 66-67° C.

Example 42

3f: Methyl 5-((3,4-dimethoxyphenethyl)(methyl) amino)-2-(3,4-dimethoxyphenyl)-2-isopropylpentanoate Reaction of 1e with 2a produced 3f. MS found M+H=488. The oxalate salt of 3f was recrystallized from ethyl acetate; mp 158-159° C.

Example 43

3g: Methyl 4-(2-((4-cyano-4-(3,4-dimethoxyphenyl)-5-methylhexyl)(methyl)amino)ethyl)benzoate Reaction of 1f with 2b produced 3g. MS found M+H=453. The oxalate salt of 3g was recrystallized from ethyl acetate; mp 130-131° C.

Example 44

3h: Methyl 4-(2-((4-(3,4-dimethoxyphenyl)-4-(methoxycarbonyl)-5-methylhexyl)(methyl)amino)ethyl)benzoate Reaction of 1e with 2b produced 3h. MS found M+H=486. The oxalate salt of 3h was recrystallized from ethyl acetate; mp 129-131° C.

Example 45

3l: Methyl 4-(2-((4-cyano-4-(3,4-dimethoxyphenyl)-5-methoxy-5-oxopentyl)(methyl)amino)ethyl)benzoate Reaction of 1b with 2b produced 3i. MS found M+H=469. The oxalate salt of 3i was recrystallized from ethyl acetate; mp 80-83° C.

Example 46

3j: 1-Ethyl 3-methyl 2-(3-((3,4-dimethoxyphenethyl)(methyl)amino)propyl)-2-(3,4-dimethoxyphenyl)malonate Reaction of 1g with 2a produced 3j. MS found M+H=518. The oxalate salt of 3j was recrystallized from isopropanol/ether; mp 146-149° C.

Example 47

3k: Diethyl 2-(3-((3,4-dimethoxyphenethyl)(methyl)amino)propyl)-2-(3,4-dimethoxyphenyl)malonate Reaction of 1h with 2a produced 3k. MS found M+H=532. The oxalate salt of 3k was recrystallized from ethyl acetate/ether; mp 101-104° C.

Example 48

3l: 1-tert-Butyl 3-methyl 2-(3-((3,4-dimethoxyphenethyl)(methyl)amino)propyl)-2-(3,4-dimethoxyphenyl)malonate Reaction of 1i with 2a produced 3l. MS found M+H=546. The oxalate salt of 3l was recrystallized from ethyl acetate/hexane; mp 161-163° C.

Example 49

3m: 1-Isopropyl 3-methyl 2-(3-((3,4-dimethoxyphenethyl)(methyl)amino)propyl)-2-(3,4-dimethoxyphenyl)malonate Reaction of 1j with 2a produced 3m. MS found M+H=532. The oxalate salt of 3m was recrystallized from methanol/ether; mp 157-159° C.

Example 50

3n: Ethyl 4-(2-((4-cyano-4-(3,4-dimethoxyphenyl)-5-methoxy-5-oxopentyl)(methyl)amino)ethyl)benzoate Reaction of 1b with 2c produced 3n. MS found M+H=483. The oxalate salt of 3n was recrystallized from ethyl acetate; mp 88-89° C.

Example 51

3o: Methyl 3-(2-((4-cyano-4-(3,4-dimethoxyphenyl)-5-methylhexyl)(methyl)amino)ethyl)benzoate Reaction of 1f with 2d produced 3o. MS found M+H=453. The oxalate salt of 3o was recrystallized from ethyl acetate; mp 135-136° C.

Example 52

3p: Methyl 4-(2-((4-cyano-4-(3,4-dimethoxyphenyl)-5-ethoxy-5-oxopentyl)(methyl)amino)ethyl)benzoate Reaction of 1c with 2b produced 3p. MS found M+H=483. The oxalate salt of 3p was recrystallized from ethyl acetate; mp 75-77° C.

Example 53

3q: Ethyl 4-(2-((4-cyano-4-(3,4-dimethoxyphenyl)-5-ethoxy-5-oxopentyl)(methyl)amino)ethyl)benzoate Reaction of 1c with 2c produced 3q. MS found M+H=497. The oxalate salt of 3q was recrystallized from ethyl acetate; mp 83-84° C.

Example 54

3r: Ethyl 4-(2-((4-cyano-4-(3,4-dimethoxyphenyl)-5-methylhexyl)(methyl)amino)ethyl)benzoate Reaction of 1f with 2c produced 3r. MS found M+H=467. The oxalate salt of 3r was recrystallized from ethyl acetate; mp 111-112° C.

Example 55

3s: Methyl 5-((3,4-dimethoxyphenethyl)(methyl)amino)-2-(3,4-dimethoxyphenyl)-2-methylpentanoate Reaction of 1k with 2a produced 3s. MS found M+H=460. The oxalate salt of 3s was recrystallized from ethyl acetate; mp 88-89° C.

Example 56

3t: Methyl 3-(2-((4-cyano-4-(3,4-dimethoxyphenyl)-5-methoxy-5-oxopentyl)(methyl)amino)ethyl)benzoate Reaction of 1b with 2d produced 3t. MS found M+H=469. The oxalate salt of 3t was recrystallized from ethyl acetate; mp 94-95° C.

Example 57

3u: Methyl 3-(2-((4-cyano-4-(3,4-dimethoxyphenyl)-5-ethoxy-5-oxopentyl)(methyl)amino)ethyl)benzoate Reaction of 1c with 2d produced 3u. MS found M+H=483. The oxalate salt of 3u was recrystallized from ethyl acetate; mp 89-91° C.

Example 58

3v: Ethyl 5-((3,4-dimethoxyphenethyl)(methyl)amino)-2-(3,4-dimethoxyphenyl)-2-methylpentanoate Reaction of 1l with 2a produced 3v. MS found M+H=474. The oxalate salt of 3v was recrystallized from ethyl acetate; mp 118-121° C.

Example 59

3w: Ethyl 4-(2-((4-(3,4-dimethoxyphenyl)-4-(methoxycarbonyl)-5-methylhexyl)(methyl)amino)ethyl)benzoate Reaction of 1e with 2c produced 3w. MS found M+H=500. The oxalate salt of 3w was recrystallized from ethyl acetate; mp 121-123° C.

Example 60

3x: Methyl 5-((3,4-dimethoxyphenethyl)(methyl)amino)-2-(3,4-dimethoxyphenyl)-2-ethylpentanoate Reaction of 1m with 2a produced 3x. MS found M+H=474. The oxalate salt of 3x was recrystallized from methanol/ethyl acetate; mp 148-150° C.

Example 61

3y: Methyl 4-(3-cyano-6-((3,4-dimethoxyphenethyl)(methyl)amino)-2-methylhexan-3-yl)benzoate Reaction of 1n with 2a produced 3y. MS found M+H=453. The oxalate salt of 3y was recrystallized from methanol/ether; mp 179-182° C.

Example 62

3z: Ethyl 3-(2-((4-cyano-4-(3,4-dimethoxyphenyl)-5-methylhexyl)(methyl)amino)ethyl)benzoate Reaction of 1f with 2e produced 3z. MS found M+H=467. The oxalate salt of 3z was recrystallized from ethyl acetate; mp 128-129° C.

Example 63

3aa: Ethyl 5-((3,4-dimethoxyphenethyl)methyl)amino)-2-(3,4-dimethoxyphenyl)-2-ethylpentanoate Reaction of 1o with 2a produced 3aa. MS found M+H=488. The oxalate salt of 3aa was recrystallized from methanol/ethyl acetate; mp 122-124° C.

Example 64

3ab: Isopropyl 5-((3,4-dimethoxyphenethyl)(methyl)amino)-2-(3,4-dimethoxyphenyl)-2-methylpentanoate Reaction of 1p with 2a produced 3ab. MS found M+H=488. The oxalate salt of 3ab was recrystallized from methanol/ethyl acetate; mp 85-87° C.

Example 65

3ac: Methyl 4-(2-cyano-5-((3,4-dimethoxyphenethyl)(methyl)amino)-1-methoxy-1-oxopentan-2-yl)benzoate Reaction of 1q with 2a produced 3ac. MS found M+H=469. The oxalate salt of 3ac was recrystallized from methanol/ether; mp 133-136° C.

Example 66

3ad: Methyl 3-(3-cyano-6-((3,4-dimethoxyphenethyl)(methyl)amino)-2-methylhexan-3-yl)benzoate Reaction of 1r with 2a produced 3ad. MS found M+H=453. The oxalate salt of 3ad was recrystallized from methanol/ether; mp 158-159° C.

Example 67

3ae: Isopropyl 3-(2-((4-cyano-4-(3,4-dimethoxyphenyl)-5-methylhexyl)(methyl)amino)ethyl)benzoate Reaction of 1f with 2f produced 3ae. MS found M+H=481. The oxalate salt of 3ae was recrystallized from ethyl acetate; mp 130-132° C.

Example 68

3af: Propyl 3-(2-((4-cyano-4-(3,4-dimethoxyphenyl)-5-methylhexyl)(methyl)amino)ethyl)benzoate Reaction of 1f with 2g produced 3af. MS found M+H=481. The oxalate salt of 3af was recrystallized from ethyl acetate; mp 110-114° C.

Example 69

3ag: Methyl 5-(2-((4-cyano-4-(3,4-dimethoxyphenyl)-5-methylhexyl)(methyl)amino)ethyl)-2-methoxybenzoate Reaction of 1f with 2h produced 3ag. MS found M+H=483. The oxalate salt of 3ag was recrystallized from ethyl acetate; mp 76-81° C.

Example 70

3ah: Methyl 3-(2-cyano-5-((3,4-dimethoxyphenethyl)(methyl)amino)-1-methoxy-1-oxopentan-2-yl)benzoate Reaction of 1s with 2a produced 3ah. MS found M+H=469. The oxalate salt of 3ah was recrystallized from methanol/ether; mp 132-139° C.

Example 71

3ai: Dimethyl 5-(2-((4-cyano-4-(3,4-dimethoxyphenyl)-5-methylhexyl)methyl)amino)ethyl)isophthalate Reaction of 1f with 2i produced 3ai. MS found M+H=511. The oxalate salt of 3ai was recrystallized from hexane/ethyl acetate; mp 100-103° C.

Example 72

3aj: Methyl 3-(2-((4-(3,4-dimethoxyphenyl)-4-(methoxycarbonyl)-5-methylhexyl)(methyl)amino)ethyl)benzoate Reaction of 1e with 2d produced 3aj. MS found M+H=486. The oxalate salt of 3aj was recrystallized from ethyl acetate; mp 87-90° C.

Example 73

3ak: Methyl 2-(4-(2-((4-cyano-4-(3,4-dimethoxyphenyl)-5-methylhexyl)(methyl)amino)ethyl)phenoxy)acetate Reaction of 1f with 2j produced 3ak. MS found M+H=483. The oxalate salt of 3ak was recrystallized from ethyl acetate.

Example 74

3al: Ethyl 2-(4-(2-((4-cyano-4-(3,4-dimethoxyphenyl)-5-methylhexyl)methyl)amino)ethyl)phenoxy)acetate Reaction of 1f with 2k produced 3al. MS found M+H=497. The oxalate salt of 3al was recrystallized from ethyl acetate.

Example 75

3am: Methyl 3-(3-cyano-6-((4-(methoxycarbonyl)phenethyl)(methyl)amino)-2-methylhexan-3-yl)benzoate Reaction of 1r with 2b produced 3am. MS found M+H=451. The oxalate salt of 3am was recrystallized from methanol/ether; mp 108-112° C.

Example 76

3an: Ethyl 4-(3-cyano-6-((3,4-dimethoxyphenethyl)(amino)-2-methylhexan-3-yl)benzoate Reaction of 1t with 2a produced 3an. MS found M+H=467. The oxalate salt of 3an was recrystallized from methanol/ether; mp 159-163° C.

Example 77

3ao: Isopropyl 4-(3-cyano-6-((3,4-dimethoxyphenethyl)(methyl)amino)-2-methylhexan-3-yl)benzoate Reaction of 1u with 2a produced 3ao. MS found M+H=481. The oxalate salt of 3ao was recrystallized from methanol/ether; mp 165-167° C.

Example 78

3ap: Methyl 3-(2-((4-cyano-4-(3-(methoxycarbonyl)phenyl)-5-methylhexyl)(methyl)amino)ethyl)benzoate Reaction of 1r with 2d produced 3ap. MS found M+H=451. The oxalate salt of 3ap was recrystallized from methanol/ether; mp 129-136° C.

Example 79

3aq: Methyl 2-(3-(2-((4-cyano-4-(3,4-dimethoxyphenyl)-5-methylhexyl)amino)ethyl)phenoxy)acetate Reaction of 1f with 2l produced 3aq. MS found M+H=483. The oxalate salt of 3aq was recrystallized from methanol/ether; mp 96-100° C.

Example 80

3ar: Butyl 3-(2-((4-cyano-4-(3,4-dimethoxyphenyl)-5-methylhexyl)(methyl)amino)ethyl)benzoate Reaction of 1f with 2m produced 3ar. MS found M+H=495. The oxalate salt of 3ar was recrystallized from methanol/ether; mp 97-103° C.

Example 81

3as: 2-Methoxyethyl 3-(2-((4-cyano-4-(3,4-dimethoxyphenyl)-5-methylhexyl)(methyl)amino)ethyl)benzoate Reaction of 1f with 2n produced 3as. MS found M+H=497. The oxalate salt of 3ar was recrystallized from methanol/ether.

Example 82

3at: Methyl 2-(3-(2-((4-cyano-4-(3,4-dimethoxyphenyl)-5-methylhexyl)(methyl)amino)ethyl)phenyl)acetate Reaction of 1f with 2o produced 3at. MS found M+H=467. The oxalate salt of 3at was recrystallized from ethyl acetate; mp 77-82° C.

Example 83

3au: Methyl 2-(2-((4-cyano-4-(3,4-dimethoxyphenyl)-5-methylhexyl)(methyl)amino)ethyl)benzoate Reaction of 1f with N-methyl-2-phenylethanamine produced 2-(3,4-dimethoxyphenyl)-2-isopropyl-5-(methyl(phenethyl)amino)pentanenitrile which was further reacted in a manner analogous to the procedure reported in Liang, C. D. et al., Tetrahedron Lett., (1986) 27, 1971-1974.

To 331 mg (0.839 mmol) of 2-(3,4-dimethoxyphenyl)-2-isopropyl-5-(methyl(phenethyl)amino)pentanenitrile in 8.3 mL of benzene was added 226 mg (1.01 mmol) of palladium (II)acetate and the mixture was stirred for 72 h at 22° C. under nitrogen. The solution was transferred into a pressure flask, 10 mL of methanol was added and the mixture was treated with carbon monoxide at 40 psi for 24 h. After addition of 175 μL (1.26 mmol) of triethylamine, the mixture was filtered through a pad of celite and evaporated to give a crude mixture of 3au and 2-(3,4-dimethoxyphenyl)-2-isopropyl-5-(methyl(phenethyl)amino)pentanenitrile. In order to afford purification, a solution of 57 mg of the crude product was dissolved in 1 mL of methanol and treated with 63 µL of 10 N NaOH. After stirring for 1 h at 22° C., an additional 126 µL of 10 N NaOH and 2 mL of methanol was added. The solution was heated to 50° C. then cooled to 22° C., evaporated and partitioned between ether and 0.5 N NaOH. The aqueous layer was acidified to about pH 6 with 12 N HCl then extracted with ethyl acetate (3x). The combined organic layers were dried ($Na_2SO_4$) and evaporated to give 2-(2-((4-cyano-4-(3,4-dimethoxyphenyl)-5-methylhexyl)(methyl)amino)ethyl)benzoic acid. The carboxylic acid was esterified by treating with 44 mg (0.24 mmol) of carbonyldiimidazole in 1 mL of THF for 3 h at 22° C. followed by addition of 8 mL of methanol and continued stirring for about 16 hours at 22° C. The solvent was evaporated and the residue was purified by flash chromatography on silica gel, eluting first with dichloromethane and then gradually increasing to 3% methanol/dichloromethane to give 3au. MS found M+H=453. Substitution of the ester group in the indicated ortho-position of the phenyl ring was confirmed by $^1$H NMR analysis.

Example 84. Calcium Channel Binding Data

Calcium channel binding inhibition constants ($K_i$) were determined as follows.

Whole brain membranes of male Wistar derived rats weighing 175±25 g were prepared in HEPES buffer pH 7.4. A 10 mg aliquot was incubated with, for example, 0.4 nM [$^3$H](−)-Desmethoxyverapamil (D-888) (Amersham, TRK-834) for 60 minutes at 25° C. Non-specific binding was estimated in the presence of 10 µM D-600 (Sigma, M-115). Membranes were filtered and washed, the filters are then counted to determine [$^3$H](−)-Desmethoxyverapamil (D-888) specifically bound. All determinations were performed in duplicate. Specific binding was determined as the difference of total and nonspecific binding. The $K_i$ values were calculated using the equation of Cheng and Prusoff (Cheng, Y. et al. Biochem. Pharmacol. (1973) 22, 3099-3018) using the observed $IC_{50}$ of the tested compound, the concentration of the radioligand employed in the assay, and the historical values for the $K_d$ of the ligand (obtained experimentally at MDS Pharma Services).

The same method was used to determine the $K_i$ for the compounds listed in Table 4.

TABLE 4

| Compound # | Structure | $K_i$ (µM) Ca Channel |
|---|---|---|
| 3a-oxalate | [structure] | ++ |
| 3b-oxalate | [structure] | -- |

TABLE 4-continued
| Compound # | Structure | $K_i$ (μM) Ca Channel |
|---|---|---|
| verapamil-oxalate | 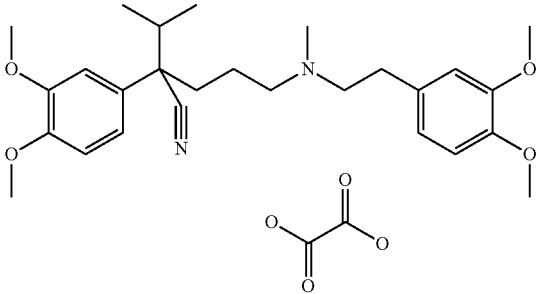 [SMILES: COc1ccc(CCN(C)CCCC(C#N)(c2ccc(OC)c(OC)c2)C(C)C)cc1OC ; O=C(O)C(=O)O] | ++++ |
| verapamil-HCl | 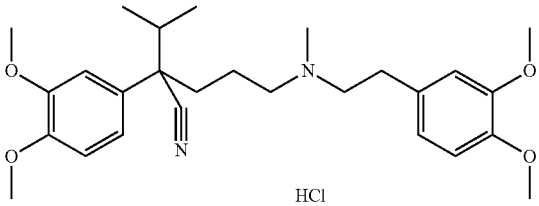 [SMILES: COc1ccc(CCN(C)CCCC(C#N)(c2ccc(OC)c(OC)c2)C(C)C)cc1OC ; Cl] | ++++ |
| 3c-oxalate | 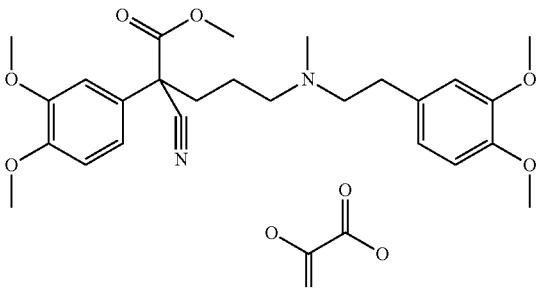 | +++ |
| 3d-oxalate | 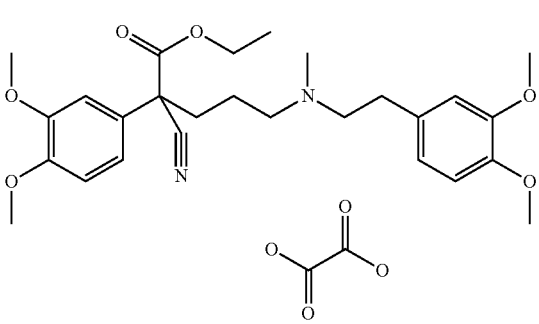 [SMILES: CCOC(=O)C(C#N)(CCCN(C)CCc1ccc(OC)c(OC)c1)c1ccc(OC)c(OC)c1 ; O=C(O)C(=O)O] | +++ |
| 3e-oxalate | 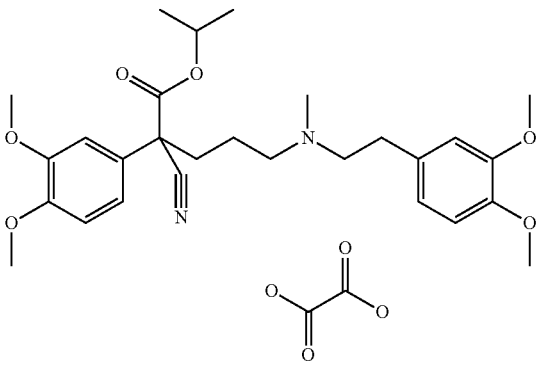 [SMILES: COc1ccc(CCN(C)CCCC(C#N)(C(=O)OC(C)C)c2ccc(OC)c(OC)c2)cc1OC ; O=C(O)C(=O)O] | +++ |

TABLE 4-continued

| Compound # | Structure | $K_i$ (μM) Ca Channel |
|---|---|---|
| 3f-oxalate | 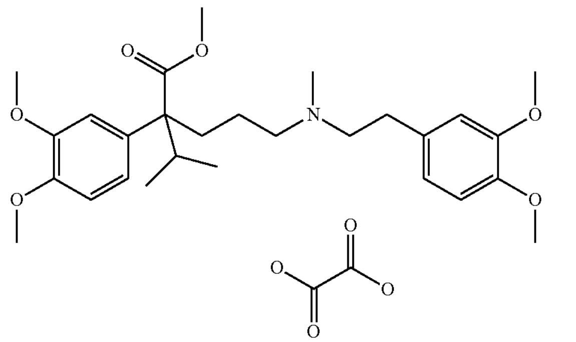 [SMILES: COC(=O)C(CCCN(C)CCc1ccc(OC)c(OC)c1)(c1ccc(OC)c(OC)c1)C(C)C ; O=C(O)C(=O)O] | +++ |
| 3g-oxalate | 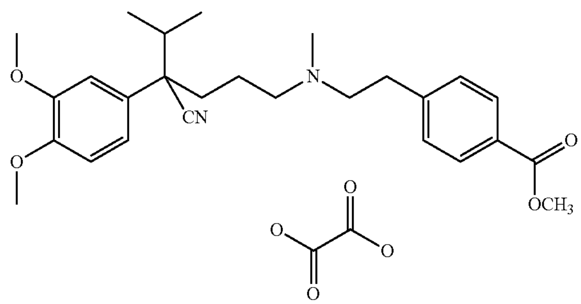 [SMILES: COC(=O)c1ccc(CCN(C)CCCC(C#N)(c2ccc(OC)c(OC)c2)C(C)C)cc1 ; O=C(O)C(=O)O] | +++ |
| 3h-oxalate | 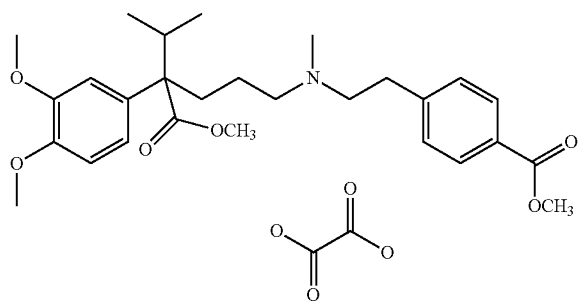 [SMILES: COC(=O)c1ccc(CCN(C)CCCC(C(=O)OC)(c2ccc(OC)c(OC)c2)C(C)C)cc1 ; O=C(O)C(=O)O] | +++ |
| 3i-oxalate | 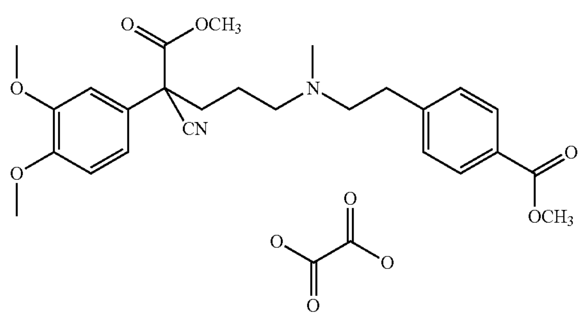 [SMILES: COC(=O)c1ccc(CCN(C)CCCC(C#N)(C(=O)OC)c2ccc(OC)c(OC)c2)cc1 ; O=C(O)C(=O)O] | ++ |
| 3j-oxalate | 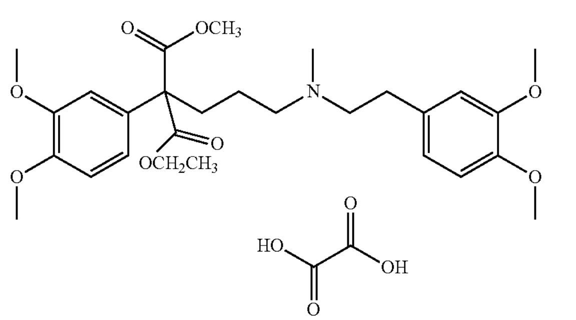 [SMILES: CCOC(=O)C(CCCN(C)CCc1ccc(OC)c(OC)c1)(C(=O)OC)c1ccc(OC)c(OC)c1 ; O=C(O)C(=O)O] | ++ |

TABLE 4-continued

| Compound # | Structure | $K_i$ (μM) Ca Channel |
|---|---|---|
| 3k-oxalate | 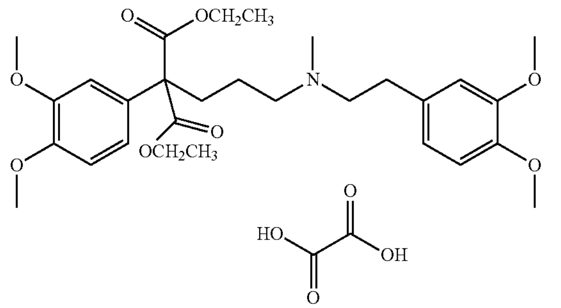 [SMILES: CCOC(=O)C(CCCN(C)CCc1ccc(OC)c(OC)c1)(C(=O)OCC)c1ccc(OC)c(OC)c1 ; O=C(O)C(=O)O] | + |
| 3l-oxalate | 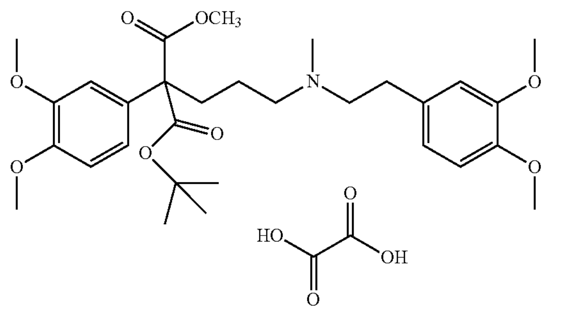 [SMILES: COC(=O)C(CCCN(C)CCc1ccc(OC)c(OC)c1)(C(=O)OC(C)(C)C)c1ccc(OC)c(OC)c1 ; O=C(O)C(=O)O] | +++ |
| 3m-TFA | 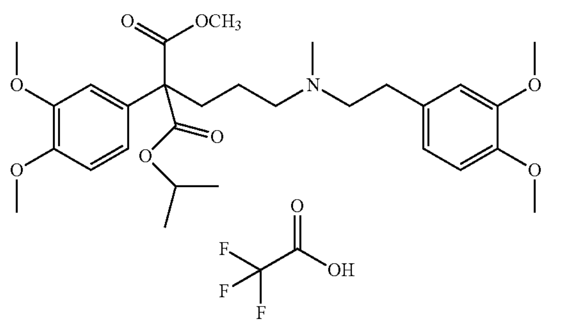 [SMILES: COC(=O)C(CCCN(C)CCc1ccc(OC)c(OC)c1)(C(=O)OC(C)C)c1ccc(OC)c(OC)c1 ; O=C(O)C(F)(F)F] | +++ |
| 3m-oxalate | 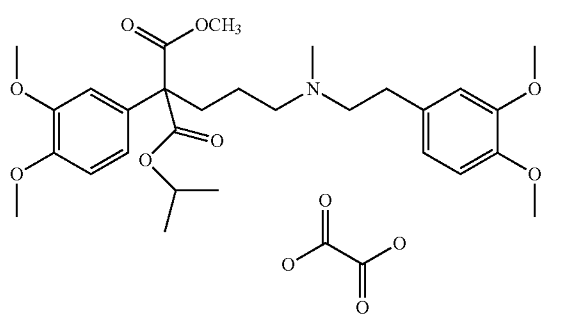 [SMILES: COC(=O)C(CCCN(C)CCc1ccc(OC)c(OC)c1)(C(=O)OC(C)C)c1ccc(OC)c(OC)c1 ; O=C(O)C(=O)O] | +++ |
| 3n-oxalate | 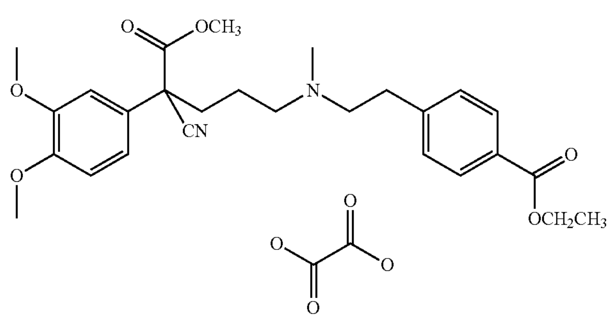 [SMILES: CCOC(=O)c1ccc(CCN(C)CCCC(C#N)(C(=O)OC)c2ccc(OC)c(OC)c2)cc1 ; O=C(O)C(=O)O] | +++ |

TABLE 4-continued

| Compound # | Structure | $K_i$ (μM) Ca Channel |
|---|---|---|
| 3o-oxalate* | 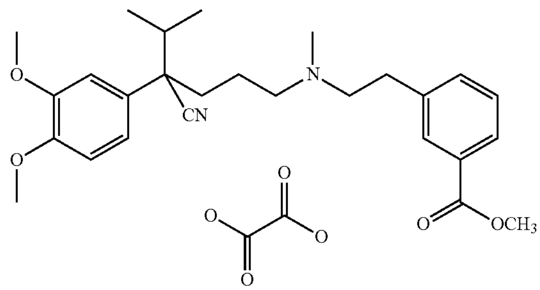 [SMILES: COC(=O)c1cccc(CCN(C)CCCC(C#N)(c2ccc(OC)c(OC)c2)C(C)C)c1 ; O=C(O)C(=O)O] | ++++ |
| 3p-oxalate | 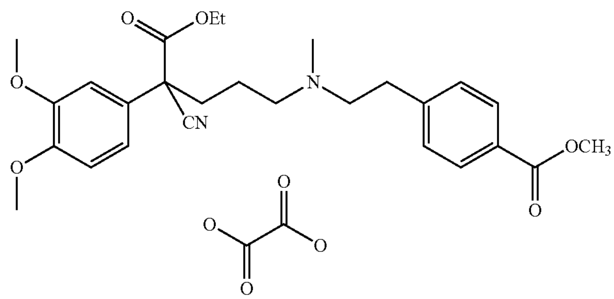 [SMILES: CCOC(=O)C(C#N)(CCCN(C)CCc1ccc(C(=O)OC)cc1)c1ccc(OC)c(OC)c1 ; O=C(O)C(=O)O] | +++ |
| 3q-oxalate | 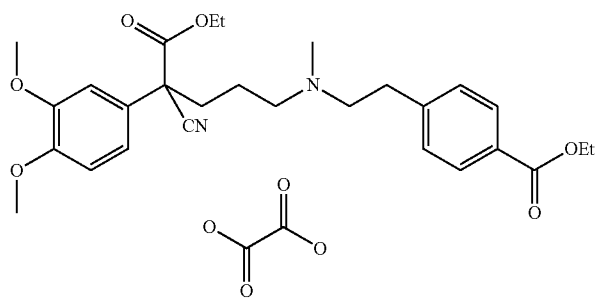 [SMILES: CCOC(=O)c1ccc(CCN(C)CCCC(C#N)(C(=O)OCC)c2ccc(OC)c(OC)c2)cc1 ; O=C(O)C(=O)O] | +++ |
| 3r-oxalate | 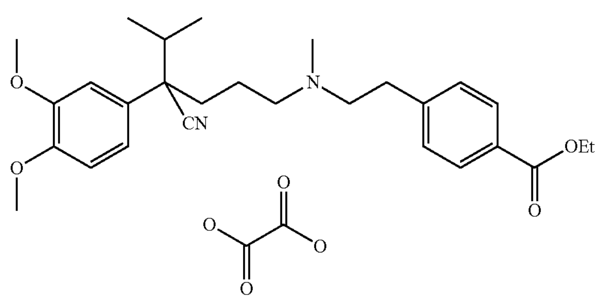 [SMILES: CCOC(=O)c1ccc(CCN(C)CCCC(C#N)(c2ccc(OC)c(OC)c2)C(C)C)cc1 ; O=C(O)C(=O)O] | ++++ |
| 3s-oxalate | 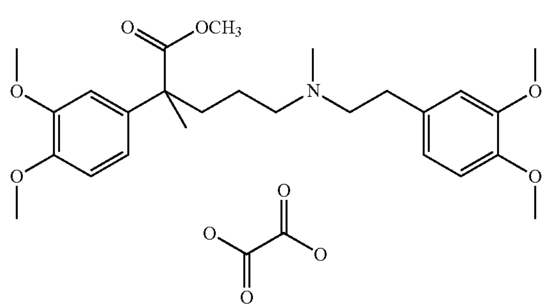 [SMILES: COC(=O)C(C)(CCCN(C)CCc1ccc(OC)c(OC)c1)c1ccc(OC)c(OC)c1 ; O=C(O)C(=O)O] | + |

TABLE 4-continued

| Compound # | Structure | $K_i$ (μM) Ca Channel |
|---|---|---|
| 3t-oxalate | 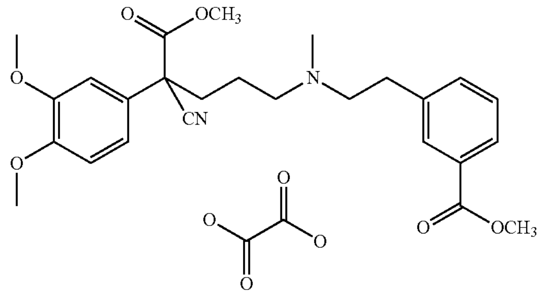 [SMILES: COC(=O)c1cccc(CCN(C)CCCC(C#N)(C(=O)OC)c2ccc(OC)c(OC)c2)c1 ; O=C(O)C(=O)O] | +++ |
| 3u-oxalate | 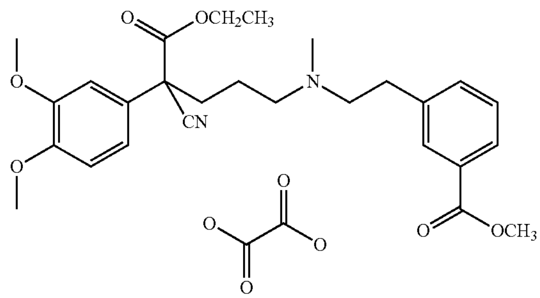 | ++++ |
| 3v-oxalate | 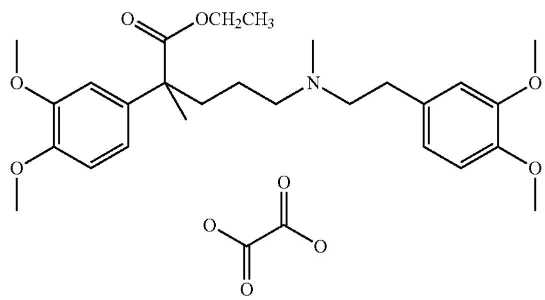 [SMILES: CCOC(=O)C(C)(CCCN(C)CCc1ccc(OC)c(OC)c1)c1ccc(OC)c(OC)c1 ; O=C(O)C(=O)O] | ++ |
| 3w-oxalate | 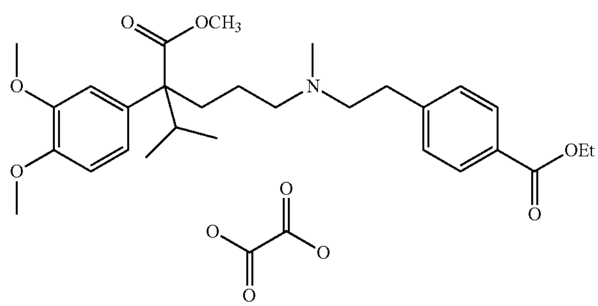 [SMILES: CCOC(=O)c1ccc(CCN(C)CCCC(C(=O)OC)(c2ccc(OC)c(OC)c2)C(C)C)cc1 ; O=C(O)C(=O)O] | +++ |
| 3x-oxalate | 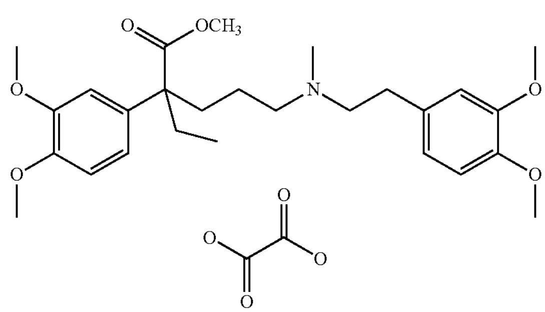 [SMILES: CCC(CCCN(C)CCc1ccc(OC)c(OC)c1)(C(=O)OC)c1ccc(OC)c(OC)c1 ; O=C(O)C(=O)O] | + |

TABLE 4-continued

| Compound # | Structure | K$_i$ (μM) Ca Channel |
|---|---|---|
| 3y-oxalate | 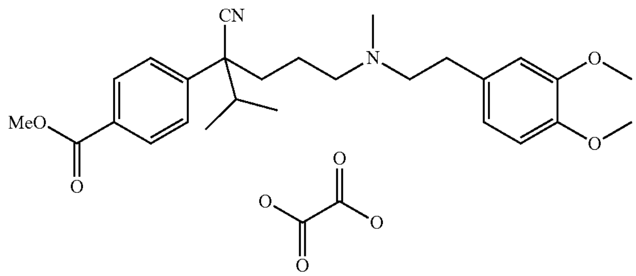 [SMILES: COC(=O)c1ccc(C(C#N)(CCCN(C)CCc2ccc(OC)c(OC)c2)C(C)C)cc1 ; O=C(O)C(=O)O] | +++ |
| 3z-oxalate | 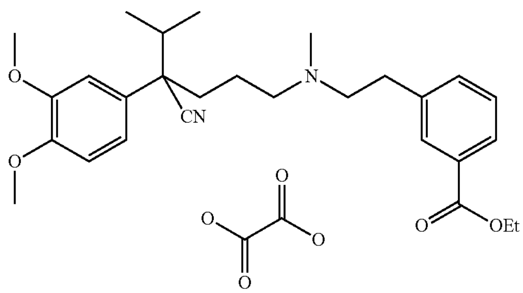 [SMILES: CCOC(=O)c1cccc(CCN(C)CCCC(C#N)(c2ccc(OC)c(OC)c2)C(C)C)c1 ; O=C(O)C(=O)O] | ++++ |
| 3aa-oxalate | 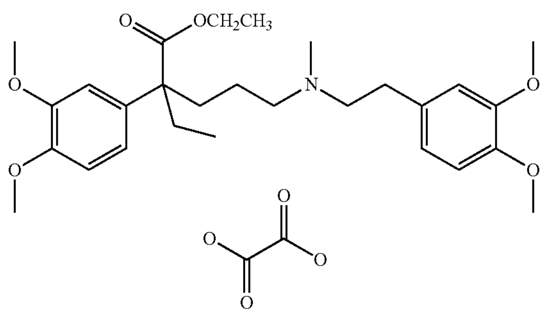 [SMILES: CCOC(=O)C(CC)(CCCN(C)CCc1ccc(OC)c(OC)c1)c1ccc(OC)c(OC)c1 ; O=C(O)C(=O)O] | +++ |
| 3ab-oxalate | 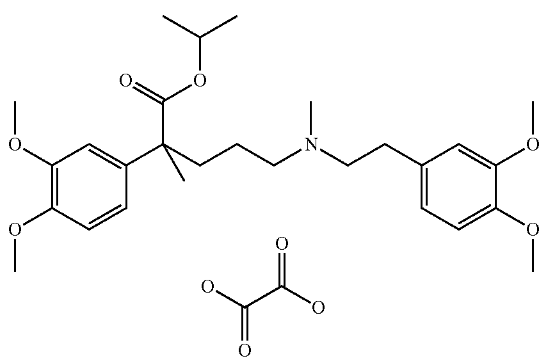 [SMILES: COc1ccc(CCN(C)CCCC(C)(C(=O)OC(C)C)c2ccc(OC)c(OC)c2)cc1OC ; O=C(O)C(=O)O] | ++ |
| 3ac-oxalate | 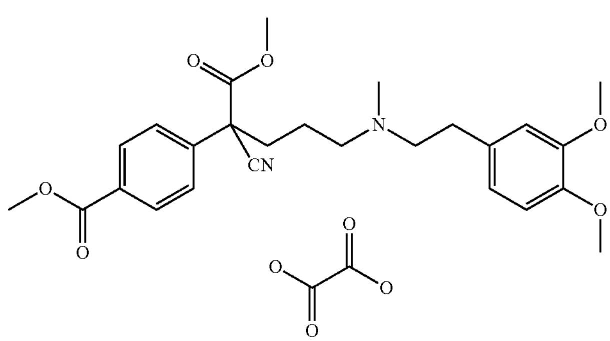 | ++ |

TABLE 4-continued

| Compound # | Structure | $K_i$ (μM) Ca Channel |
|---|---|---|
| 3ad-oxalate | 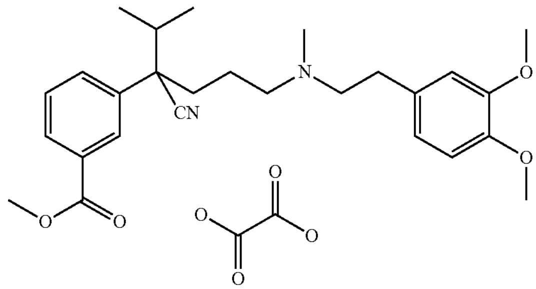 | ++++ |
| 3ae-oxalate | 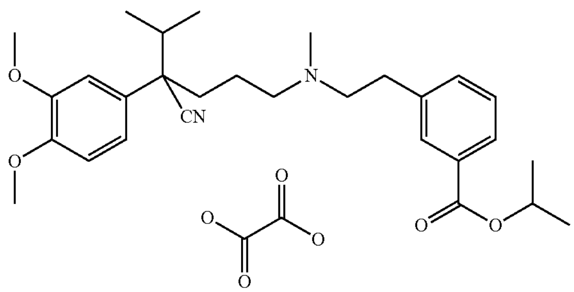 [SMILES: COc1ccc(C(C#N)(CCCN(C)CCc2cccc(C(=O)OC(C)C)c2)C(C)C)cc1OC ; O=C(O)C(=O)O] | ++++ |
| 3af-oxalate | 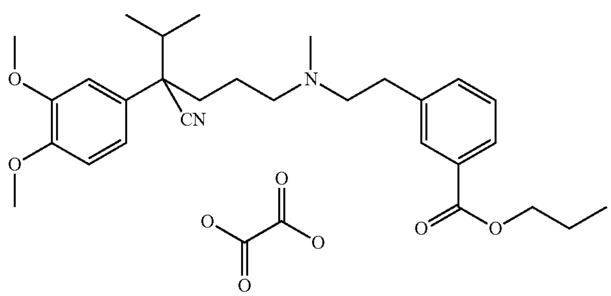 [SMILES: CCCOC(=O)c1cccc(CCN(C)CCCC(C#N)(c2ccc(OC)c(OC)c2)C(C)C)c1 ; O=C(O)C(=O)O] | ++++ |
| 3ag-oxalate | 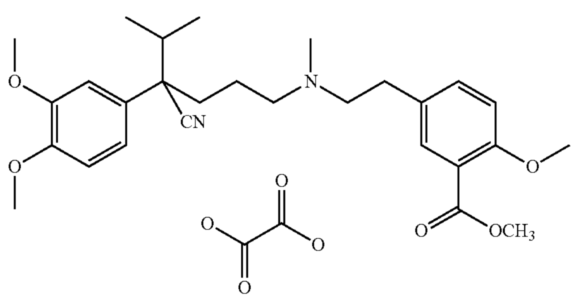 [SMILES: COC(=O)c1cc(CCN(C)CCCC(C#N)(c2ccc(OC)c(OC)c2)C(C)C)ccc1OC ; O=C(O)C(=O)O] | +++ |
| 3ah-oxalate | 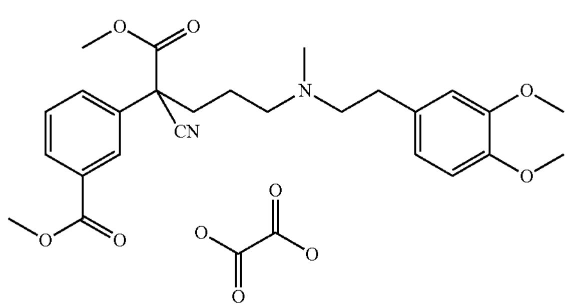 | ++ |

TABLE 4-continued

| Compound # | Structure | $K_i$ (μM) Ca Channel |
|---|---|---|
| 3ai-oxalate | 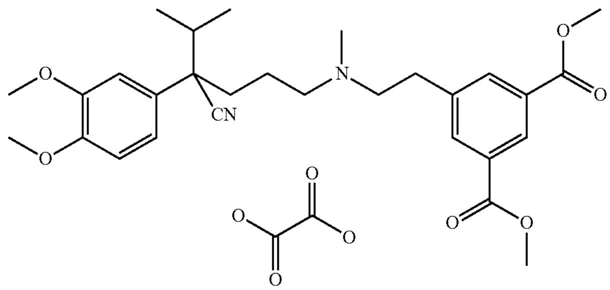 | ++++ |
| 3aj-oxalate | 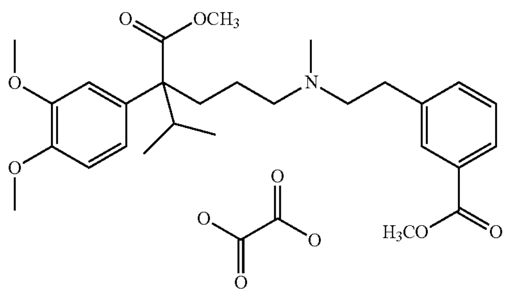 [SMILES: COC(=O)c1cccc(CCN(C)CCCC(C(=O)OC)(c2ccc(OC)c(OC)c2)C(C)C)c1 ; O=C(O)C(=O)O] | ++++ |
| 3ak-oxalate | 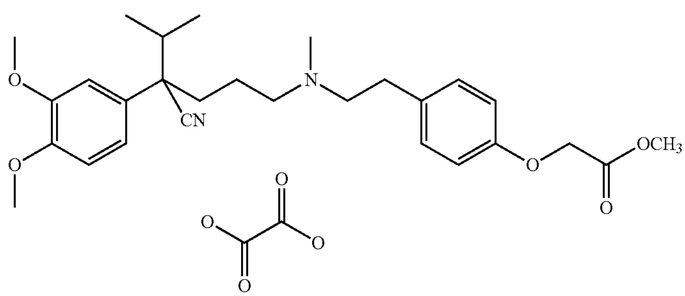 [SMILES: COC(=O)COc1ccc(CCN(C)CCCC(C#N)(c2ccc(OC)c(OC)c2)C(C)C)cc1 ; O=C(O)C(=O)O] | +++ |
| 3al-oxalate | 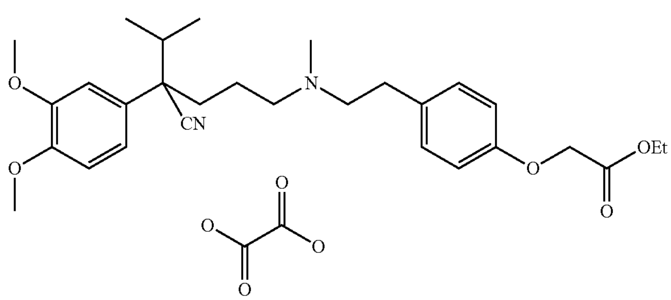 [SMILES: CCOC(=O)COc1ccc(CCN(C)CCCC(C#N)(c2ccc(OC)c(OC)c2)C(C)C)cc1 ; O=C(O)C(=O)O] | +++ |
| 3am-oxalate | 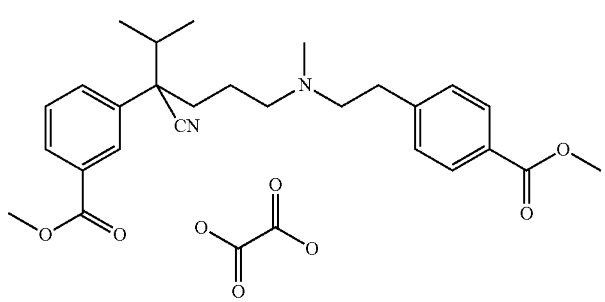 | +++ |

TABLE 4-continued

| Compound # | Structure | $K_i$ (μM) Ca Channel |
|---|---|---|
| 3an-oxalate | 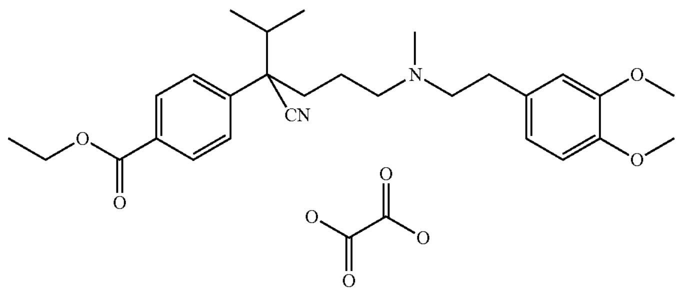 [SMILES: CCOC(=O)c1ccc(C(C#N)(CCCN(C)CCc2ccc(OC)c(OC)c2)C(C)C)cc1 ; O=C(O)C(=O)O] | ++++ |
| 3ao-oxalate | 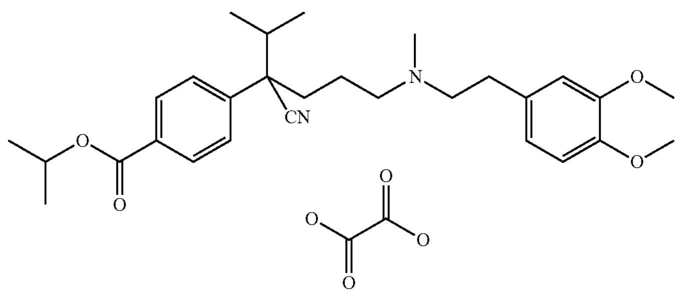 [SMILES: COc1ccc(CCN(C)CCCC(C#N)(c2ccc(C(=O)OC(C)C)cc2)C(C)C)cc1OC ; O=C(O)C(=O)O] | ++++ |
| 3ap-oxalate | 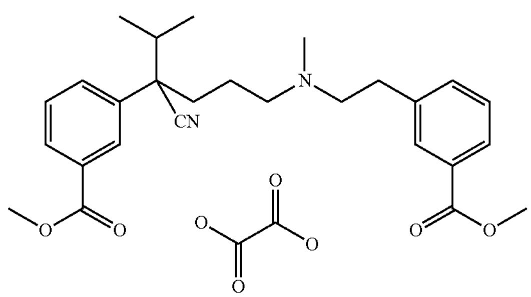 | ++++ |
| 3aq-oxalate | 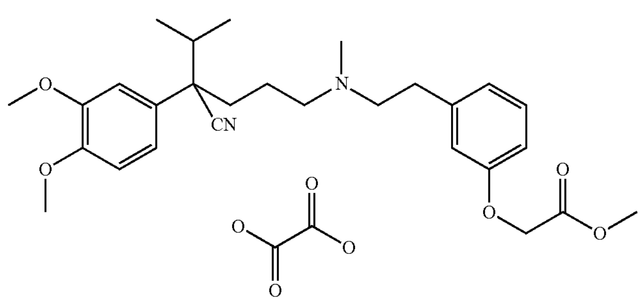 | + |
| 3ar-oxalate | 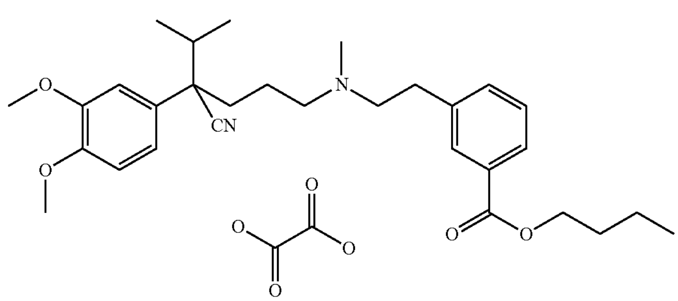 [SMILES: CCCCOC(=O)c1cccc(CCN(C)CCCC(C#N)(c2ccc(OC)c(OC)c2)C(C)C)c1 ; O=C(O)C(=O)O] | ++++ |

TABLE 4-continued

| Compound # | Structure | $K_i$ (μM) Ca Channel |
|---|---|---|
| 3as-oxalate | 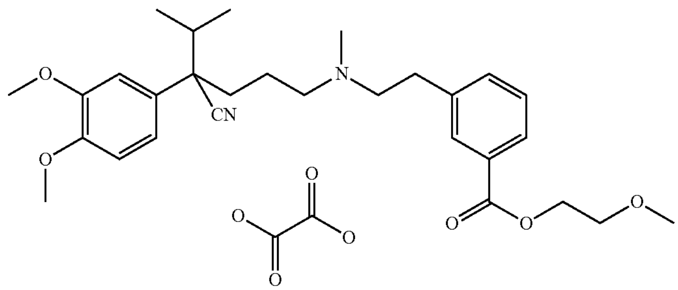 | ++++ |

Table Legend:
— = data not available
+ = $K_i$ is greater than 1.0 μM
++ = $K_i$ is 0.5-1.0 μM
+++ = $K_i$ is 0.1-0.5 μM
++++ = $K_i$ is less than 0.1 μM
*The corresponding HCl salts of (+/−)-3o, (−)-3o, and (+)-3o were assayed and afforded comparable results to those obtained with 3o-oxalate.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A method of treating a disease associated with decreased skeletal muscle blood flow, comprising administering to a patient in need thereof a therapeutically effective amount of a compound having the formula

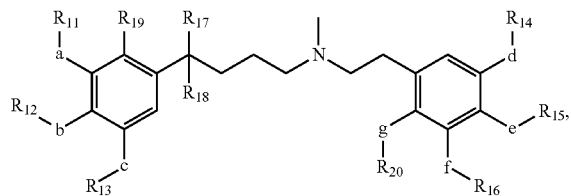

or a pharmaceutically acceptable addition salt thereof, or any enantiomer or diastereomer thereof, wherein
each a, b, c, d, e, and f is, independently, —CH$_2$-, —O—, —S—, or a single bond;
each $R_{11}$, $R_{12}$, $R_{13}$, $R_{14}$, $R_{15}$, $R_{16}$, and $R_{17}$ is, independently: H, lower alkyl, lower alkyl substituted with —CO$_2$(lower alkyl), lower alkyl substituted with —CO$_2$(lower alkoxyalkyl), lower alkyl substituted with fluorine or chlorine, lower alkoxyalkyl, lower alkoxyalkyl substituted with —CO$_2$(lower alkyl), lower alkoxyalkyl substituted with —CO$_2$(lower alkoxyalkyl), lower alkoxyalkyl substituted with fluorine or chlorine, or CO$_2$R$_{10}$;
each $R_{10}$ is, independently, lower alkyl or lower alkoxyalkyl;
$R_{18}$ is H or CN; and
$R_{19}$ is H, g is a single bond, and $R_{20}$ is H, wherein at least one of $R_{11}$, $R_{12}$, $R_{13}$, $R_{14}$, $R_{15}$, $R_{16}$, and $R_{17}$ is CO$_2$R$_{10}$, lower alkyl substituted with —CO$_2$(lower alkyl), lower alkyl substituted with —CO$_2$(lower alkoxyalkyl), lower alkoxyalkyl substituted with —CO$_2$(lower alkyl), or lower alkoxyalkyl substituted with —CO$_2$(lower alkoxyalkyl), wherein said disease associated with decreased skeletal muscle blood flow is Raynaud's phenomenon or intermittent claudication.

2. A method of treating a disease associated with decreased skeletal muscle blood flow, comprising administering to a patient in need thereof a therapeutically effective amount of a compound selected from the group consisting of:

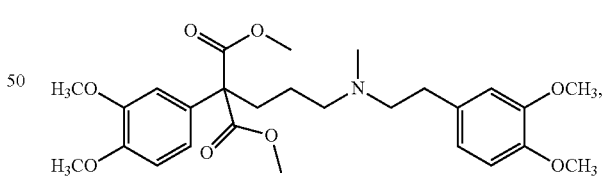

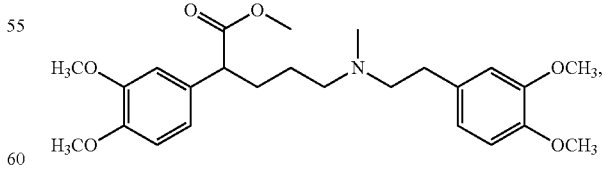

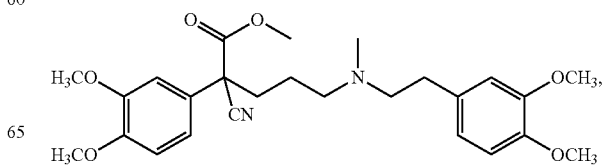

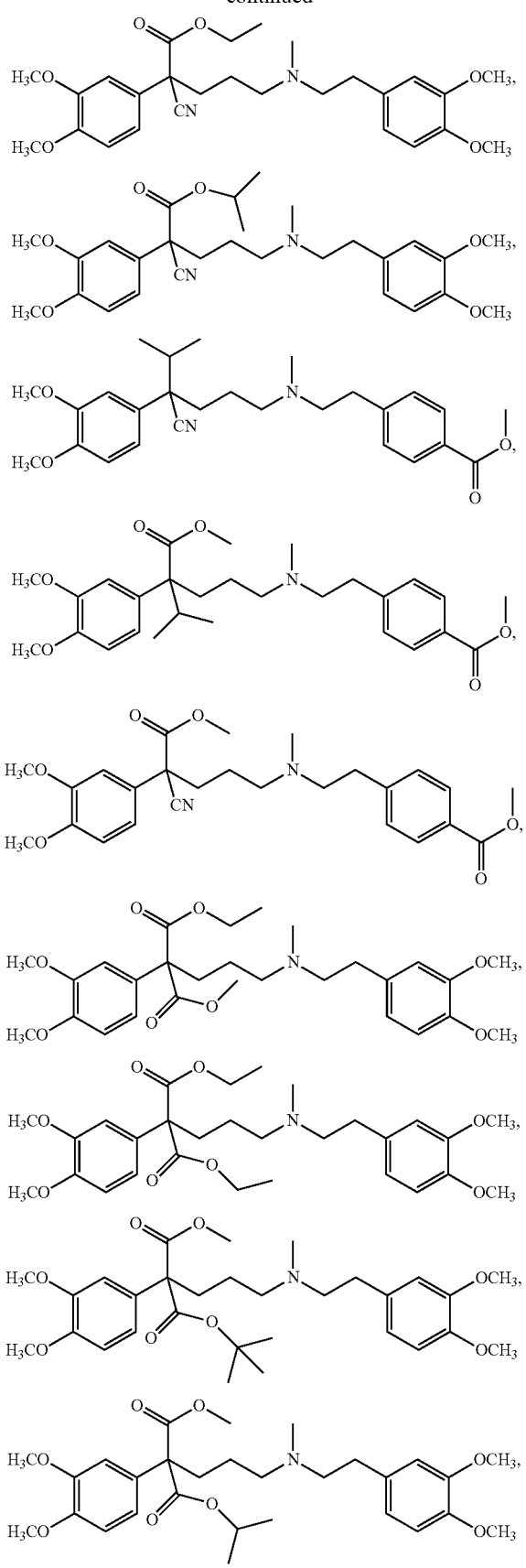
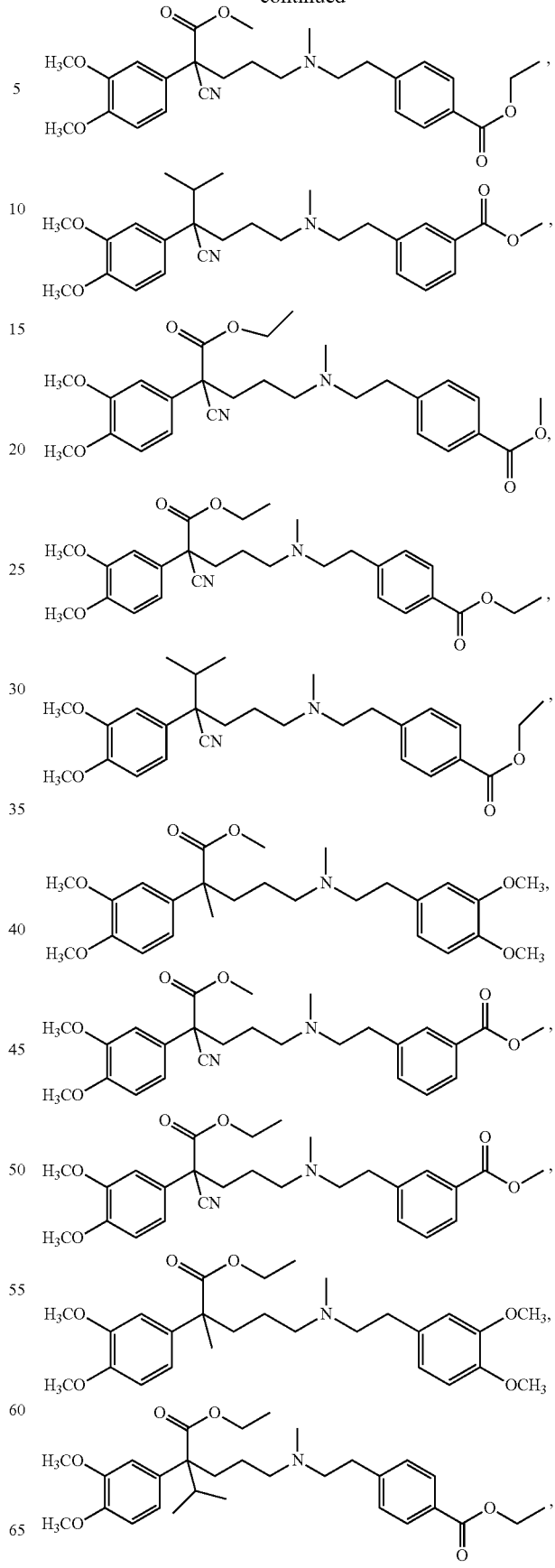

91
-continued
92
-continued
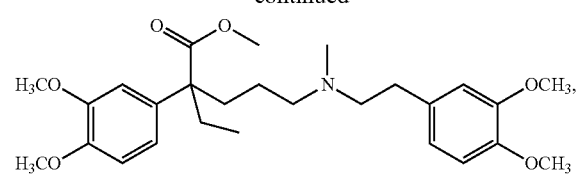
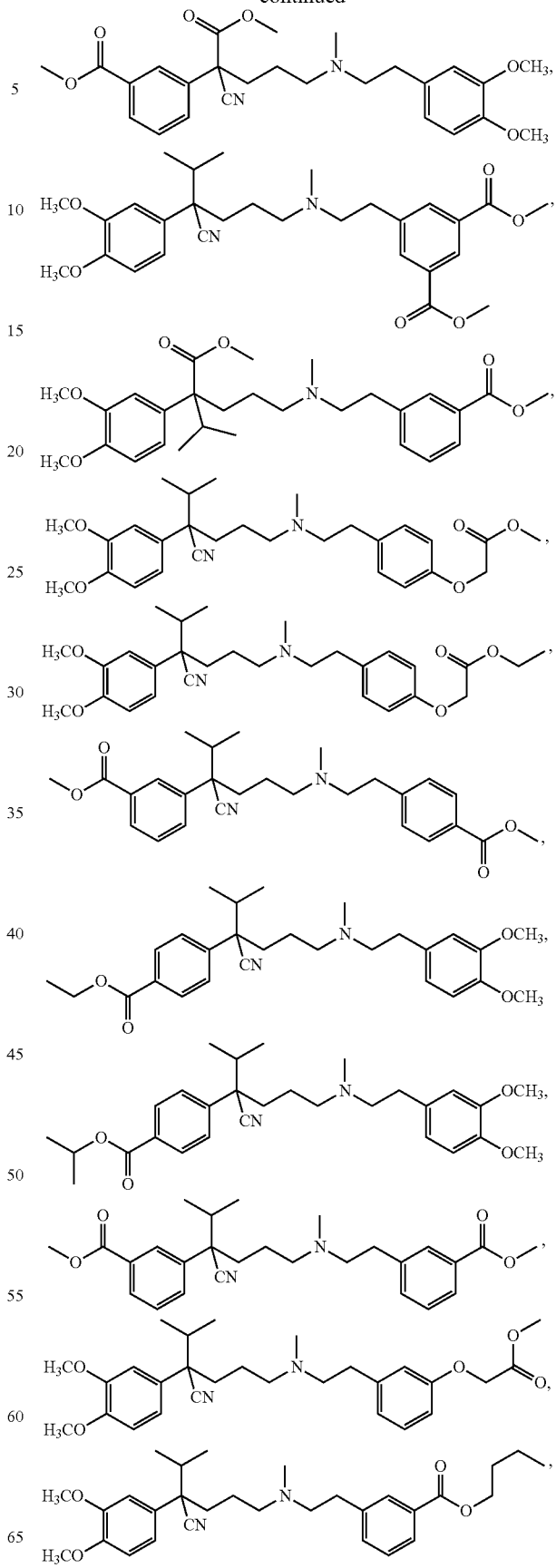

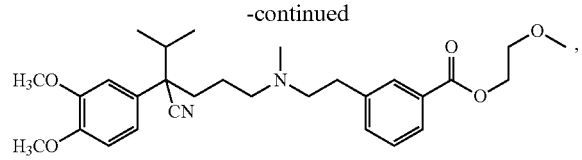

and

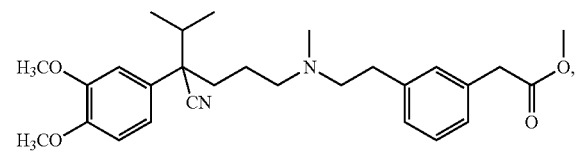

or a pharmaceutically acceptable addition salt thereof, wherein said disease associated with decreased skeletal muscle blood flow is Raynaud's phenomenon or intermittent claudication.

3. The method of claim 2, wherein said compound is selected from the group consisting of:

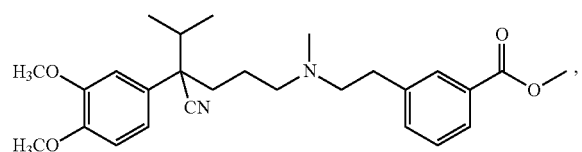

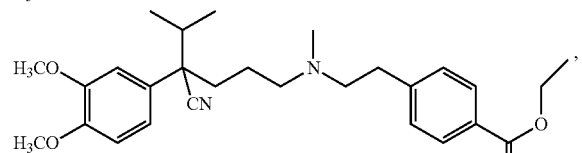

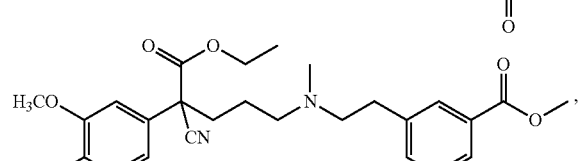

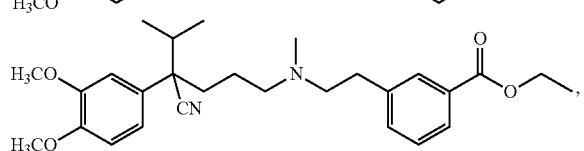

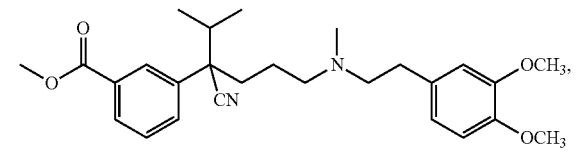

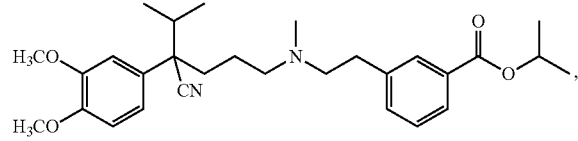

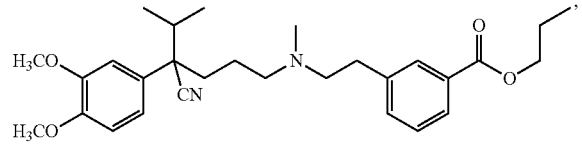

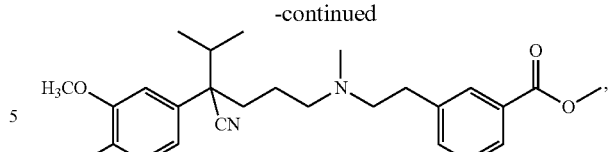

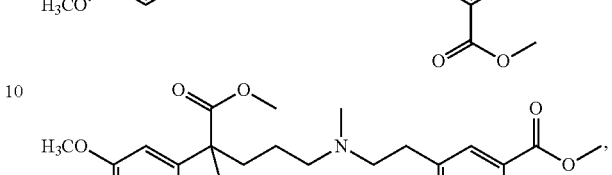

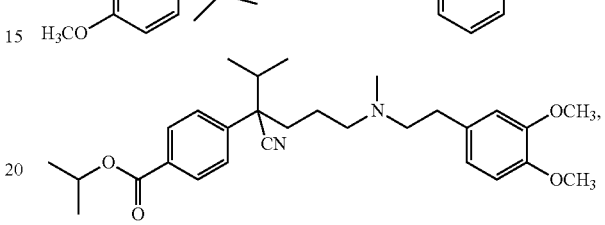

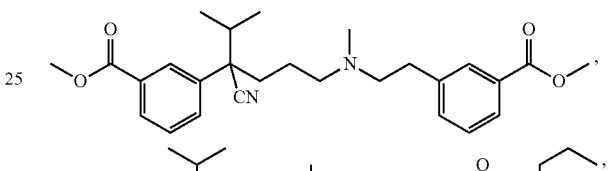

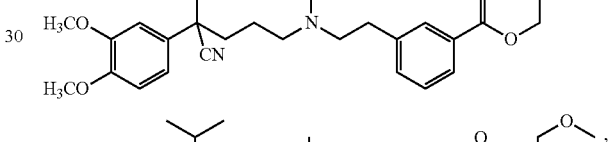

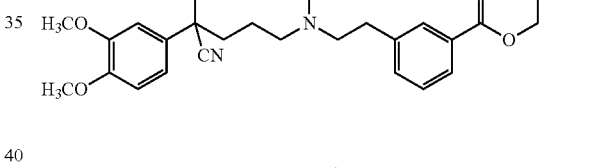

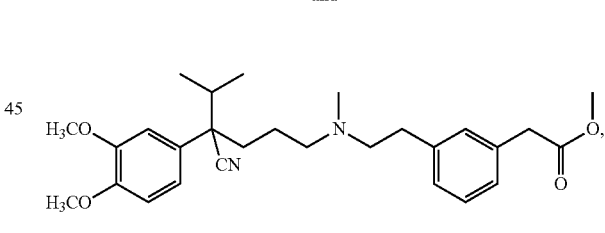

and

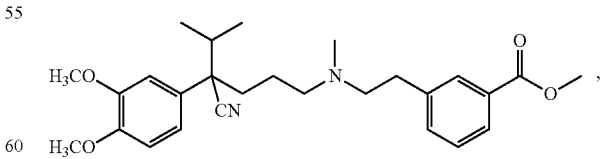

or a pharmaceutically acceptable addition salt thereof.

4. The method of claim 3, wherein said compound is or a pharmaceutically acceptable addition salt thereof.

* * * * *

UNITED STATES PATENT AND TRADEMARK OFFICE
CERTIFICATE OF CORRECTION

PATENT NO. : 9,737,503 B2
APPLICATION NO. : 15/262567
DATED : August 22, 2017
INVENTOR(S) : Martin P. Maguire et al.

Page 1 of 1

It is certified that error appears in the above-identified patent and that said Letters Patent is hereby corrected as shown below:

In the Specification

Column 50, Line 28, replace "1b: Diethyl" with --1h: Diethyl--.

Column 64, Line 65, replace "Reaction of Is" with --Reaction of 1s--.

Column 65, Lines 53-54, replace "Ethyl 4-(3-cyano-6-((3,4-dimethoxyphenethyl)(amino)-2-methylhexan-3-yl)benzoate" with --Ethyl 4-(3-cyano-6-((3,4-dimethoxyphenethyl)(methyl)amino)-2-methylhexan-3-yl)benzoate--.

In the Claims

Column 90, in the last compound of the column, replace " 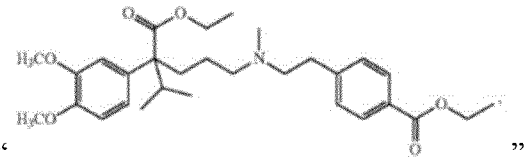 "

with -- 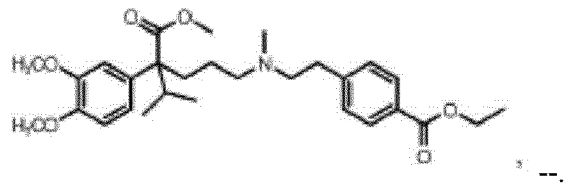 --.

Signed and Sealed this
Sixth Day of November, 2018

Andrei Iancu
*Director of the United States Patent and Trademark Office*